United States Patent
Lopez-Lopez et al.

(10) Patent No.: US 10,722,518 B2
(45) Date of Patent: Jul. 28, 2020

(54) OXAZINE DERIVATIVE FOR USE IN THE TREATMENT OR PREVENTION OF CEREBRAL AMYLOID ANGIOPATHY

(71) Applicant: Novartis AG, Basel (CH)

(72) Inventors: Cristina Lopez-Lopez, Basel (CH); Ulf Neumann, Rheinfelden (CH); Derya Shimshek, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/730,175

(22) Filed: Oct. 11, 2017

(65) Prior Publication Data

US 2018/0125853 A1 May 10, 2018

(30) Foreign Application Priority Data

Oct. 13, 2016 (EP) .................................. 16193770

(51) Int. Cl.
*A61K 31/5377* (2006.01)
*A61P 9/10* (2006.01)

(52) U.S. Cl.
CPC ............ *A61K 31/5377* (2013.01); *A61P 9/10* (2018.01)

(58) Field of Classification Search
CPC .............................. A61K 31/5377; A61P 9/10
USPC ....................................................... 514/228.2
See application file for complete search history.

(56) References Cited

U.S. PATENT DOCUMENTS

| 8,637,508 | B2 * | 1/2014 | Badiger ............... C07D 413/14 |
| | | | 514/233.8 |
| 8,865,712 | B2 | 10/2014 | Badiger et al. |
| 9,550,758 | B2 | 1/2017 | Badiger et al. |
| 10,035,794 | B2 | 7/2018 | Badiger et al. |
| 2005/0215884 | A1 | 9/2005 | Greicius et al. |
| 2015/0080703 | A1 | 3/2015 | Reiman |
| 2016/0130267 | A1 | 5/2016 | Juhl et al. |
| 2017/0320864 | A1 | 11/2017 | Badiger et al. |
| 2018/0036315 | A1 | 2/2018 | Lopez-Lopez et al. |

FOREIGN PATENT DOCUMENTS

| WO | WO2012/095469 A1 | 7/2012 |
| WO | WO2018/015868 A1 | 1/2018 |

OTHER PUBLICATIONS

Poirer et al., PNAS, (1995), v92, pp. 12260-12264.*
Combarros et al., (Sep. 1, 2009) Epistasis in sporadic Alzheimer's disease. Neurology of Aging. vol. 30, pp. 1333-1349; [available online Feb. 21, 2008].
Xue et al., (May 2015) Non-neuronal and neuronal BACE1 elevation in association with angiopathic and leptomeningeal Beta-amyloid deposition in the human brain. BMC Neurology. Biomed Central Ltd. vol. 15, No. 1, 2. p. 71.
Shinohara M et al., (2016) Impact of sex and APOE4 on cerebral amyloid angiopathy in Alzheimer's disease. Acta Neuropathol.; 132(2):225-234.
Babin AL et al., (2012) Bleomycin-induced lung injury in mice investigated by MRI: model assessment for target analysis. Magn. Reson. Med.; 67(2):499-509.
Beckmann N. et al., (2016) Longitudinal noninvasive magnetic resonance imaging of brain microhemorrhages in BACE inhibitor-treated APP transgenic mice, Neurobiology of Aging; 46:50-60.
Bobo B et al., (2013) STP Portion Paper: Recommended Practices for Sampling and Processing the Nervous System (Brain, Spinal Cord, Nerve; and Eye) during Nonclinical General Toxicity Studies, Toxicologic Pathology; 41(7):1028-1048.
Carlsson AC et al., (2013) Seven modifiable lifestyle factors predict reduced risk for ischemic cardiovascular disease and all-cause mortality regardless of body mass index: A cohort study, International Journal of Cardiology; 168:946-952.
Castellano JM et al., (2011) Human apoE Isoforms Differentially Regulate Brain Amyloid-b Peptide Clearance. Sci. Transl. Med.: 3(89);89ra57.
Charidmou A et al., (2011) Sporadic cerebral amyloid angiopathy revisited: recent insights into pathophysiology and clinical spectrum. J Neurol. Neurosurg. Psychiatry: 83(2):124-137.
Chen YW et al., (2006) Progression of white matter lesions and hemorrhages in cerebral amyloid angiopathy. Neurology; 67(1):83-87.
Cheng AL et al., (2013) Susceptibility-Weighted Imaging is More Reliable Than T2*-Weighted Gradient-Recalled Echo MRI for Detecting Microbleeds. Stroke; 44(10):2782-2786.
Dermaut B et al., (2001) Cerebral amyloid angiopathy is a pathogenic lesion in Alzheimer's disease due to a novel presenilin 1 mutation. Brain; 124:2383-2392.
Egger C et al., (2013) Administration of bleomycin via the oropharyngeal aspiration route leads to sustained lung fibrosis in mice and rats as quantified by UTE-MRI and history. PLoS One; 8(5):e63432.
Farias ST et al., (2008) The measurement of everyday cognition (ECog): Scale development and psychometric properties. Neuropsychology; 22(4):531-544.
Folstein MF et al., (1975) A practical method for grading the cognitive state of patients for the clinician. J. Psychiat Res.: 12:189-198.
Forlenza OV et al., (2015) Cerebrospinal fluid biomakers in Alzheimer's disease: Diagnostic accuracy and prediction of dementia; Alzheimers Dement. (Amst): 1(4):455-463.
Greenberg SM et al., (2014) Outcome Markers for Clinical Trials in Cerebral Amyloid Angiopathy. Lancet Neurol.; 13(4):419-428.
Gurol ME et al.; (2016) Florbetapir-PET to diagnose cerebral amyloid angiopathy: A prospective study. Neurology; 87(19):2043-2049.

(Continued)

*Primary Examiner* — Jeffrey S Lundgren
*Assistant Examiner* — Tori Strong
(74) *Attorney, Agent, or Firm* — Honigman LLP

(57) ABSTRACT

The present invention relates to an oxazine derivative BACE-1 inhibitor and pharmaceutical compositions comprising such oxazine derivative for use in the treatment or prevention of cerebral amyloid angiopathy and, in particular, wherein the patient carries one or two copies of the ApoE4 allele.

17 Claims, 30 Drawing Sheets

(56) References Cited

OTHER PUBLICATIONS

Herskovitz AZ et al., (2013) A Luminex assay detects amyloid β oligomers in Alzheimer's disease cerebrospinal fluid. PLoS ONE; 8(7):e67898 doi:10.1371/journal.pone.0067898.

Kaufer DI et al., (2000) Validation of the NPI-Q, a brief clinical form of the Neuropsychiatric Inventory. J. Neuropsychiatry Clin. Neuroscience; 12(2):233-239.

Knouff C et al., (1999) Apo E structure determines VLDL clearance and atherosclerosis risk in mice. J. Clin. Invest.; 103 (11):1579-1586.

Kumar-Singh S. (2008) Cerebral amyloid angiopathy: pathogentic mechanisms and link to dense amyloid plaques. Genes Brain Behav.; 7(Suppl. 1):67-82.

Langbaum JB et al., (2014) An empirically derived composite cognitive test score with inproved power to track and evaluate treatments for preclinical Alzheimer's disease. Alzheimers Dement.; 10(6):666-674.

Logsdon RG et al., (1999) Quality of life in Alzheimer's disease: Patient and caregiver reports. Journal of Mental Health & Aging; 5(1):21-32.

Luo G et al., (2004) CYP3A4 Induction by Xenobiotics: Biochemistry, Experimental Methods and Impact on Drug Discovery and Development. Current Drug Metabolism; 5(6):483-505.

Mattsson N et al., (2015) Predicting Reduction of Cerebrospinal Fluid β-Amyloid 42 in Cognitively Healthy Controls: JAMA Neurology: 72(5):554-560.

Morris JC, (1993) The Clinical Dementia Rating (CDR): Current version and scoring rules. Neurology; 43(11):2412-2414.

Paganetti PA et al., (1996) Amyloid precursor protein truncated at any of the gamma-secretase sites is not cleaved to beta-amyloid. J. Neurosci. Res.; 46(3):283-293.

Palmqvist S et al., (2016) Cerebrospinal fluid analysis detects cerebral amyloid-β accumulation earlier than position emission tomography. Brain; 139:1226-1236.

Pfeifer M et al., (2002) Cerebral Hemorrhage After Passice Anti-Aβ Immunotherapy. Science; 298(5597):1379.

Posner K et al., (2011) The Columbia-Suicide Severity Rating Scale: Initial Validity and Internal Consistency Findings From Three Multisite Studies With Adolescents and Adults. Am. J. Psychiatry: 168(12):1266-1277.

Quintino-Santos SR et al., (2012) Homozygosity for the APOE E4 allele is soley associated with lower cognitive performance in Brazilian community dwelling older adults—The Bambui Study. Rev. Bras. Psiquiatr.; 34(4):440-445.

Randolph et al., "The Repeatable Battery for the Assessment of Neuropsychological Status (RBANS):Preliminary Clinical Validity", Journal of Clinical and Experiment Neuropsychology, vol. 20, No. 3, pp. 310-319, (1998).

Raven JC et al., (1992) Standard progressive matrices-1992 edition: Raven manual: Section 3. Oxford Psychologists Press: Oxford.

Raven JC, (2000) Standard Progressive Matrices-1998 Edition, updated 2000. Manual for Standard Progressive Matrices (Section 3): NCS Person, Inc., San Antonio.

Schreiber S et al. (2015) Comparison of Visual and Quantitative Florbetapir F 18 Positron Emission Tomography Anaylsis in Predicting Mild Cognitive Impairment Outcomes, JAMA Neurol.: 72(10):1183-1190.

Sevrioukova IF, Poulos TL, (2015) Current Approaches for Investigating and Predicting Cytochrome P450 3A4-Ligand Interactions. Adv. Exp. Med. Biol.: 851-83-105.

Sheikh JI, Yesavage JA, (A986) Geriatric Depression Scale (GDS). Recent evidence and development of a shorter version. In T.L. Brink (Ed.), Clinical Gerontology: A Guide to Assessment and Intervention (pp. 165-173). NY The Haworth Press, Inc.

Sperling RA et al., (2011) Toward defining the preclinical stages of Alzheimer's disease; Recommendations from the National Institute on Aging and the Alzheimer's Association workgroup. Alzheimers Dement.; 7(3):280-292.

Thorgrimsen L et al., (2003) Whose Quality of Life Is It Anyway? The Validity and Reliabilty of the Quality of Life-Alzheimer's Disease (QoI-AD) Scale. Alzheimer Dis. Assoc. Disord.; (74):201-208.

Verghese PB et al., (2011) Roles of Apolipoprotein E in Alzheimer's disease and Other Neurological Disorders. Lancet Neurol.; 10(3): 241-252.

Winkler DT et al., (2001), Spontaneous hemorrhagic stroke in a mouse model of cerebral amyloid angiopathy. J. Neurosci.; 21(5):1619-1627.

Struyfs et al., (2015) Diagnostic Accuracy of Cerebrospinal Fluid Amyloid-β Isoforms for Early and Differential Dementia Diagnosis. Journal of Alzheimer's Disease. vol. 45. pp. 813-822.

Keller Daniel M., (Mar. 24, 2015) New Drug greatly reduces amyloid in CSF Plasma. Medscape pp. 1-3 [Downloaded Mar. 26, 2015 at http://www.medspace.com/viewarticle/841937].

Viswanathan, A. and Greenberg S., (2011) Cerebral Amyloid Angiopathy in the Elderly. Ann Neur. vol. 70, pp. 871-880.

Gandy et al., (2011) Alzheimer's Therapy: a BACE in the hand?. Nature Medicine. col. 17, No. 8, pp. 932-933.

Janelidze S et al., (2016) Swedish BioFINDER study group, Hansson O CSF Aβ42/Aβ40 and Aβ42/Aβ38 ratios: better diagnostic markers of Alzheimer disease. Ann Clin Transl Neurol. 3(3):154-65.

Schrader-Fischer G, Paganetti PA, (1996) Effect of alkalizing agents on the processing of the β-amyloid precursor protein. Brain Research, 716(1-2):91-100.

Schrader-Fischer G et al., (1997) Insertion of Lysosomal Targeting Sequences to the Amyloid Precursor Protein Reduces Secretion of βA4. Journal of Neurochemistry 68(4):1571-1580.

Sturchler-Pierrat C et al., (1997) Two amyloid precursor protein trangenic mouse models with Alzheimer disease-like pathology Proc. Natl. Acad. Sci. USA: 94(24):13287-13292.

Thal DR et al., (2002) Two types of sporadic cerebral amyloid angiopathy. J. Neuropathol. Exp. Neurol.; 61: 282-293.

Albert, MS et al. The diagnosis of mild cognitive impairment due to Alzheimer's disease: Recommendations from the National Institute on Aging-Alzheimer's Association workgroups on diagnostic guidelines for Alzheimer's disease. Alzheimer's & Dementia. Vol. 7, Issue 3, pp. 270-279. May 2011.

Barthel, H et al. Cerebral amyloid-βPET with florbetaben (18F) in patients with Alzheimer's disease and healthy controls: A multicentre phase 2 diagnostic study. The Lancet Neurology. vol. 10, Issue 5, pp. 424-435. May 2011.

Chouliaras, L et al. Epigenetic regulation in the pathophysiology of Alzheimer's disease. Progress in Neurobiology. Vol. 90, Issue 4, pp. 498-510. Apr. 2010.

Corder, EH et al. Gene dose of apolipoprotein E type 4 allele and the risk of Alzheimer's disease in late onset families. Science. Vol. 261, Issue 5123, pp. 921-923. Aug. 13, 1993.

Cummings, JL et al. Alzheimer's disease drug-development pipeline: few candidates, frequent failures. Alzheimer's Research & Therapy. Jul. 3, 2014, 6:37.

Evin, G. Future Therapeutics in Alzheimer's Disease: Development Status of BACE Inhibitors. BioDrugs. Vol. 30, Issue 3, pp. 173-194. Mar. 29, 2016.

Foster, NL et al. FDG-PET improves accuracy in distinguishing frontotemporal dementia and Alzheimer's disease. Brain. Vol. 130, Issue 10, pp. 2616-2635. Oct. 1, 2007.

Genin, E et al. APOE and Alzheimer disease: A major gene with semi-dominant inheritance. Molecular Psychiatry. Vol. 16, pp. 903-907. May 10, 2011.

Harada, R et al. 18F-THK5351: A Novel PET Radiotracer for Imaging Neurofibrillary Pathology in Alzheimer Disease. The Journal of Nuclear Medicine. Vol. 57, Issue 2, pp. 208-214. Feb. 2016.

Head, E et al. Alzheimer's Disease in Down Syndrome. European Journal of Neurodegenerative Diseases. Vol. 1, No. 3, pp. 353-364. 2012.

Jansen, WJ et al. Prevalence of Cerebral Amyloid Pathology in Persons Without Dementia: A Meta-analysis. J AMA. Vol. 313, No. 19, pp. 1924-1938, May 19, 2015.

Kramp, VP et al. List of Drugs in Development for Neurodegenerative Diseases: Update Jun. 2010. Neuro—Degenerative Diseases. Volume 8, Issue 1-2, pp. 44-94. Dec. 2010.

(56) References Cited

OTHER PUBLICATIONS

Liu, CC et al. Apolipoprotein E and Alzheimer disease: risk, mechanisms and therapy. Nature Reviews Neurology. 9, pp. 106-118. Jan. 8, 2013. Volume 9, 99. 106-118. Jan. 8, 2013.

McKhann, GM et al. The diagnosis of dementia due to Alzheimer's disease: Recommendations from the National Institute on Aging-Alzheimer's Association workgroups on diagnostic guidelines for Alzheimer's disease. Alzheimer's & Dementia. Volume 7, Issue 3, pp. 263-269. May 2011.

Medina, M et al. New perspectives on the role of tau in Alzheimer's disease. Implications for therapy. Biochemical Pharmacology. Volume 88, Issue 4, pp. 540-547. 15 Apr. 2014.

Neumann, U et al. A novel BACE inhibitor NB-360 shows a superior pharmacological profile and robust reduction of amyloid-$\beta$ and neuroinflammation in APP transgenic mice. Molecular Neurodegeneration. Volume 10, No. 44. Sep. 3, 2015.

O'Brien, RJ et al. Amyloid Precursor Protein Processing and Alzheimer's Disease. Annual Review of Neuroscience. Volume 34, pp. 185-204. Mar. 29, 2011.

Pannee, J et al. Reference measurement procedure for CSF amyloid beta (A$\beta$)1-42 and the CSF A$\beta$1-42/A$\beta$1-40 ratio—a cross—validation study against amyloid PET. Journal of Neurochemistry. Volume 139, Issue 4, pp. 651-658. Aug. 31, 2016.

Rahier, J et al. Determination of antigen concentration in tissue sections by immunodensitometry.Laboratory Investigation; a Journal of Technical Methods and Pathology. Volume 61, No. 3, pp. 357-363. Sep. 1, 1989.

Ruifrok, AC et al. Quantification of histological staining by color deconvolution. Anal Quant Cytol Histol. Volume 23, pp. 291-299. 2001.

Schipke, CG et al. Correlation of florbetaben PET imaging and the amyloid peptide AR42 in cerebrospinal fluid. Psychiatry Research: Neuroimaging. Volume 265, pp. 98-101. Jul. 30, 2017.

Shimshek, DR et al. Pharmacological BACE1 and BACE2 inhibition induces hair depigmentation by inhibiting PMEL17 processing in mice. Scientific Reports vol. 6, Article number: 21917. Feb. 25, 2016.

U.S. Appl. No. 15/385,147 entitled "Novel Heterocyclic Derivatives and Their Use in the Treatment of Neurological Disorders", filed Dec. 20, 2016.

Vlassenko, AG et al. PET amyloid-beta imaging in preclinical Alzheimer's disease.Biochimica et Biophysica Acta (BBA)—Molecular Basis of Disease. Volume 1822, Issue 3, pp. 370-379. Mar. 2012.

Weigand, SD et al. Transforming cerebrospinal fluid A$\beta$42 measures into calculated Pittsburgh compound B units of Abrain$\beta$ amyloid. Alzheimer's & Dementia. Volume 7, Issue 2, pp. 133-141. Mar. 2011.

U.S. Appl. No. 16/020,212 entitled "Novel Heterocyclic Derivatives and Their Use in the Treatment of Neurological Disorders", filed Jun. 27, 2018.

Office Action dated Oct. 1, 2018 for U.S. Appl. No. 15/651,845, filed Jul. 17, 2017.

Jul. 17, 2017, U.S. Appl. No. 15/651,845, Lopez-Lopez et al.

Aisen PS et al., (2017) on the path to 2025: understanding the Alzheimer's disease continuum. Alzheimers Res. Ther.; 9:60 (pp. 1-10).

Akiyama H et al., (2000) Inflammation and Alzheimer's disease. Neurobiol. Aging; 21:383-421.

Ashford JW et al., (2002) Non-familial Alzheimer's disease is mainly due to genetic factors. J. Alzheimers Dis.; 4:169-177.

Attems J et al., (2011) Review: Sporadic cerebral amyloid angiopathy. Neuropathol Appl Neurobiol.; 37:75-93.

Attems J, Jellinger KA, (2014) The overlap between vascular disease and Alzheimer's disease—lessons from pathology. BMC Medicine; 12:206 (pp. 1-12).

Baranello RJ et al., (2015) Amyloid-beta protein clearance and degradation (ABCD) pathways and their role in Alzheimer's disease. Curr. Alzheimer Res.; 12:32-46.

Bateman RJ et al., (2012) Clinical and biomarker changes in dominantly inherited Alzheimer's disease. N. Engl. J. Med.; 367:795-804.

Bertram L, Tanzi RE, (2008) Thirty years of Alzheimer's disease genetics: the implications of systematic meta-analyses. Nat. Rev. Neurosci.; 9:768-778.

Biffl A, Greenberg SM, (2011) Cerebral Amyloid Angiopathy: A Systematic Review. J. Clin. Neural.; 7:1-9.

Bloom GS, (2014) Amyloid-beta and tau: the trigger and bullet in Alzheimer disease pathogenesis. JAMA Neurol.; 71:505-508.

Bonham LW et al., (2016) Age-dependent effects of APOE $\epsilon$4 in preclinical Alzheimer's disease. Ann. Clin. Transl. Neural.; 3(9):668-677.

Bums A, Iliffe S, (2009) Alzheimer's disease. BMJ; 338:b158 (11 pages).

Cacciaglia R er al., (2018) Effects of APOE-epsilon4 allele load on brain morphology in a cohort of middle-aged healthy individuals with enriched genetic risk for Alzheimer's disease. Alzheimers Demerit; 14:902-912.

Cano SJ et al., (2010) The ADAS-cog in Alzheimer's disease clinical trials: psychometric evaluation of the sum and its parts. J. Neurol. Neurosurg. Psychiatry; 81:1363-1368.

Caputo A., Thomas R., (2016) Multiplicity adjustment in a complex clinical trial in preclinical Alzheimer's disease. Slides presented at Promoting Statistical Insight, May 25, 2016, Berlin, Germany.

Caputo A. et al., (2016) When statistics and pharmacometrics join forces for advanced quantitative drug development: A case study. Slides presented at World Conference on Pharmacometrics (WCoP), Aug. 22, 2016, Brisbane, Australia.

Caputo A et al. (2017) a model for Alzheimer's disease in the prevention setting. Value in Health. Conference: ISPOR 20th Annual European Congress. United Kingdom; 20(9):A756.

Caputo A et al., (2017) Rationale for selection of primary endpoints in the Alzheimer prevention initiative generation study in cognitively healthy APOE4 homozygotes. Alzheimer's and Dementia. Conference: Alzheimer's Association International Conference, AAIC Jul. 16-20, 2017. United Kingdom; 13(7):P1452.

Caputo A et al., (2017) Rationale for selection of primary endpoints in the Alzheimer prevention initiative generation study in cognitively healthy APOE4 homozygotes. Slides presented at: Alzheimer's Association International Conference, AAIC Jul. 16-20, 2017. London, United Kingdom.

Caselli RJ et al., (2009) Longitudinal Modeling of Age-Related Memory Decline and the APOE £4 Effect. N. Engl. J. Med.; 361:255-263.

Chen K et al., (2007) Correlations between apolipoprotein E epsilon4 gene dose and whole brain atrophy rates. Am. J. Psychiatry; 164(6):916-921.

Chen K et al., (2015) Improved Power for Characterizing Longitudinal Amyloid-$\beta$ PET Changes and Evaluating Amyloid-Modifying Treatments with a Cerebral White Matter Reference Region. J. Nucl. Med.; 56(4):560-566.

ClinicalTrials.gov. A Study of CAD106 and CNP520 Versus Placebo in Participants at Risk for the Onset of Clinical Symptoms of Alzheimer's Disease (Generation S1); Version 5, Nov. 10, 2016; https://clinicaltrials.gov/ct2/history/ NCT025655117V_5= ViewitStudyPageTop. Accessed May 16, 2019.

ClinicalTrials.gov. A Study of CNP520 Versus Placebo in Participants at Risk for the Onset of Clinical Symptoms of Alzheimer's Disease (Generation S2); Version 1, Apr. 24, 2017; https://clinicaltrials.gov/cOhistory/NCT03131453? V_1=View#StudyPageTop. Accessed May 16, 2019.

Cole SL, Vassar R, (2007) the basic biology of BACE1: a key therapeutic target for Alzheimer's disease. Curr. Genomics; 8:509-530.

Cruchaga C et al., (2014) Rare coding variants in the phospholipase D3 gene confer risk for Alzheimer's disease. Nature; 505:550-554.

Cummings J et al., (2016) Drug development in Alzheimer's disease: the path to 2025. Alzheimers Res. Ther.; 8:39 (pp. 1-12). 0.

Das B, Yan R, (2017) Role of BACE1 in Alzheimer's synaptic function. Trans!. Neurodegener.; 6:23 (pp. 1-8).

(56) References Cited

OTHER PUBLICATIONS

Dubois B et al., (2014) Advancing research diagnostic criteria for Alzheimer's disease: the IWG-2 criteria. Lancet Neurol.; 13:614-629.
Dubois B et al., (2016) Preclinical Alzheimer's disease: Definition, natural history, and diagnostic criteria. Alzheimers Dement.; 12:292-323.
Duff K et al., (2008) Utility of the RBANS in detecting cognitive impairment associated with Alzheimer's disease: sensitivity, specificity, and positive and negative predictive powers. Arch. Clin. Neuropsychol.; 23:603-612.
Dulsat C., (2016) Alzheimer's Association International Conference on Alzheimer's Disease 2016 (AAIC 2016). Toronto, Canada—Jul. 24-28, 2016. Drugs of the Future 41(8):525-530.
Farrer LA et al., (1997) Effects of age, sex, and ethnicity on the association between apolipoprotein E genotype and Alzheimer disease. A meta-analysis. APOE and Alzheimer Disease Meta Analysis Consortium. JAMA; 278:1349-1356.
Fiandaca MS et al., (2014) The critical need for defining preclinical biomarkers in Alzheimer's disease. Alzheimers Dement.; 10:S196-S212.
Fleisher AS et al., (2011) Using positron emission tomography and florbetapir F18 to image cortical amyloid in patients with mild cognitive impairment or dementia due to Alzheimer disease. Arch. Neurol.; 68(11):1404-1411.
Fleisher AS et al., (2012) Florbetapir PET analysis of amyloid-β deposition in the presenilin 1 E280A autosomal dominant Alzheimer's disease kindred: a cross-sectional study. Lancet Neurol.; 11(12):1057-1065.
Fleisher AS et al., (2015) Associations between biomarkers and age in the presenilin 1 E280A autosomal dominant Alzheimer disease kindred: a cross-sectional study. JAMA Neurol.; 72(3):316-324.
Fotiadis P et al., (2016) Cortical atrophy in patients with cerebral amyloid angiopathy: A case-control study. Lancet Neurol.; 15:811-819.
Frisoni GB et al., (2017) Strategic roadmap for an early diagnosis of Alzheimer's disease based on biomarkers. Lancet Neurol.; 16:661-676.
Gomez-Isla T et al., (1996) Clinical and pathological correlates of apolipoprotein E epsilon 4 in Alzheimer's disease. Ann. Neural.; 39:62-70.
Greenberg SM et al., (2004) Amyloid angiopathy-related vascular cognitive impairment. Stroke; 35:2616-2619.
Haan MN et al., (1999) The role of APOE epsilon4 in modulating effects of other risk factors for cognitive decline in elderly persons. JAMA; 282:40-46.
Haass C, (2004) Take five—BACE and the gamma-secretase quartet conduct Alzheimer's amyloid beta-peptide EMBO J.; 23:483-488. generation.
Howard KL, Filley CM, (2009) Advances in genetic testing for Alzheimer's disease. Rev. Neurol. Dis.; 6:26-32.
Hu X et al., (2006) Bace1 modulates myelination in the central and peripheral nervous system. Nat. Neurosci.; 9:1520-1525.
Huynh TV et al., (2017) Apolipoprotein E and Alzheimer's disease: the influence of apolipoprotein E on amyloid-beta and other amyloidogenic proteins. J. Lipid. Res.; 58:824-836.
Jack CR et al., (2013) Brain 13-amyloid load approaches a plateau. Neurology; 89:890-896.
Jack CR et al., (2016) A/T/N: An unbiased descriptive classification scheme for Alzheimer disease biomarkers. Neurology; 87:539-547.
Jonsson T et al., (2012) A mutation in App protects against Alzheimer's disease and age-related cognitive decline. Nature; 488:96-99.
Jonsson T et al., (2013) Variant of TREM2 associated with the risk of Alzheimer's disease. N. Engl. J. Med.; 368:107-116.
Karch CM, Goate AM, (2015) Alzheimer's disease risk genes and mechanisms of disease pathogenesis. Biol. Psychiatry; 77:43-51.
Karin A et al., (2014) Psychometric evaluation of ADAS-COG and NTB for measuring drug response. Acta. Neurol. Scand.; 129:114-122.
Karran E et al., (2011) The amyloid cascade hypothesis for Alzheimer's disease: an appraisal for the development of therapeutics. Nat. Rev. Drug Discov.; 10:698-712.
Keskin AD et al., (2017) BACE inhibition-dependent repair of Alzheimer's pathophysiology. Proc. Natl. Acad. Sci. U S A; 114:8631-8636.
Khoury R et al., (2017) Recent Progress in the Pharmacotherapy of Alzheimer's Disease. Drugs Aging; 34 (11):811-820.
Klohs J et al., (2014) Imaging of cerebrovascular pathology in animal models of Alzheimer's disease. Front. Aging Neurosci.; pp. 1-30.
Kosik KS et al., (2015) Homozygosity of the autosomal dominant Alzheimer disease presenilin 1 E280A mutation. Neurology; 84(2):206-208.
Lahoz C et al., (2001) Apolipoprotein E genotype and cardiovascular disease in the Framingham Heart Study. Atherosclerosis; 154:529-537.
Langbaum JB et al., (2013) Ushering in the study and treatment of preclinical Alzheimer disease. Nat. Rev. Neural.; 9 (7):371-381.
Langbaum J et al., (2016) The alzheimer's prevention initiative (API) autosomal dominant alzheimer's disease (ADAD) trial; Neurobiology of Aging. Conference: 14th International Athens/Springfield Symposium on Advances in Alzheimer Therapy. Greece. 39 (Supplement 1):S8-S9.
Lautner R et al., (2017) Preclinical effects of APOE epsilon4 on cerebrospinal fluid Abeta42 concentrations. Alzheimers Res. Ther.; 9:87 (p. 1-7).
Lewczuk P. et al., (2017) Non-phosphorylated tau as a potential biomarker of Alzheimer's disease: analytical and diagnostic characterization. J. Alzheimers Dis.; 55:159-170.
Lim YY et al., (2018) Association of beta-amyloid and apolipoprotein E epsilon4 with memory decline in preclinical Alzheimer disease. JAMA Neurol.; 75:488-494.
Lopez Lopez C et al., (2017) The Alzheimer's Prevention Initiative Generation Program: Evaluating CNP520 Efficacy in the Prevention of Alzheimer's Disease. J. Prey. Alzheimers Dis.; 4(4):242-246.
Lopez Lopez C et al., (2017) Rationale for CNP520 Dose Selection for the Pivotal Clinical Program in Preclinical Ad. Slides presented at: Alzheimer's Association International Conference; Jul. 16-20, 2017; London, UK.
Lopez Lopez C et al., (2017) Rationale for CNP520 Dose Selection for the Pivotal Clinical Program in Preclinical Ad. Alzheimer's & Dementia: The Journal of the Alzheimer's Association; 13(7):P601-P602.
Lopez Lopez C et al., (2017) Evaluating CNP520 efficacy in Preclinical Alzheimer's disease. Journal of Prevention of Alzheimer's Disease; 4(4):291.
Mahley RW, Rail Jr SC, (2000) Apolipoprotein E: far more than a lipid transport protein. Annu. Rev. Genomics Hum. Genet.; 1:507-537.
Maloney JA et al., (2014) Molecular mechanisms of Alzheimer disease protection by the A673T allele of amyloid precursor protein. J. Biol. Chem.; 289:30990-31000.
Mattsson N. et al., (2016) Cerebrospinal fluid tau, neurogranin, and neurofilament light Alzheimer's disease. EMBO Mol. Med., 8:1184-1196.
Mawuenyega KG et al., (2010) Decreased clearance of CNS beta-amyloid in alzheimer's disease. Science; 330:1774 (pp. 1-4).
McEvoy LK, Brewer JB, (2012) Biomarkers for the clinical evaluation of the cognitively impaired elderly: amyloid is not enough. Imaging Med.; 4(3):343-357.
Neumann U, et al., (2016) Preclinical Pharmacology of BACE Inhibitor CNP520. Poster presented at: Alzheimer's Association International Conference; Jul. 24-28, 2016; Toronto, Canada.
Neumann U, et al., (2016) Preclinical Pharmacology of BACE Inhibitor CNP520. Alzheimer's & Dementia: The Journal of the Alzheimer's Association; 12(7):P433-P434.
Neumann U et al., (2017) Effect of BACE inhibition on neuroinflammation, neurodegeneration and neuronal network alterations in app-transgenic mouse models. Slides presented at: 13th International Conference on Alzheimer's and Parkinson's Diseases, AD/PD Mar. 29-Apr. 2, 2017; Vienna, Austria.

(56) References Cited

OTHER PUBLICATIONS

Neumann U et al., (2017) Effect of BACE inhibition on neuroinflammation, neurodegeneration and neuronal network alterations in app-transgenic mouse models. Neurodegenerative Diseases. Conference: 13th International Conference on Alzheimer's and Parkinson's Diseases, AD/PD 2017. Austria; 17(Supplement 1):33.
Nunes PV et al., (2008) CAMcog as a screening tool for diagnosis of mild cognitive impairment and dementia in a Brazilian clinical sample of moderate to high education. Int. J. Geriatr. Psychiatry; 23:1127-1133.
Okamura N. et al., (2014) Tau PET imaging in Alzheimer's disease. Curr. Neurol. Neurosci. Rep.; 14:500 (p. 1-7).
Peila R et al., (2002) Type 2 diabetes, APOE gene, and the risk for dementia and related pathologies: The Honolulu-Asia Aging Study. Diabetes; 51:1256-1262. 1171.
Qian J et al., (2017) APOE-related risk of mild cognitive impairment and dementia for prevention trials: An analysis of four cohorts. PLoS Med.;14:e1002254 (pp. 1-27).
Quiroz YT et al., (2017) Cognitive vulnerabilities in presenilin-1 E280A mutation carrying children from the world's largest autosomal dominant Alzheimer's disease kindred. Alzheimer's and Dementia. Conference: Alzheimer's Association International Conference, AAIC Jul. 16-20, 2017. London, United Kingdom. 1(7):P225-P226.
Raber J et al., (2004) ApoE genotype accounts for the vast majority of AD risk and AD pathology. Neurobiol. Aging; 25:641-650.
Reiman EM et al., (1996) Preclinical evidence of Alzheimer's disease in persons homozygous for the epsilon 4 allele apolipoprotein E. N. Engl. J. Med.; 334(12):752-758. for.
Reiman EM et al., (2001) Declining brain activity in cognitively normal apolipoprotein E epsilon 4 heterozygotes: A foundation for using positron emission tomography to efficiently test treatments to prevent Alzheimer's disease. Proc. Natl. Acad. Sci. U S A; 98(6):3334-3339.
Reiman EM et al., (2009) Fibrillar amyloid-beta burden in cognitively normal people at 3 levels of genetic risk for Alzheimer's disease. Proc. Natl. Acad. Sci. U S A; 106(16):6820-6825.
Reiman EM et al., (2010) Alzheimer's prevention initiative: a proposal to evaluate presymptomatic treatments as quickly as possible. Biomark. Med.; 4(1):3-14.
Reiman EM et al.. (2011) Alzheimer's Prevention Initiative: a plan to accelerate the evaluation of presymptomatic treatments. J. Alzheimers Dis.; 26(Suppl 3):321-329.
Reiman EM et al., (2016) CAP—advancing the evaluation of preclinical Alzheimer disease treatments. Nat. Rev. Neurol.; 12(1):56-61.
Reiman EM et al., (2017) Sample sizes for 24-month Alzheimer's prevention trials using biomarker endpoints in cognitively unimpaired amyloid positive adults. Alzheimer's and Dementia. Conference: Alzheimer's Association International Conference, AAIC Jul. 16-20, 2017. London, United Kingdom. 13(7):P36-P37.
Reiman EN et al., (2017) Sample sizes for 24-month Alzheimer's prevention trials using biomarker endpoints in cognitively unimpaired amyloidpositive adults. Alzheimer's and Dementia. Conference: Alzheimer's Association International Conference, AAIC Jul. 16-20, 2017. London, United Kingdom; 13(7):P1453-P1454.
Reitz C, Mayeux R., (2014) Alzheimer disease: epidemiology, diagnostic criteria, risk factors and biomarkers. Biochem. Pharmacol.; 88:640-651.
Riviere ME, (2017) Generation program with Bace inhibitor CNP520 in cognitively unimpaired APOE4 carriers at risk for the onset of clinical symptoms of AD. Slides presented at: European Alzheimer's Disease Consortium Meeting; Apr. 27-28, 2017; Bucharest, Romania.
Riviere ME et al., (2017) BACE Inhibitor CNP520 proposed for the Alzheimer's Prevention Initiative Generation Study 1; Poster presented at: Mechanisms, Clinical Strategies, and Promising Treatments of Neurodegenerative Diseases. 13th International Conference AD/PDTM Vienna, Austria, Mar. 29 to Apr. 2, 2017.
Riviere ME et al., (2017) BACE Inhibitor CNP520 proposed for the Alzheimer's Prevention Initiative Generation Study; Neurodegener. Dis.; 17(suppl 1):841.
Sabbagh MN et al., (2015) Florbetapir PET, FDG PET, and MRI in Down syndrome individuals with and without Alzheimer's dementia. Alzheimers Dement.; 11(8):994-1004.
Schelle J et al., (2017) Prevention of cerebral amyloid angiopathy in a mouse model of hereditary cerebral hemorrage with amyloidosis-dutch type. Poster presented at: Alzheimer's Association International Conference, AAIC Jul. 16-20, 2017. London, United Kingdom.
Schelle J et al., (2017) Prevention of cerebral amyloid angiopathy in a mouse model of hereditary cerebral hemorrage with amyloidosis-dutch type. Alzheimer's and Dementia. Conference: Alzheimer's Association International Conference, Aaic Jul. 16-20, 2017. United Kingdom; 13(7):P626-P627.
Schelle J et al., (2017) Prevention of tau increase in cerebrospinal fluid of APP transgenic mice suggests downstream effect of BACE1 inhibition. Alzheimers Dement.; 13:701-709.
Scheltens p. et al., (2016) Alzheimer's disease. Lancet; 388:505-517.
Schuff N. et al., (2009) MRI of hippocampal volume loss in early Alzheimer's disease in relation to ApoE genotype and biomarkers. Brain; 132:1067-1077.
Selkoe DJ, Hardy J, (2016) The amyloid hypothesis of Alzheimer's disease at 25 years. EMBO Mol. Med.; 8:595-608.
Shaw LM et al., (2009) Cerebrospinal fluid biomarker signature in Alzheimer's disease neuroimaging initiative subjects. Ann. Neural.; 65:403-413.
Silverberg NB et al., (2011) Assessment of cognition in early dementia. Alzheimers Dement.; 7:e60-e76.
Small GW et al., (2000) Cerebral metabolic and cognitive decline in persons at genetic risk for Alzheimer's disease. Proc. Natl. Acad. Sci. U S A; 97:6037-6042.
Tariot PN et al., (2016) The Alzheimer's Prevention Initiative Generation Study: A Preclinical Trial in APOE4 Homozygotes. Poster presented at: 55th Annual Meeting of the American College of Neuropsychopharmacology, ACNP Dec. 4-8, 2016. Hollywood, FL, United States.
Tariot PN et al., (2016) The Alzheimer's Prevention Initiative Generation Study: A Preclinical Trial in APOE4 Homozygotes. Neuropsychopharmacology. Conference: 55th Annual Meeting of the American College of Neuropsychopharmacology, ACNP Dec. 4-8, 2016. Hollywood, FL, United States; 41(Supplement 1):S139.
Tariot P. et al., (2016) What are we willing to accept for preventing Alzheimer's disease?—Investigators' reply. Lancet Neural.; 15(7):660-661.
Tariot PN et al., (2017) Rationale, Design and Progress of Alzheimer's Prevention Initiative (API) Trials. Journal of Prevention of Alzheimer's Disease; 4(4):399.
Tariot PN et al., (2017) The Alzheimer's Prevention Initiative (API) Generation Program: Evaluating CNP520 Efficacy in Preclinical Alzheimer's Disease. Poster presented at: 56th Annual Meeting of the American College of Neuropsychopharmacology, ACNP 2017. United States; 43(Supplement 1):S143-S144.
Tariot PN, (2017) The Alzheimer's Prevention Initiative Generation Study: A Preclinical Trial in APOE4 Homozygotes, P2-023. Poster presented at: IPS: The Mental Health Services Conference, Oct. 19-22, 2017, New Orleans, MS, United States.
Tariot PN, (2017) The Alzheimer's Prevention Initiative Generation Study: A Preclinical Trial in APOE4 Homozygotes, Abstract 2040. IPS: The Mental Health Services Conference, Oct. 19-22, 2017, New Orleans, MS, United States (last accessed Jan. 22, 2017 at https://s7.goeshow.com/apa/ips/2017/form_print_preview.cfm?abstract_key=7AAE4793-5) (2 pages).
Tariot P., (2017) Alzheimer's prevention: Pipedream or possibility? Biological Psychiatry. Conference: 72nd Annual Scientific Convention and Meeting of the Society of Biological Psychiatry, Sobp 2017. United States; 81(10 Supplement 1):S1-S2.
Thal DR et al., (2008) Cerebral amyloid angiopathy and its relationship to Alzheimer's disease. Acta Neuropathol.; 115:599-609.

(56) References Cited

OTHER PUBLICATIONS

Thal DR et al., (2009) Capillary cerebral amyloid angiopathy is associated with vessel occlusion and cerebral blood flow disturbances. Neurobiol. Aging; 30:1936-1948.

Thal DR et al., (2010) Capillary cerebral amyloid angiopathy identifies a distinct APOE ε4-associated subtype of sporadic Alzheimer's disease. Acta Neuropathol.; 120:169-183.

Ufer M et al., (2016) Results from a first-in-human study with the bace inhibitor CNP520. Alzheimer's & Dementia: the Journal of the Alzheimer's Association; 12(7):P200.

Ufer M et al., (2016) Results from a first-in-human study with the bace inhibitor CNP520. Slides presented at: Association International Conference; Jul. 22-28, 2016; Toronto, Canada. Alzheimer's.

Ufer M et al., (2017) Results from a three-month study in healthy subjects a60 years of age with the BACE1 inhibitor CNP520. Alzheimer's & Dementia: the Journal of the Alzheimer's Association; 13(7):P256.

Ufer M et al., (2017) Results from a three-month study in healthy subjects aso years of age with the BACE1 inhibitor CNP520. Poster presented at: Alzheimer's Association International Conference; Jul. 16-20, 2017; London, Uk.

Van Cauwenberghe C et al., (2016) the genetic landscape of Alzheimer disease: clinical implications and perspectives. Genet. Med.; 18:421-430.

Vidoni ED et al., (2016) Cerebral β-amyloid angiopathy is associated with earlier dementia onset in Alzheimer's disease. Neurodegener. Dis.; 16:218-224.

Villarreal S et al., (2017) Chronic verubecestat treatment suppresses amyloid accumulation in advanced aged Tg2576-AβPPswemice without inducing microhemorrhage. J. Alzheimer's Dis.; 59:1393-1413.

Vos SJ et al., (2013) Preclinical Alzheimer's disease and its outcome: a longitudinal cohort study. Lancet Neural.; 12:957-965.

Yamada M, (2015) Cerebral Amyloid Angiopathy: Emerging Concepts. J. Stroke; 17(1):17-30.

Yan R, (2016) Stepping closer to treating Alzheimer's disease patients with BACE1 inhibitor drugs. Translational Neurodegeneration; 5:13(pp. 1-11).

Yates PA et al., (2011) Cerebral microhemorrhage and brain (3-amyloid in aging and Alzheimer disease. Neurology; 77:48-54.

Yates PA et al., (2014) Incidence of cerebral microbleeds in preclinical Alzheimer disease. Neurology; 82(14): 1266-1273.

\* cited by examiner

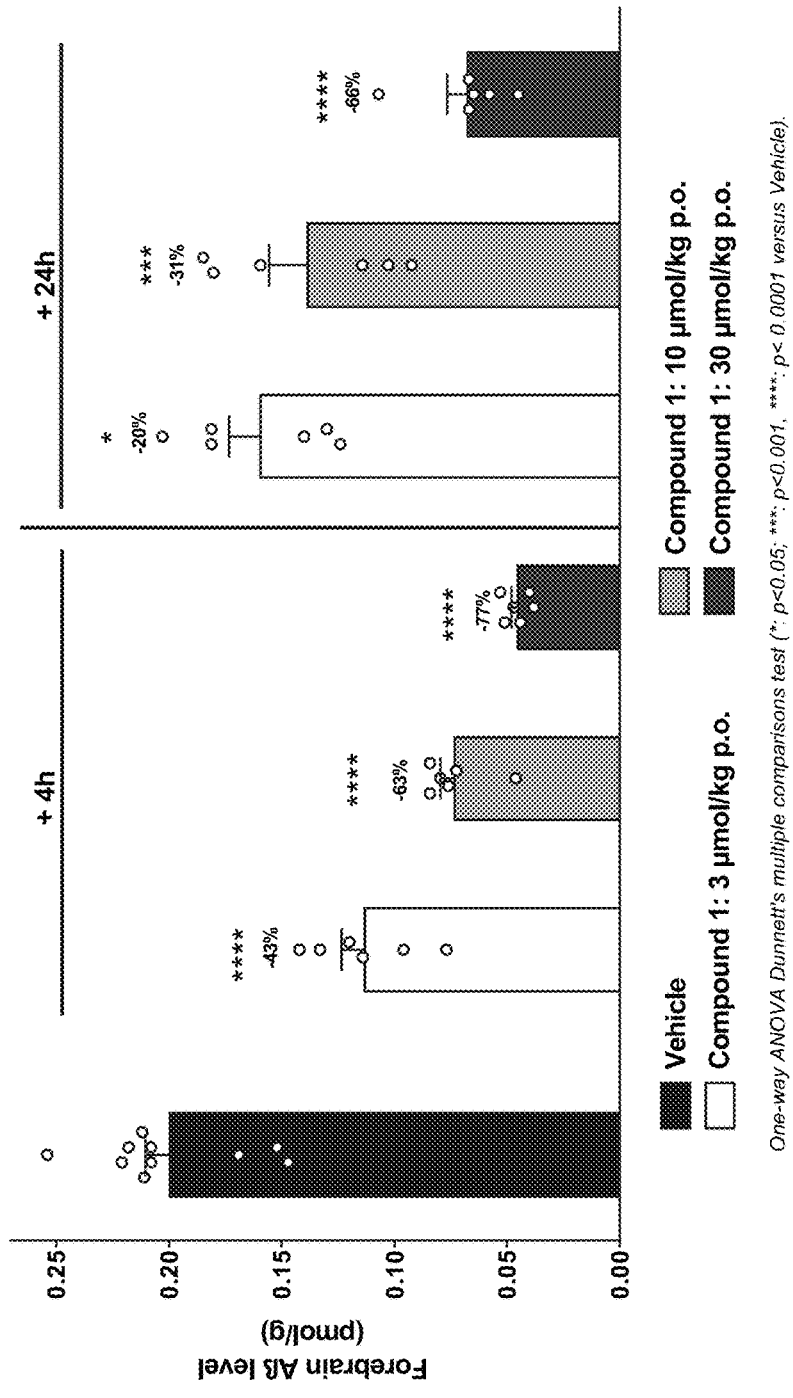
Figure 1: Effect of acute administration of Compound 1 on forebrain Aβ40 levels in APOE4-TR male and female mice (3-5 month-old, Mean ± SEM)

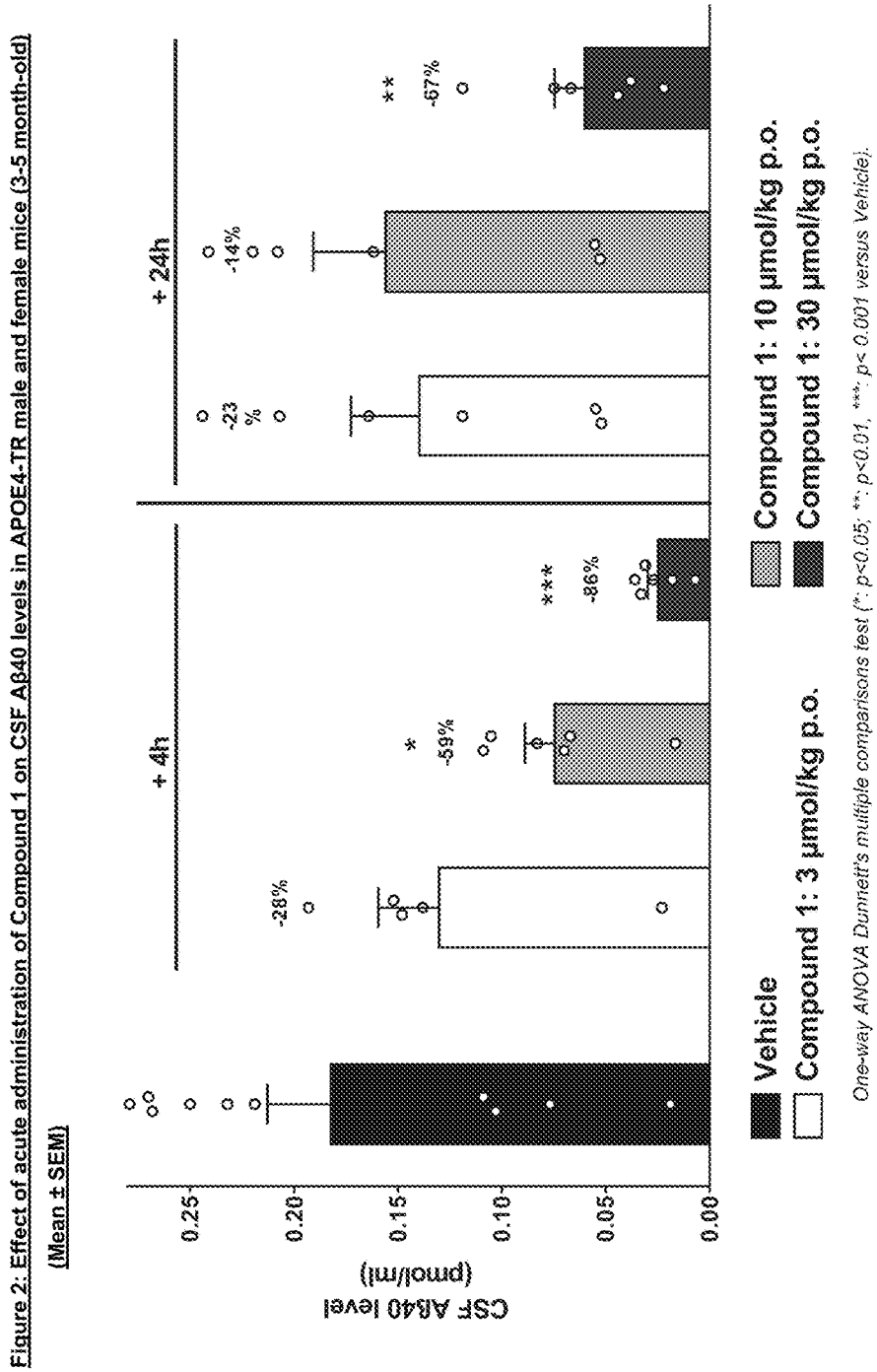
Figure 2: Effect of acute administration of Compound 1 on CSF Aβ40 levels in APOE4-TR male and female mice (3-5 month-old)

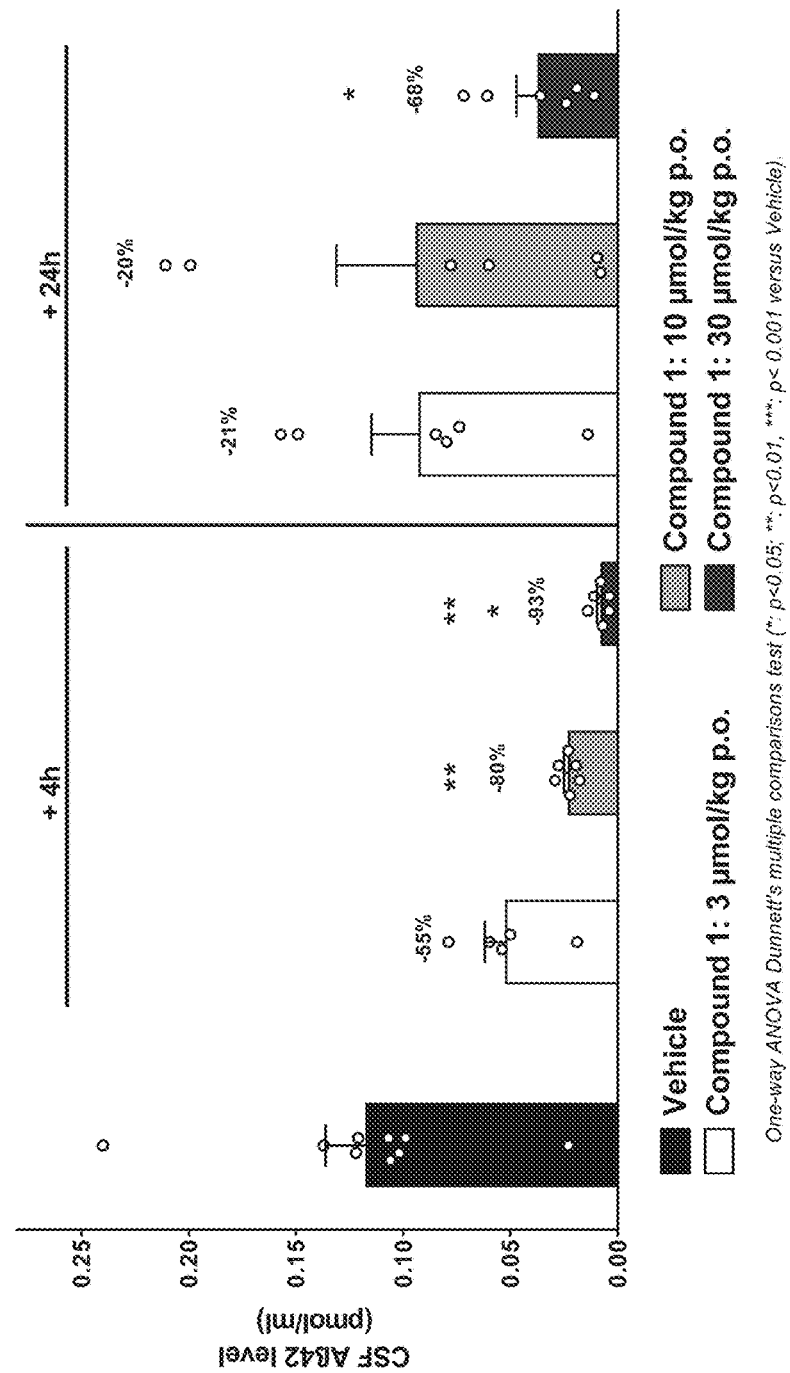

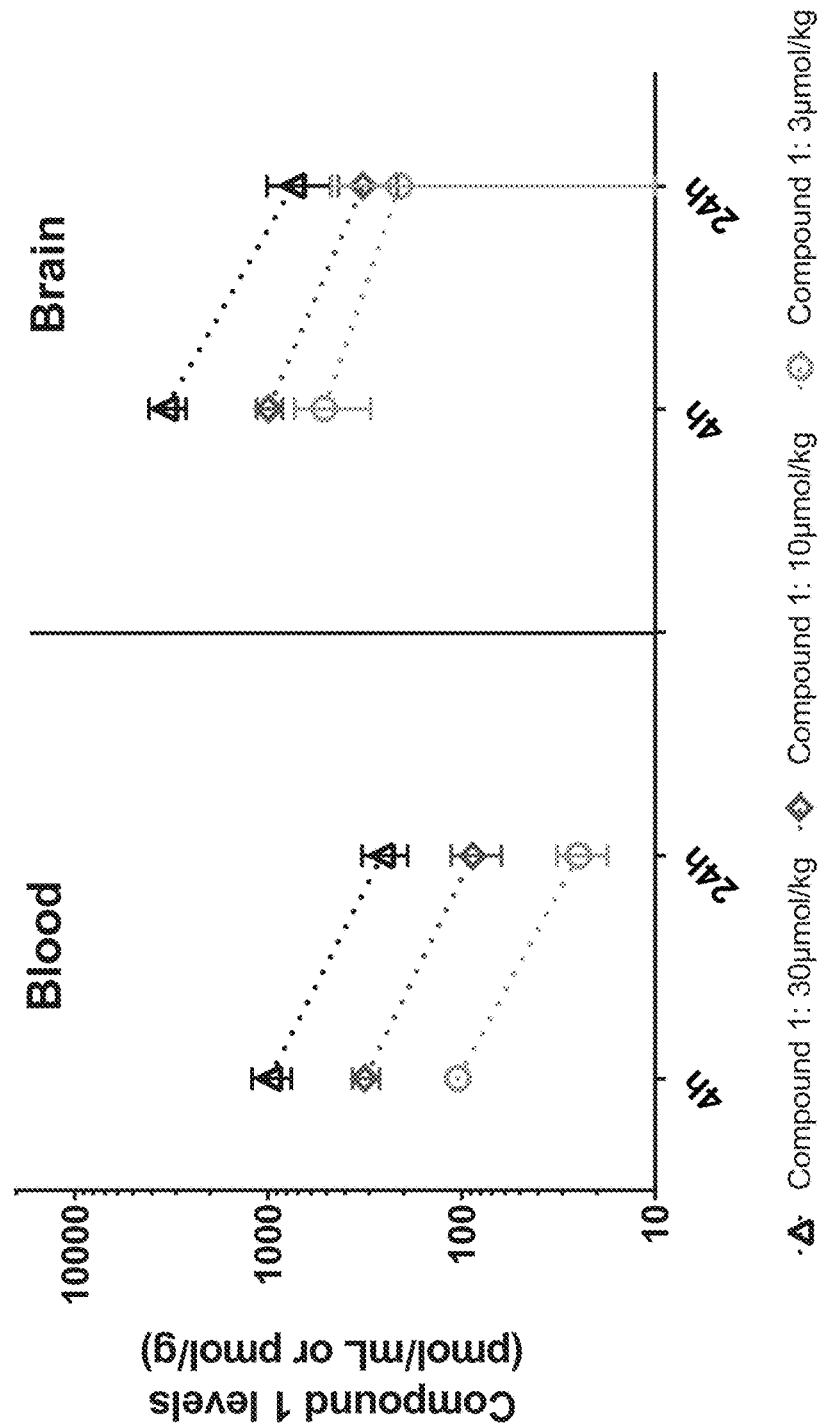
Figure 4: Compound 1 acute exposure in APOE4-TR male and female mice (3-5 month-old, Mean ± SD)

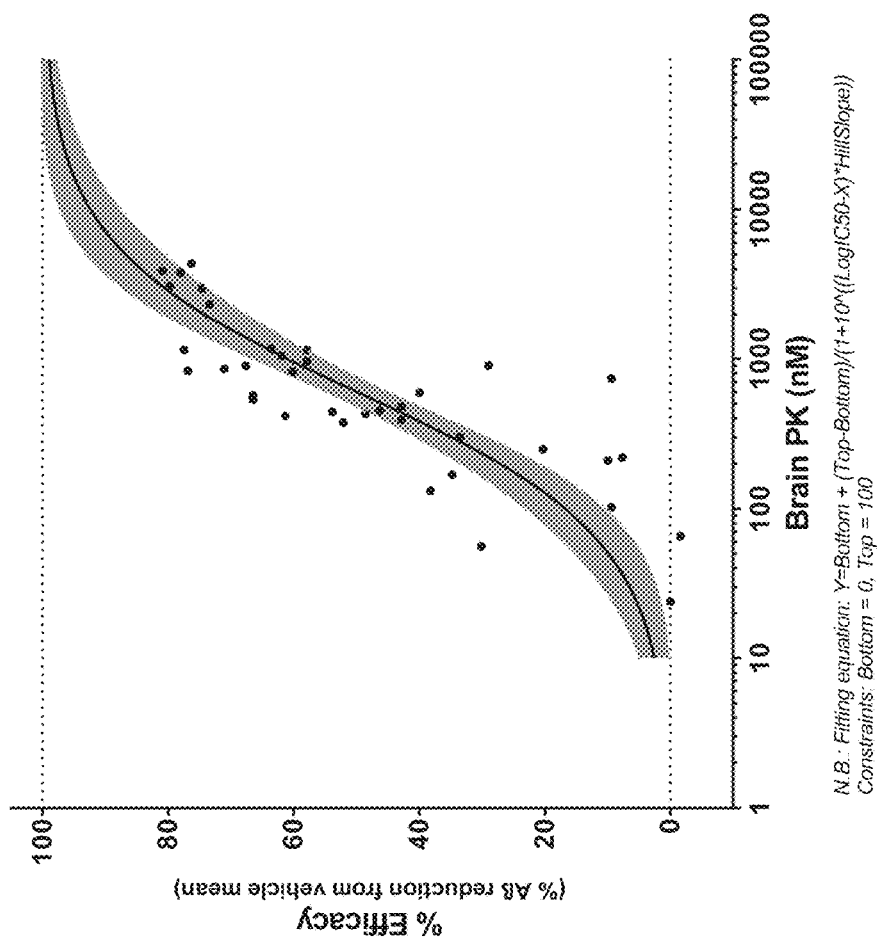
Figure 5: Brain PK/PD relationship (individual data)

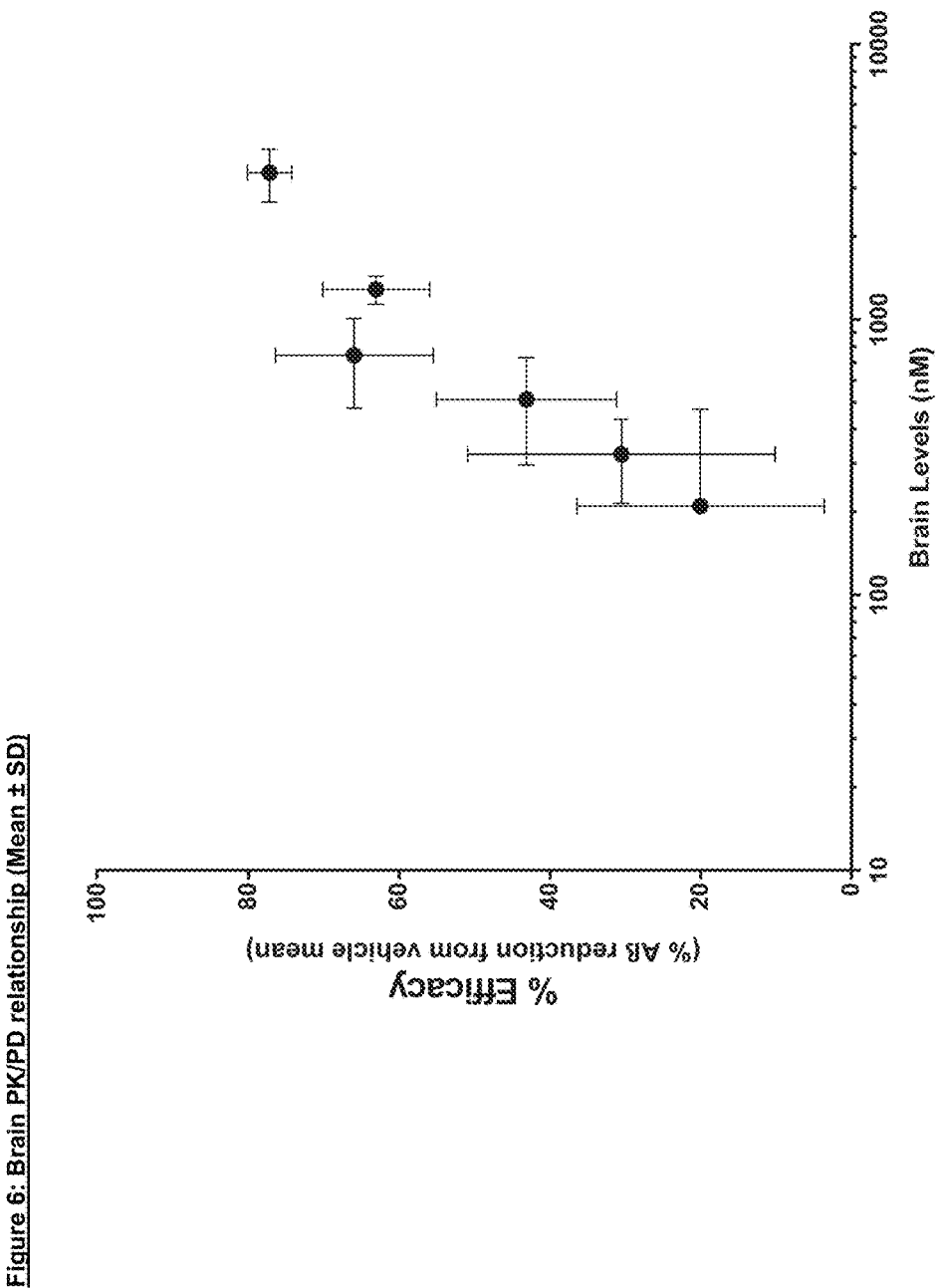
Figure 6: Brain PK/PD relationship (Mean ± SD)

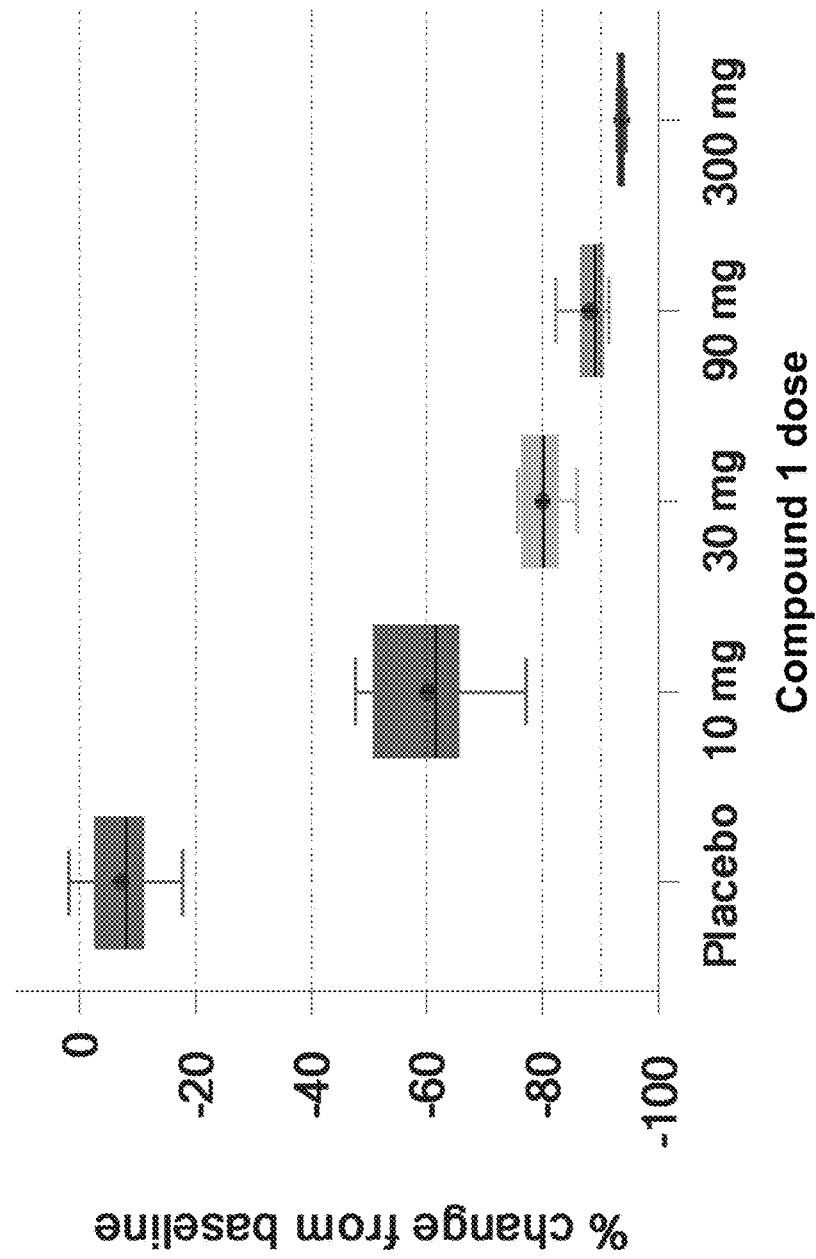
Figure 7: Effect of Compound 1 on CSF Aβ40 levels after two-week exposure in multiple ascending oral dose study in human subjects

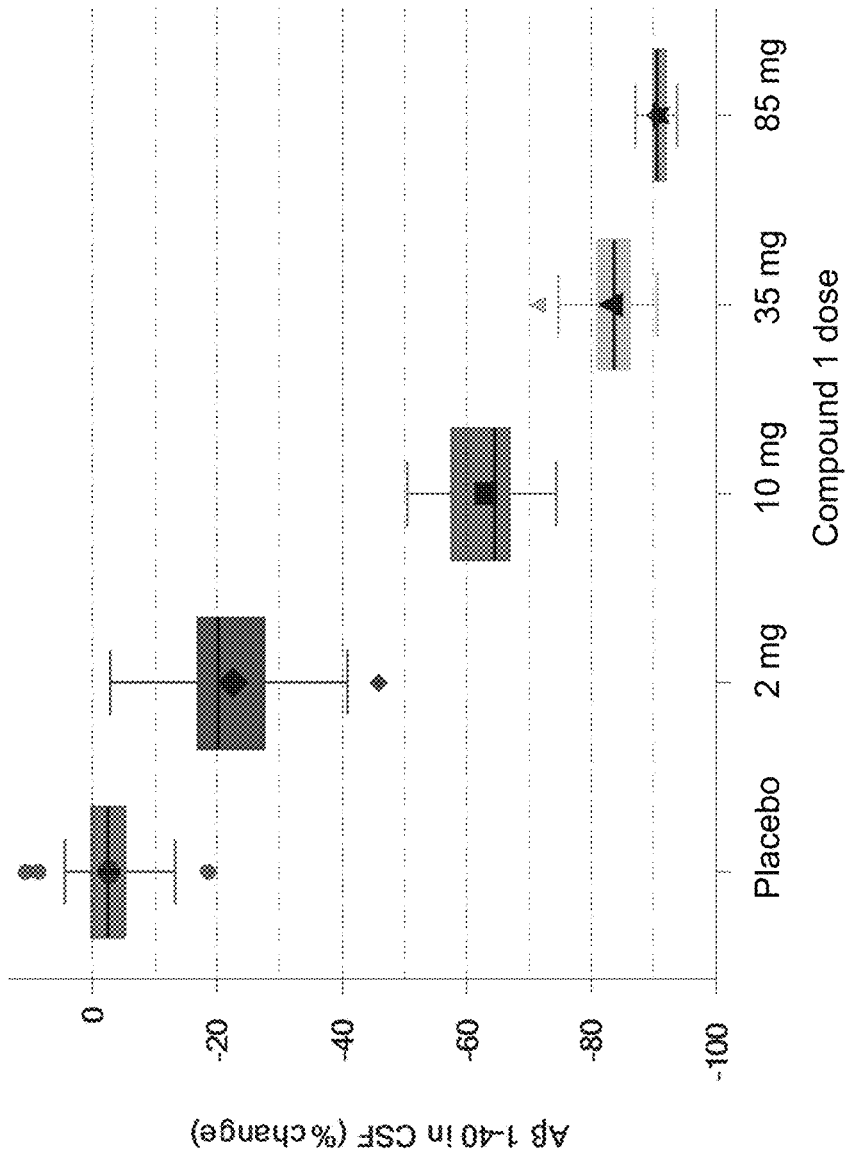
Figure 8: Effect of Compound 1 on CSF Aβ40 levels in human subjects - % change from baseline at 3 months (24 hours post last dose)

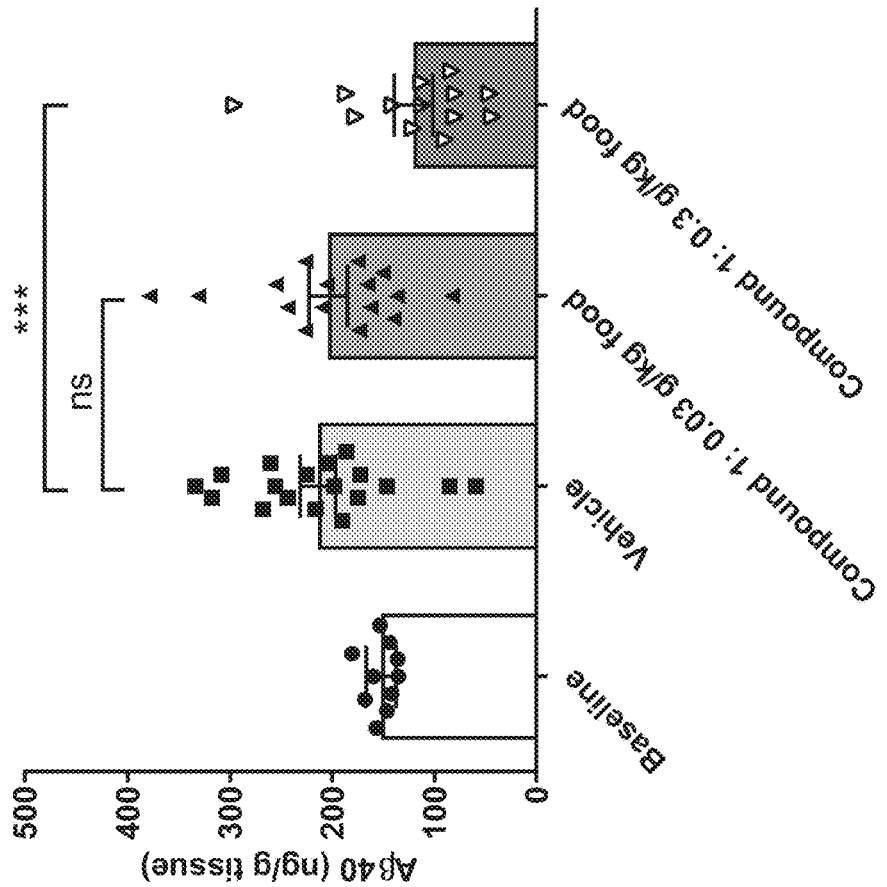
Figure 9: Effect of Compound 1 on Aβ40 in Triton TX-100 extracted aged APP23 brains

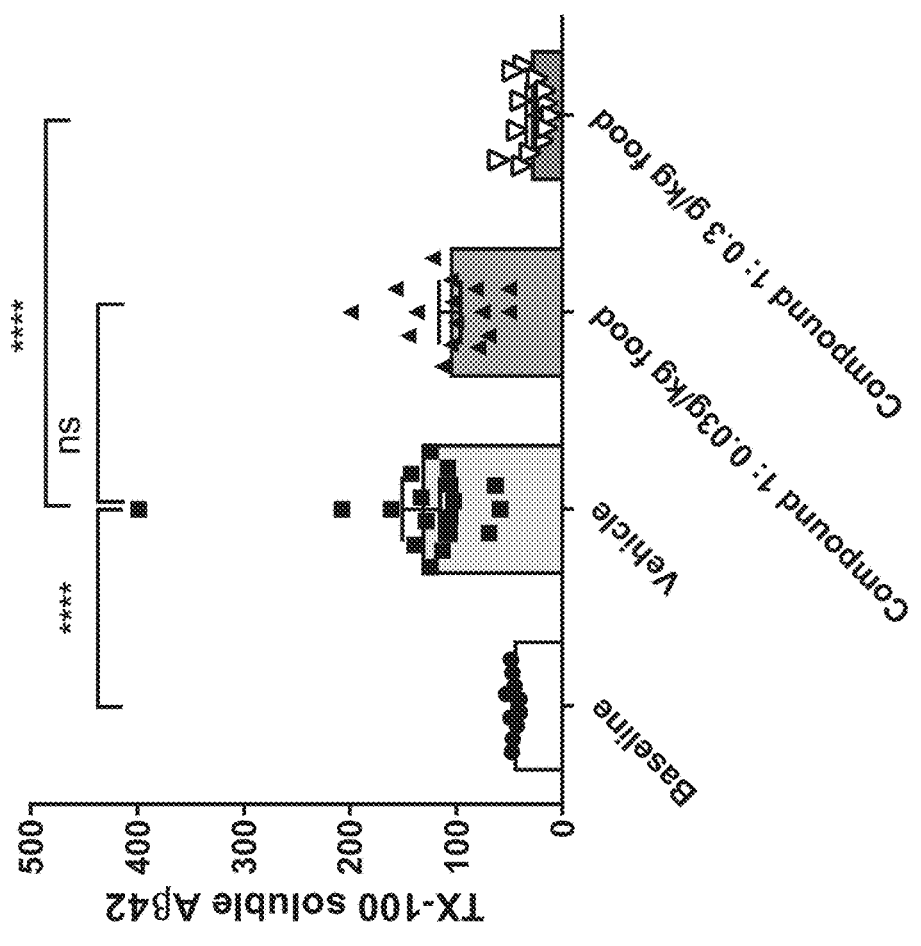
Figure 10: Effect of Compound 1 on Aβ42 in Triton TX-100 extracted aged APP23 brains

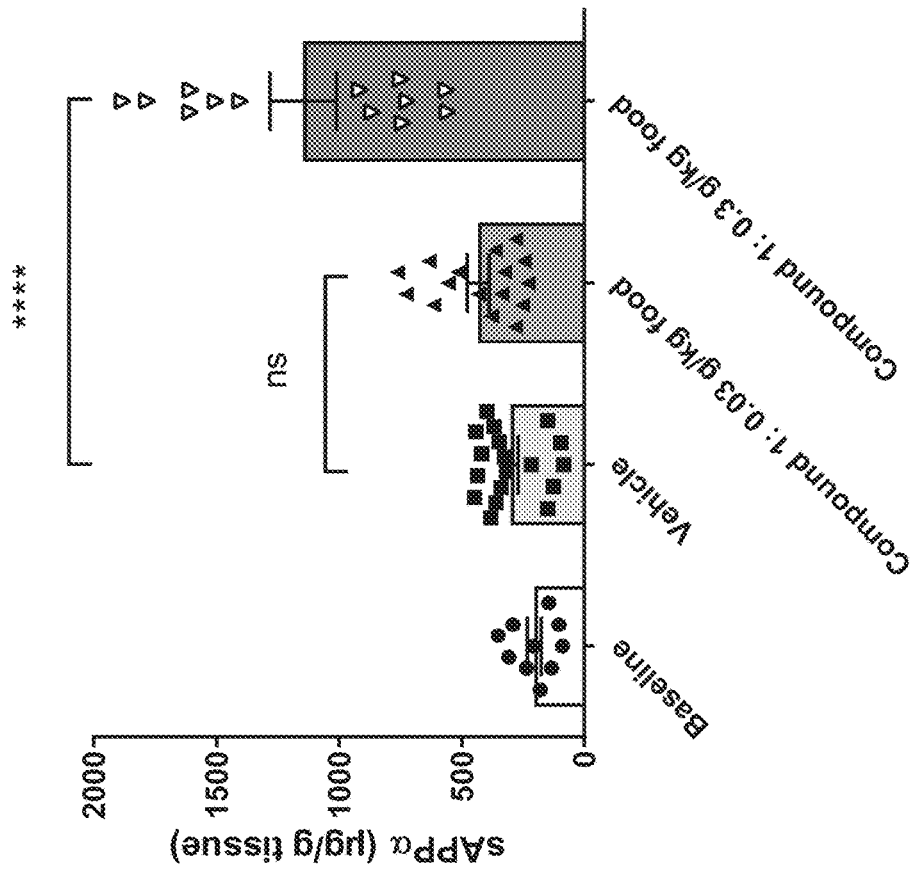
Figure 11: Effect of Compound 1 on sAPPα in Triton TX-100 extracted aged APP23 brains

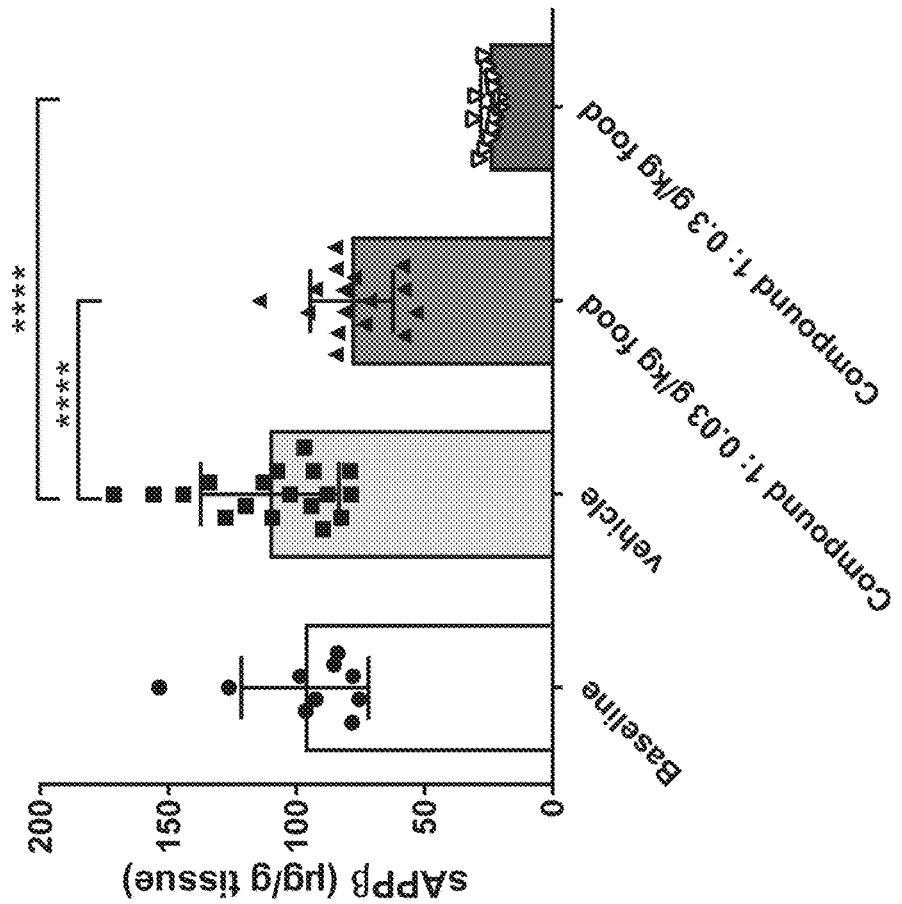
Figure 12: Effect of Compound 1 on sAPPβ (Swe) in Triton TX-100 extracted aged APP23 brains

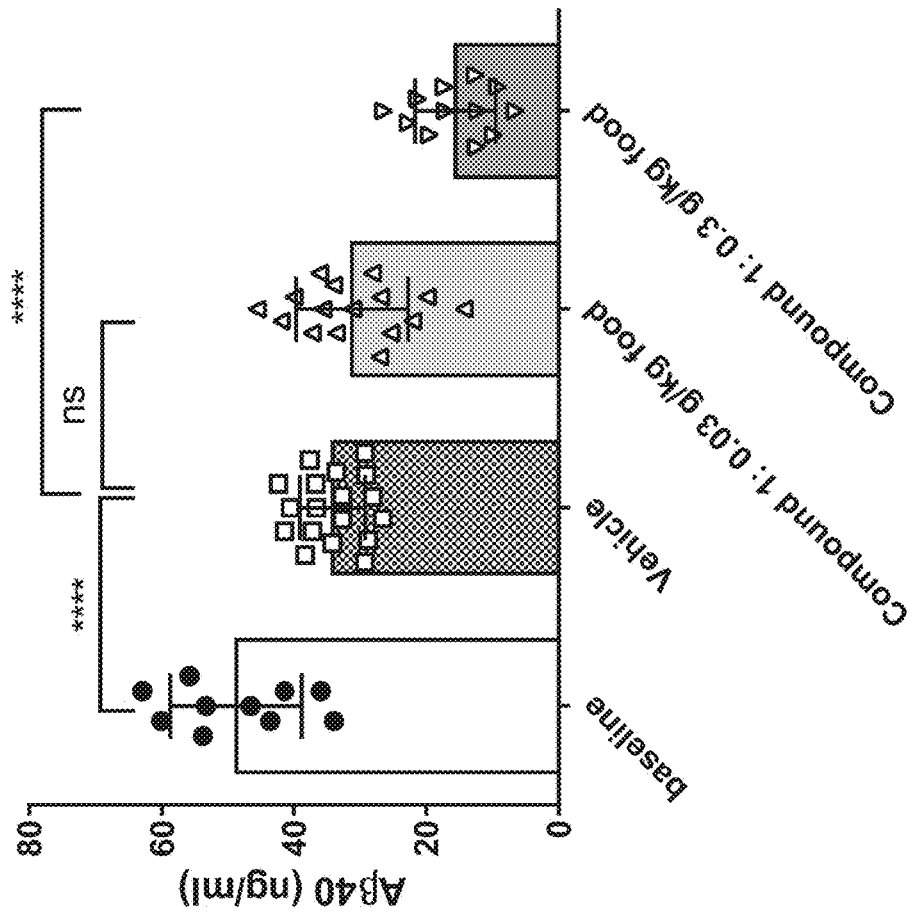
Figure 13: Effect of Compound 1 treatment on Aβ40 in the cerebrospinal fluid of aged APP23 mice

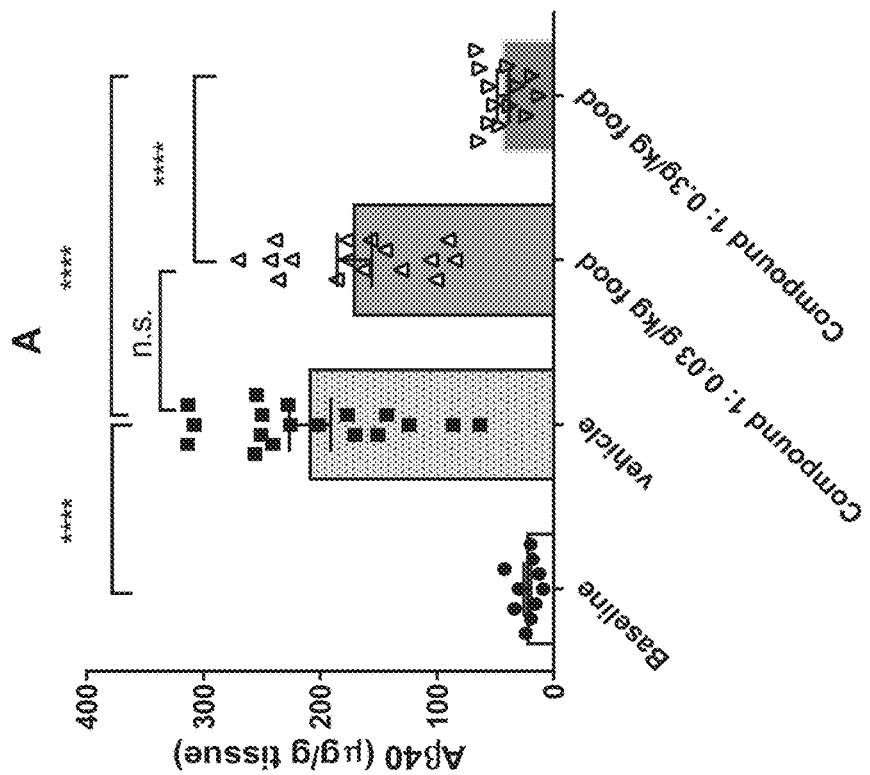
Figure 14: Effect of Compound 1 on formic acid soluble Aβ40 in aged APP23 mice (values are mean ± SEM)

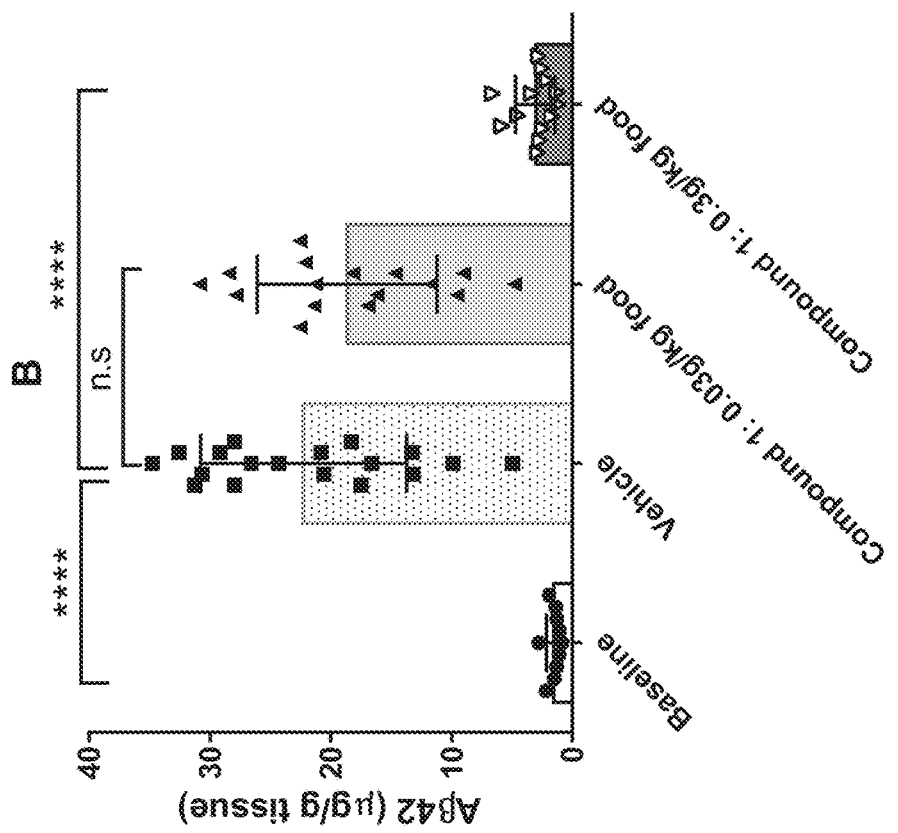
Figure 15: Effect of Compound 1 on formic acid soluble Aβ42 in aged APP23 mice (values are mean ± SEM)

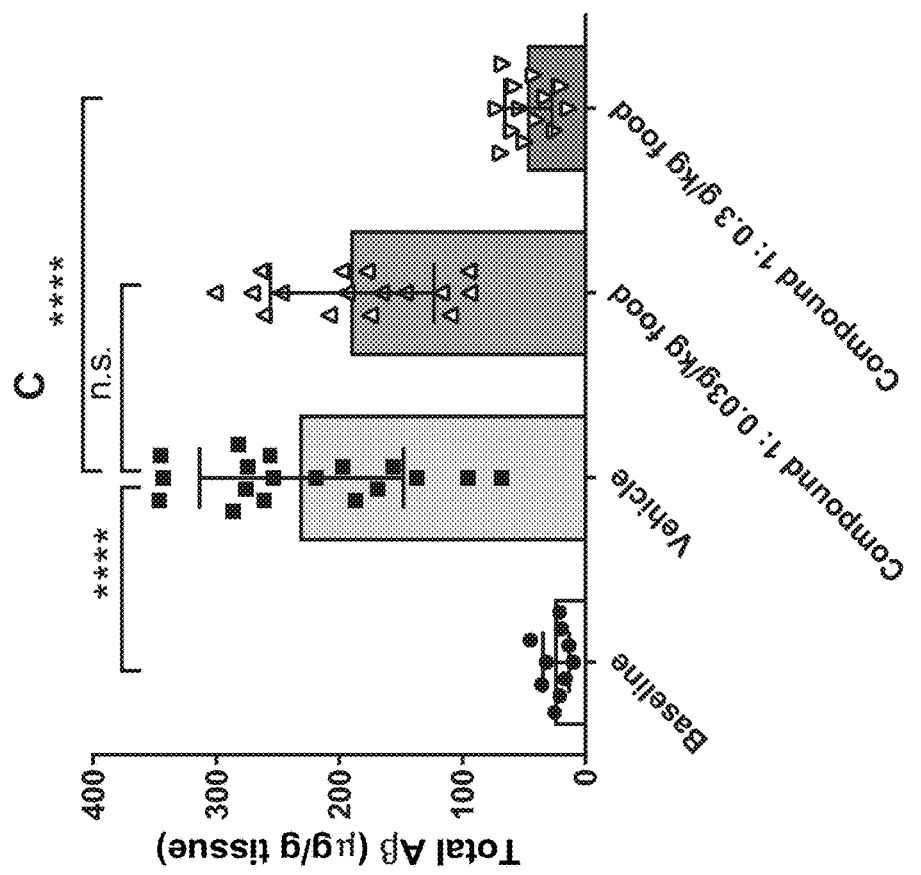
Figure 16: Effect of Compound 1 on formic acid soluble total Aβ (40+42) in aged APP23 mice (values are mean ± SEM)

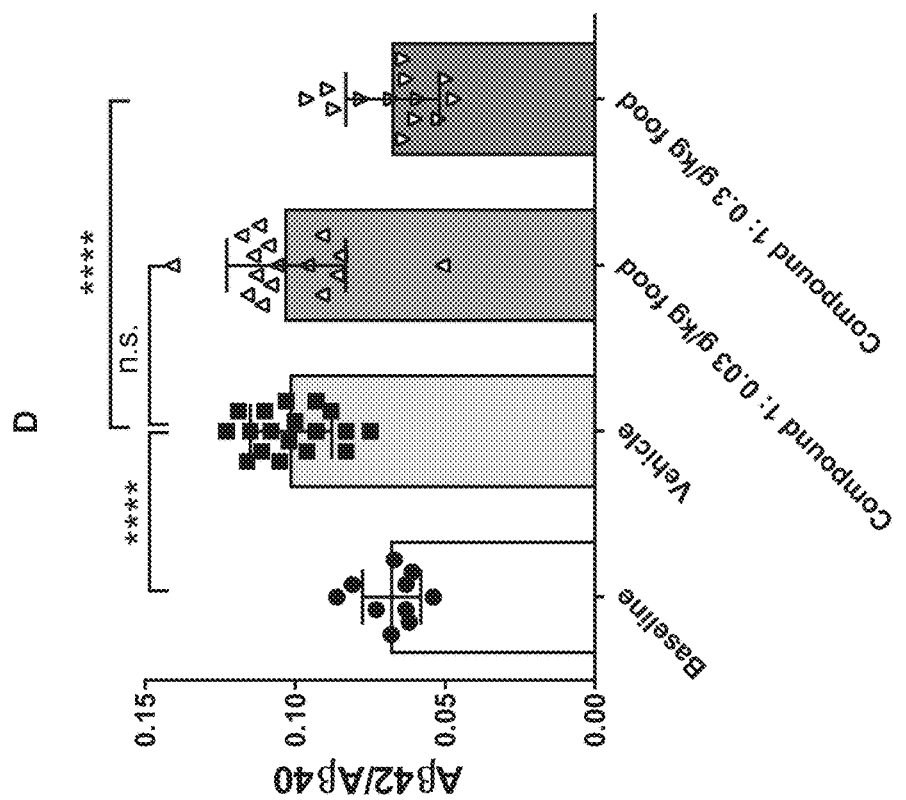
Figure 17: Effect of Compound 1 on formic acid soluble Aβ42/40 ratio in aged APP23 mice (values are mean ± SEM)

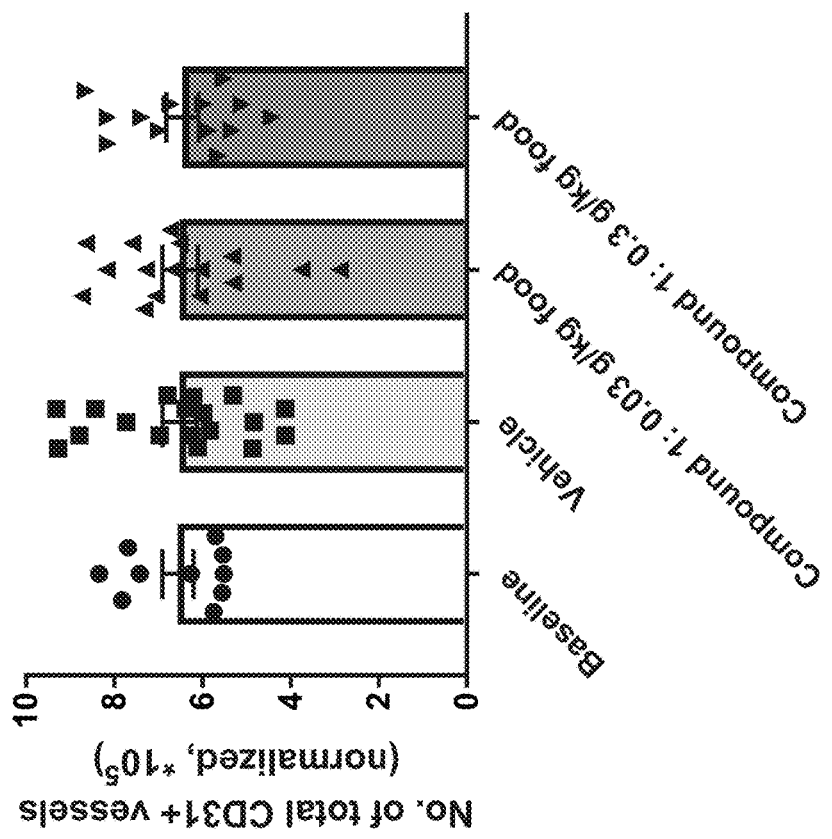
Figure 18: Effect of Compound 1 on number of total CD31+ brain blood vessels in aged APP23 mice (values are mean ± SEM)

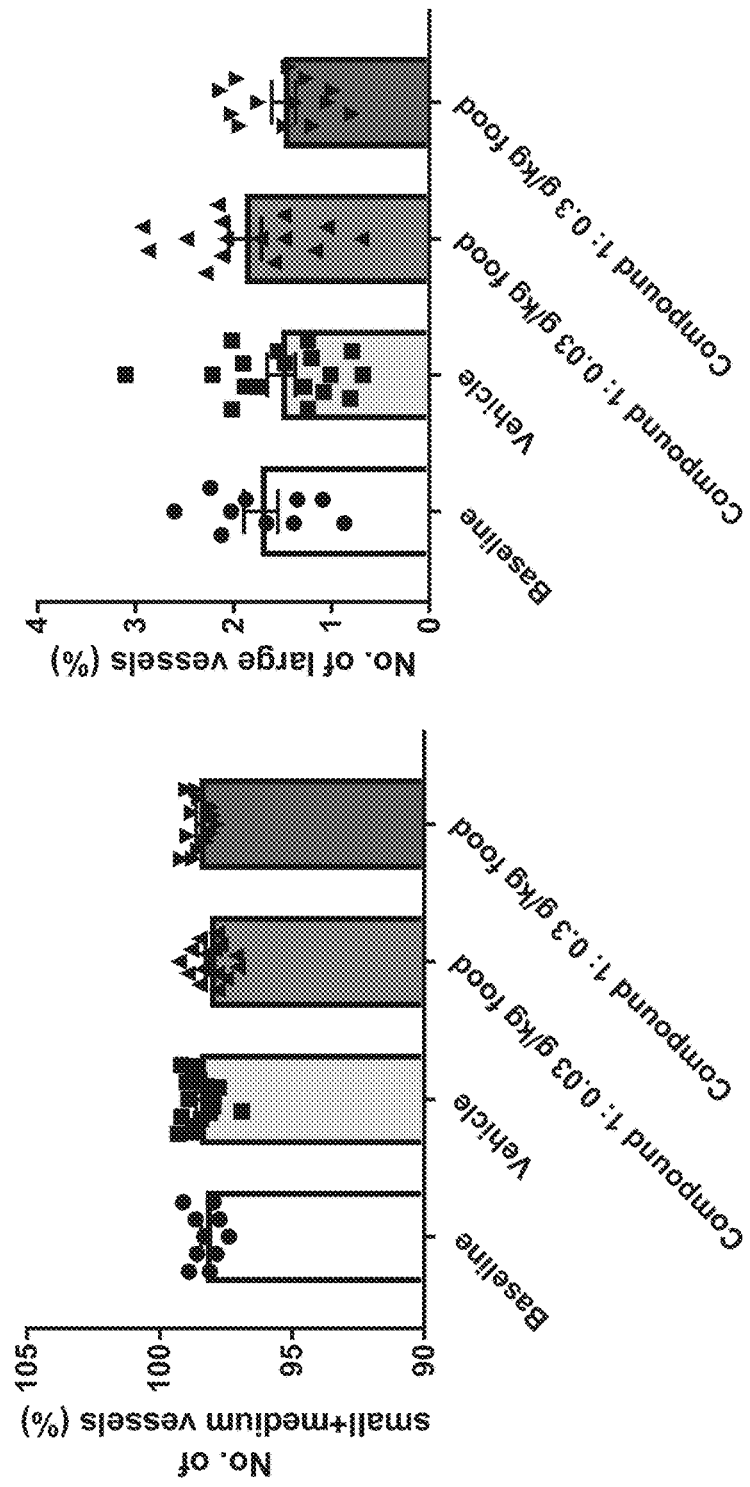
Figure 19: Effect of Compound 1 on number of total small+medium and large CD31+ brain blood vessels in aged APP23 mice (values are mean ± SEM)

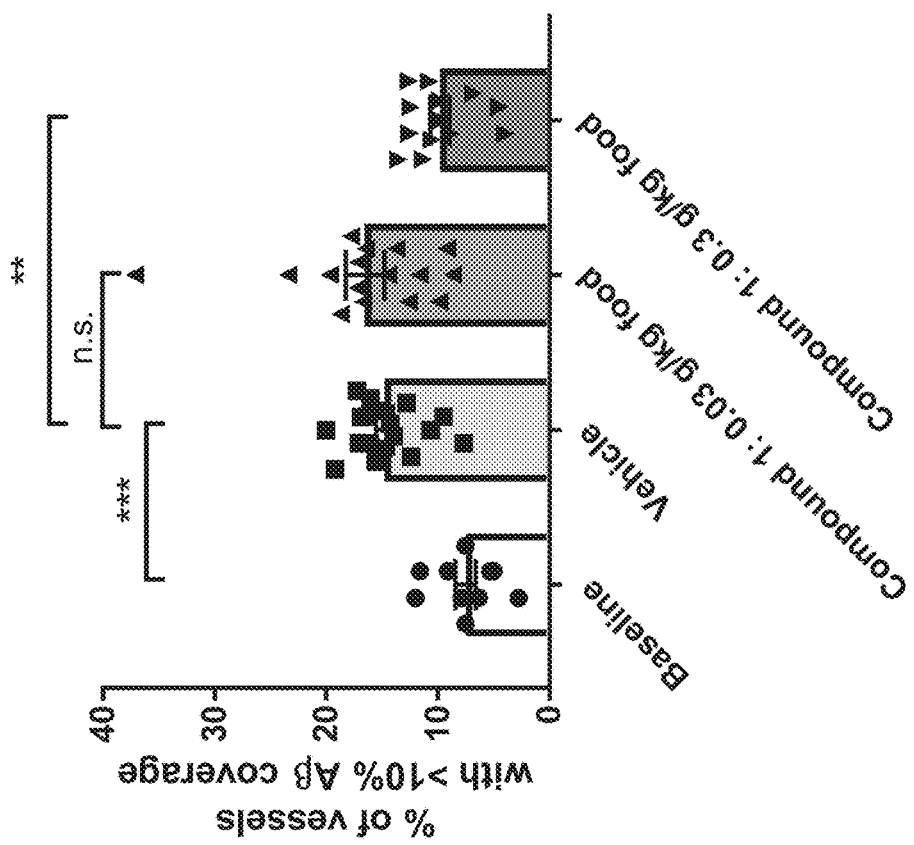
Figure 20: Effect of Compound 1 on % of vessels with >10% Aβ coverage in aged APP23 mice (values are mean ± SEM)

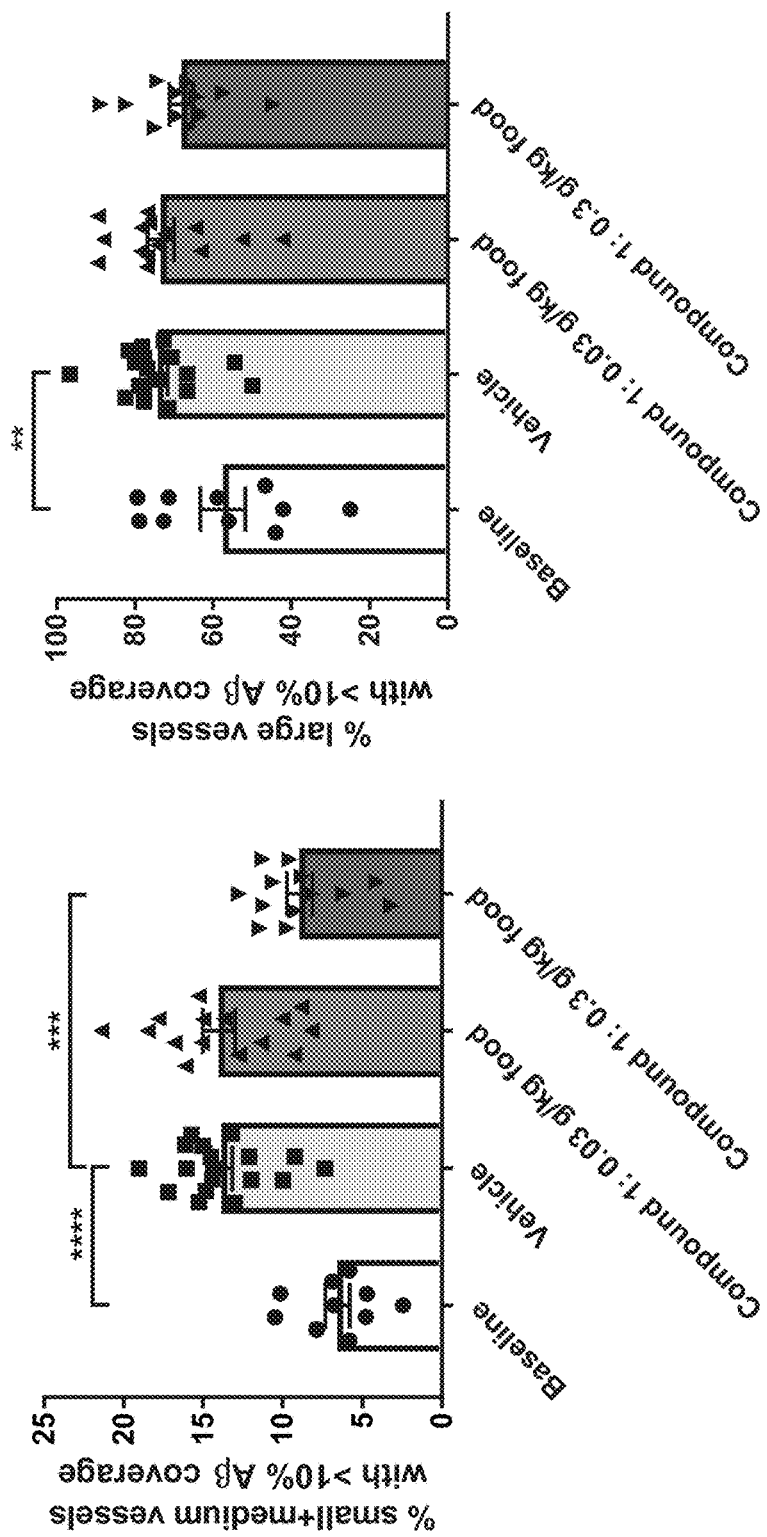
Figure 21: Effect of Compound 1 on % of small+medium and large vessels with >10% Aβ coverage in aged APP23 mice (values are mean ± SEM)

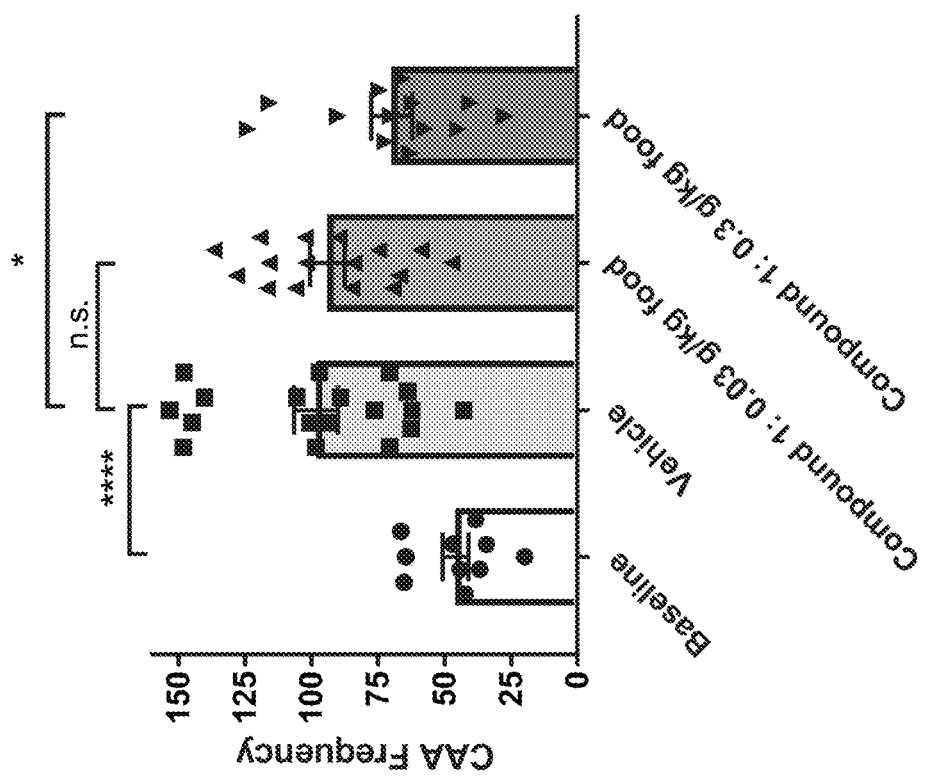
Figure 22: Effect of Compound 1 on CAA frequency (of vessels with >10% Aβ coverage) in aged APP23 mice (values are mean ± SEM)

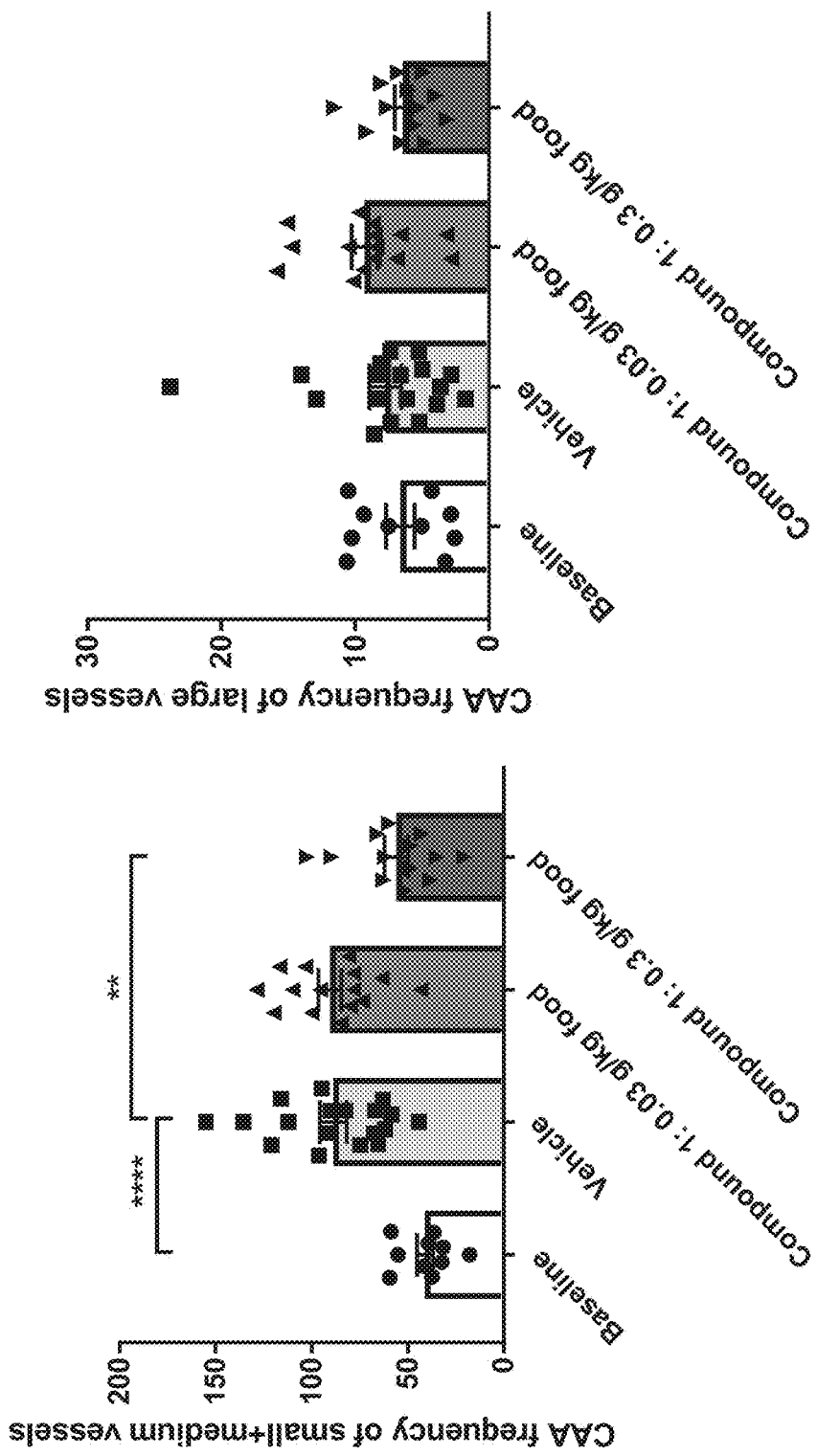
Figure 23: Effect of Compound 1 on CAA frequency (of small+medium and large vessels (of vessels with >10% Aβ coverage) in aged APP23 mice (values are mean ± SEM)

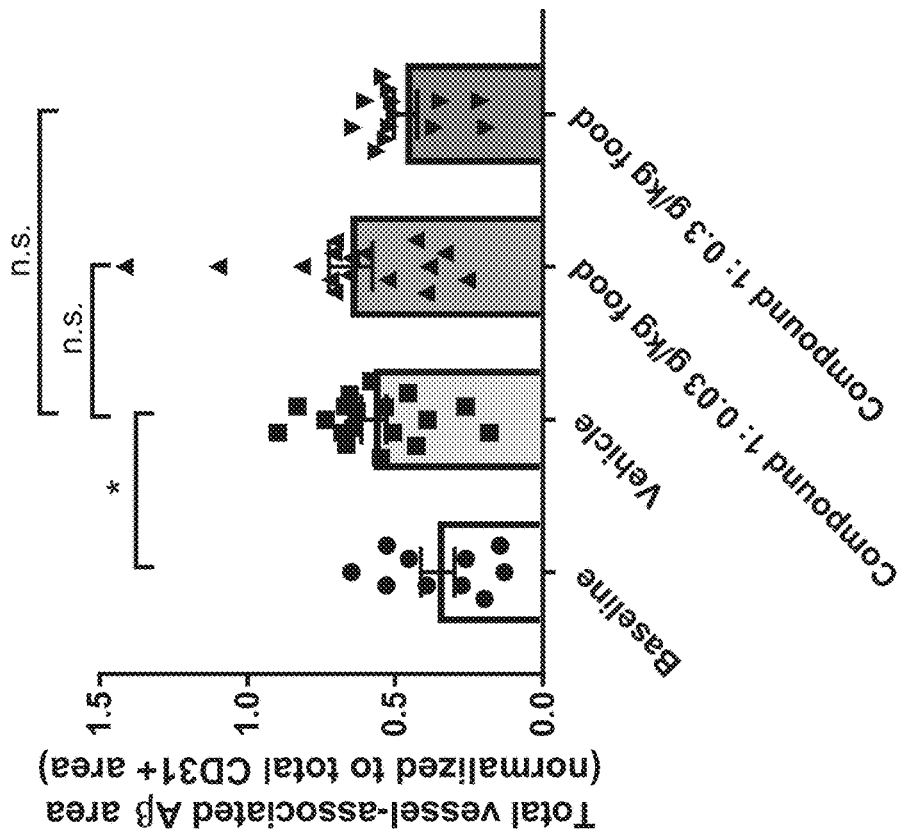
Figure 24: Effect of Compound 1 on total vessel-associated Aβ area in aged APP23 mice (values are mean ± SEM)

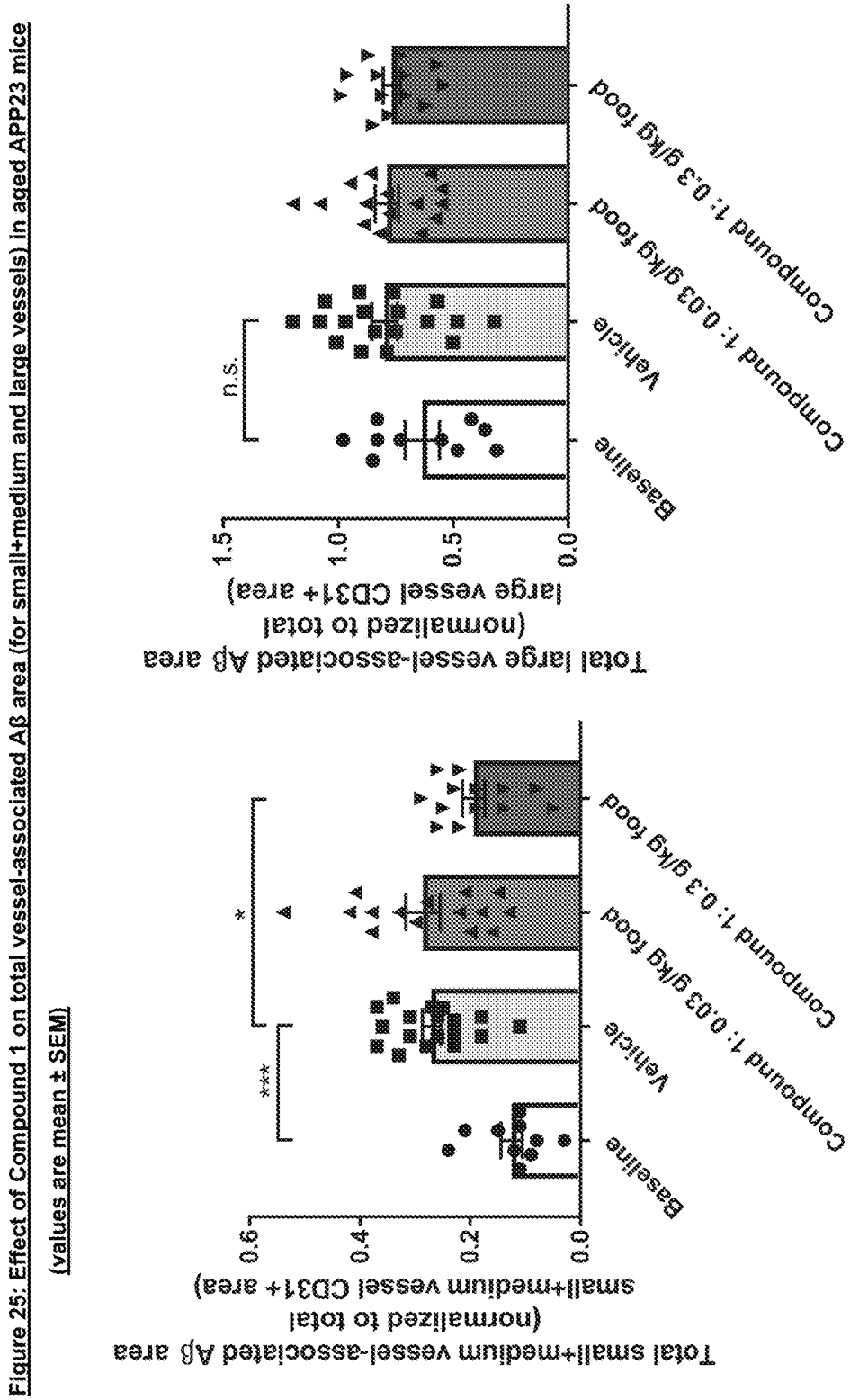
Figure 25: Effect of Compound 1 on total vessel-associated Aβ area (for small+medium and large vessels) in aged APP23 mice (values are mean ± SEM)

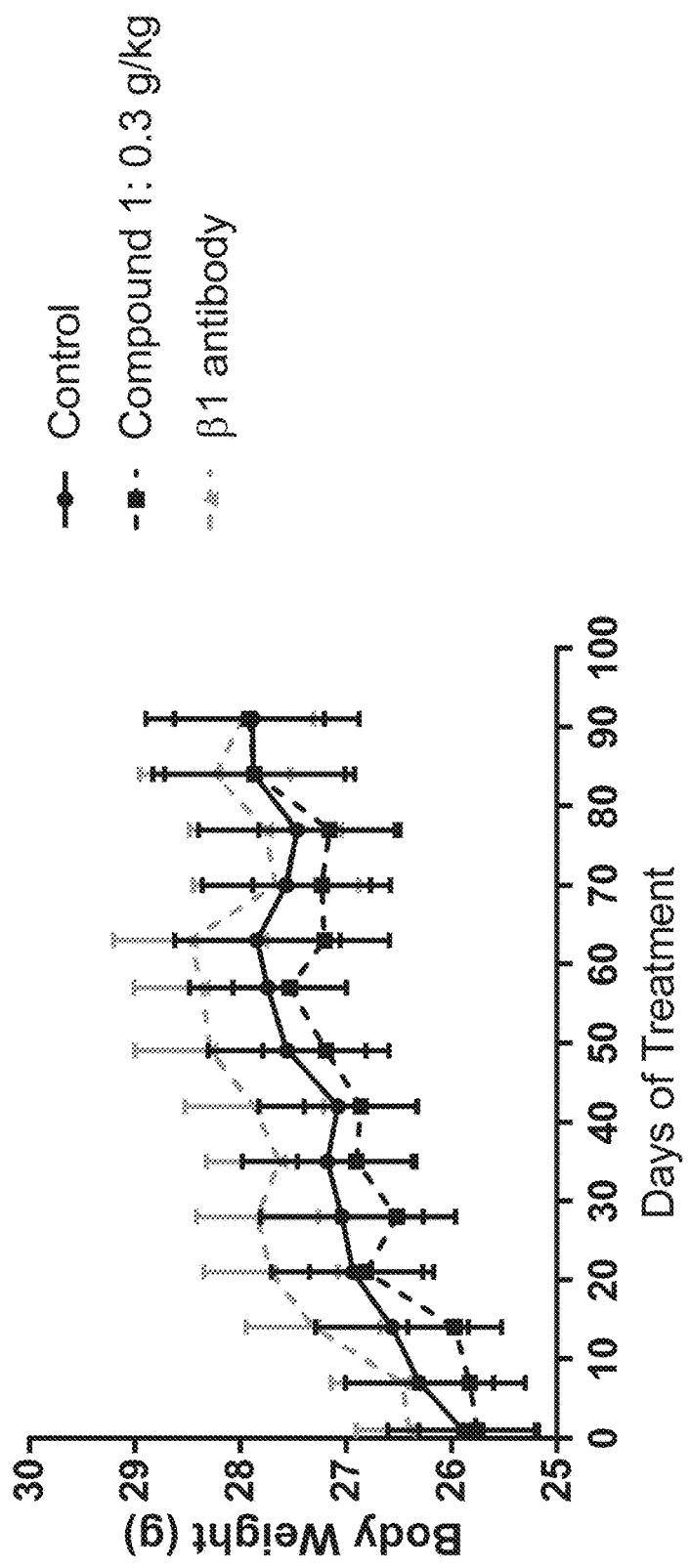
Figure 26: Body weights of Compound 1 and β1 antibody treated APP23 mice (mean and SEM)

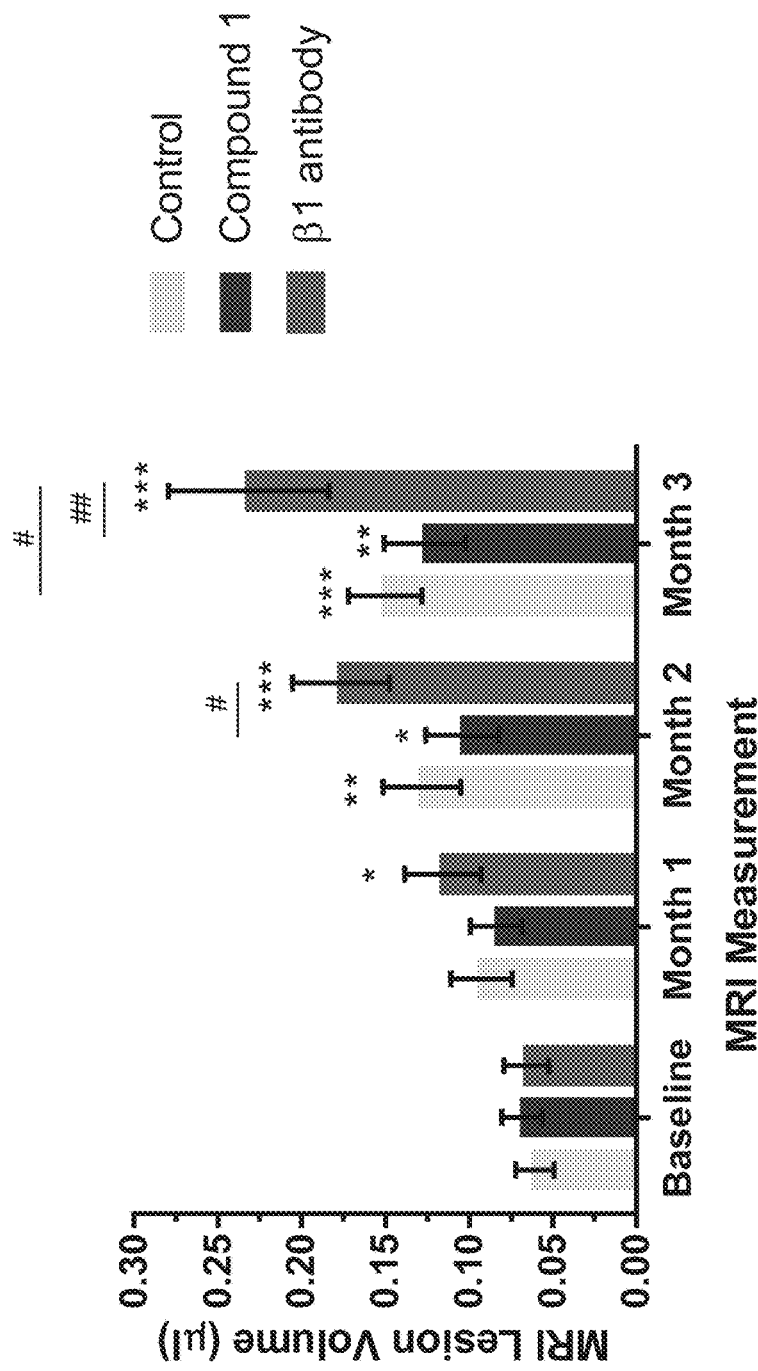
Figure 27: Total lesion volume detected in APP23 mice by MRI (mean and SEM)

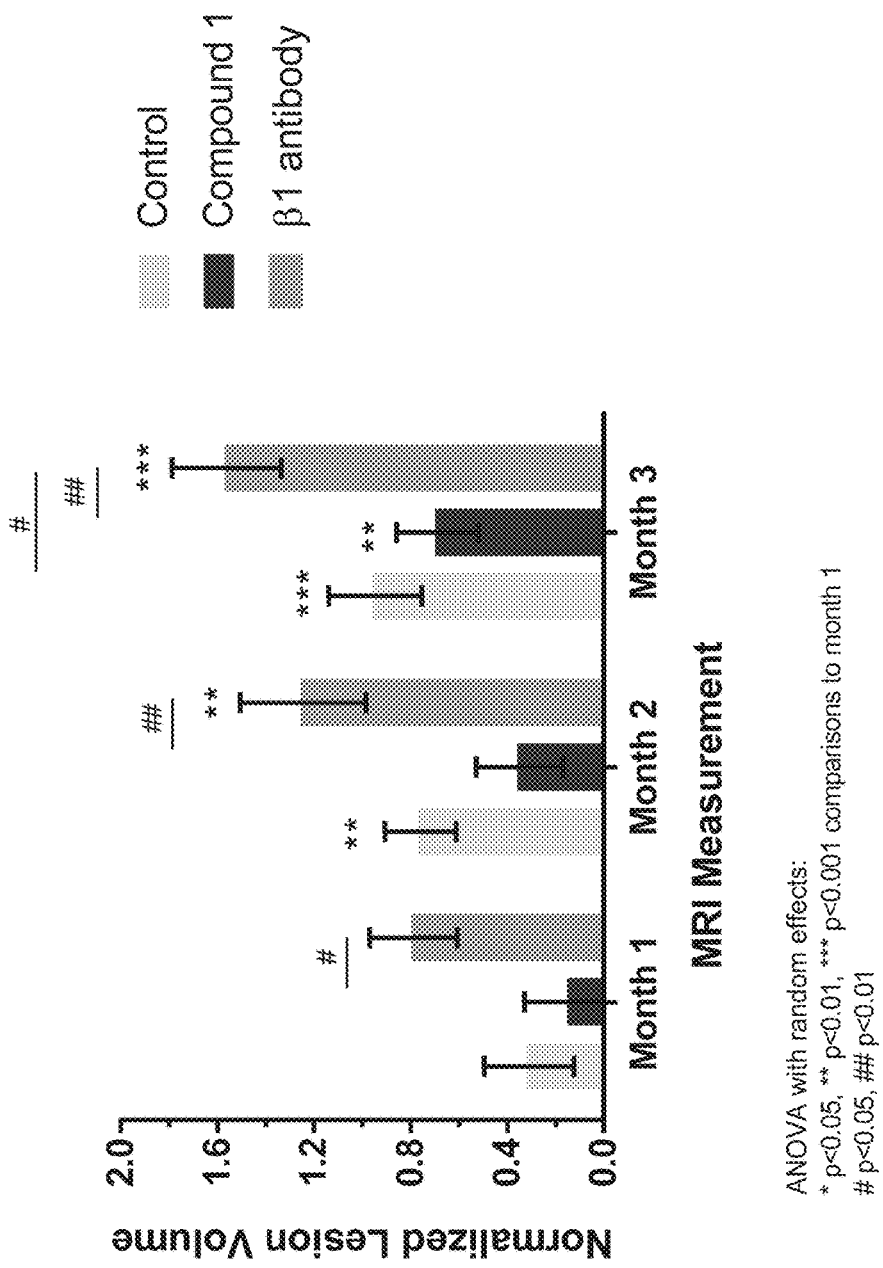
Figure 28: Total lesion volume in APP23 mice normalized to baseline (transformed to natural logarithm) (mean and SEM)

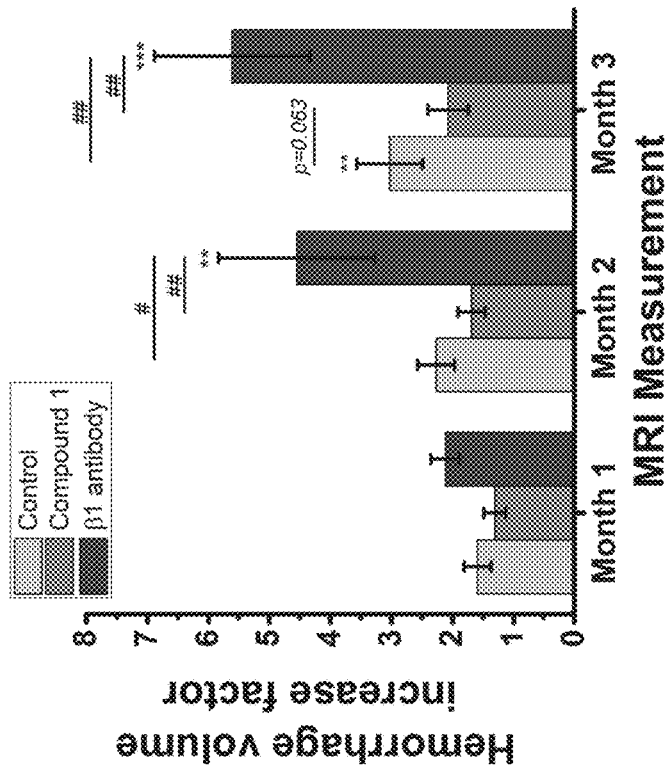
Figure 29: Lesion volume increase factor calculated relative to baseline (mean and SEM)

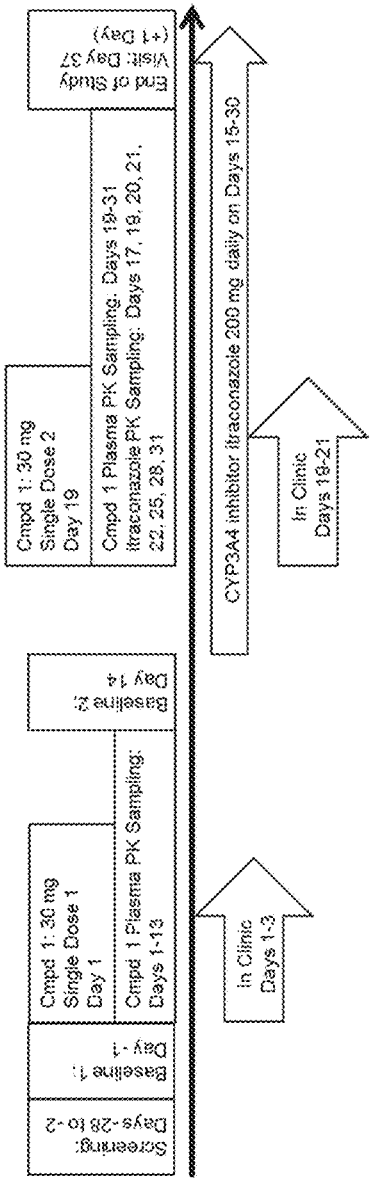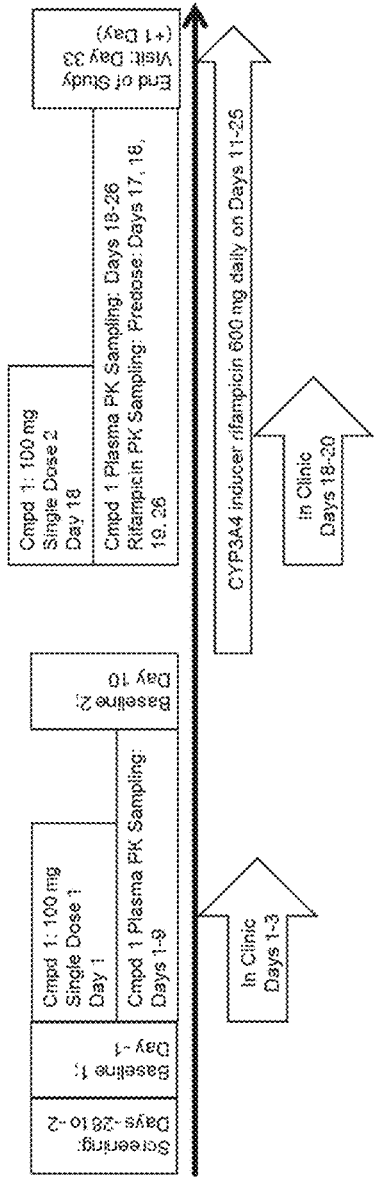
Figure 30: Design of a two part, open-label, two-period, fixed-sequence study in healthy subjects to evaluate the PK of Compound 1 when given alone and in combination with the strong CYP3A4 inhibitor itraconazole or the strong CYP3A4 inducer rifampicin

OXAZINE DERIVATIVE FOR USE IN THE TREATMENT OR PREVENTION OF CEREBRAL AMYLOID ANGIOPATHY

FIELD OF THE INVENTION

The present invention relates to an oxazine derivative, and pharmaceutical compositions comprising such oxazine derivative, for use in the treatment or prevention of cerebral amyloid angiopathy; and, in particular, where the compound is used in the treatment or prevention of cerebral amyloid angiopathy in a patient carrying one or two copies of the ApoE4 allele.

BACKGROUND TO THE INVENTION

Cerebral amyloid angiopathy (CAA) is a common age related cerebral small vessel disease, characterised by progressive deposition of amyloid-β (Aβ), in particular Aβ40, in the wall of small to medium sized arteries, arterioles and capillaries of the cerebral cortex and overlying leptomeninges (Charidimou A et al., 2011). CAA often coexists with Alzheimer's disease (AD). Mild forms of CAA often appear asymptomatic; however, CAA may also lead to severe vascular pathologies and is a risk factor for cerebral hemorrhages ranging from silent microbleeds to spontaneous intracerebral haemorrhage, a devastating form of stroke.

APOE4 is a strong genetic risk factor for both AD and CAA (Shinohara M et al., 2016). Human ApoE is located on chromosome 19 (gene APOE, Uniprot P02649). Three major isoforms (apoE2, -3 and -4) are known in humans. ApoE4 (with Arg at positions 112 and 158) has an allele frequency of 5-35% in humans (Verghese P B et al., 2011) and ApoE4 homozygotes are estimated to represent about 2 to 3% of the general population (Quintino-Santos S R et al., 2012).

It has been shown that the ApoE4 allele is strongly associated with Aβ deposition in the cortical capillaries, so called capillary CAA (CAA-Type 1) (Thal et al., 2002). The second type of CAA (CAA-Type 2) presents Aβ deposition in leptomeningeal and cortical vessels, with the exception of cortical capillaries. CAA-type 2 is not associated with the ApoE4 allele.

Strategies that target decreasing Aβ by either: enhancing the amyloid clearance with an active or passive immunotherapy against Aβ; or decreasing production through inhibition of Beta-site-APP cleaving enzyme-1 (BACE-1, an enzyme involved in the processing of the amyloid precursor protein [APP]), may be of potential therapeutic value in the treatment of CAA. However, no effective disease-modifying treatment of CAA, nor the intracerebral haemorrhages associated therewith, has yet been described in the literature.

Beckmann N et al., 2016, describe the suitability of longitudinal noninvasive magnetic resonance imaging (MRI) in monitoring cerebral microhaemorrhages in vivo. In this study, the authors treated aged APP23 mice for three months with a potent BACE-inhibitor, NB360, and Aβ-antibody β1. In contrast to treatment with Aβ-antibody β1, volumetric MRI assessment revealed no effect on CAA-related microhaemorrhage in mice treated with NB360.

SUMMARY OF THE INVENTION

The compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, referred to herein as "Compound 1", is an orally active BACE inhibitor, previously described in WO 2012/095469 A1, with an approximately 3-fold selectivity for BACE-1 over BACE-2 and no relevant off-target binding or activity.

In the absence of any demonstrated disease-modifying therapy, there is a high degree of uncertainty as to whether any potential therapeutic agent will prove effective in the treatment or prevention of CAA and the associated intracerebral haemorrhages. However, the high degree of effectiveness demonstrated herein by Compound 1 in lowering Aβ deposition in the walls of brain blood vessels and the reduction in intracerebral haemorrhages observed following treatment with Compound 1 in the APP23 transgenic mouse model of CAA suggests that Compound 1 will be effective in the treatment or prevention of CAA and the associated intracerebral haemorrhages. In view of the data provided herein which demonstrates the ability of Compound 1 to reduce cortical capillary Aβ deposition in APP23 transgenic mice, Compound 1 is expected to be particularly effective in the treatment of CAA-Type 1.

Compound 1 is also expected to be of particular benefit to patients who are predisposed to the development of CAA, for example patients carrying one or two copies of the ApoE4 allele. As such, a Phase II/III clinical trial is described herein which has been designed to demonstrate the effectiveness of Compound 1 in the prevention of AD and assess its effectiveness on CAA in a population of cognitively unimpaired ApoE4 homozygote patients; or cognitively unimpaired amyloid positive ApoE4 heterozygote patients. Based on current knowledge, the findings from this proposed clinical trial and the results described herein may be generalised and applicable to CAA in patients beyond ApoE4 homozygotes and heterozygotes (for example in patients that develop CAA as a consequence of aging; have Down's syndrome (Kumar-Singh S, 2008); or carry mutations in the genes for presenilin-1 (Dermaut B et al., 2001), or amyloid precursor protein (Kumar-Singh S, 2008)) since a BACE inhibitor therapy would be expected to reduce and/or prevent Aβ accumulation and thereby deposition in the walls of the blood vessels of the brain independent of the multiple potential causes of CAA.

In a first aspect of the invention, there is therefore provided the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for use in the treatment or prevention of cerebral amyloid angiopathy.

In a second aspect of the invention, there is provided a pharmaceutical composition comprising N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for use in the treatment or prevention of cerebral amyloid angiopathy.

In a third aspect of the invention, there is provided a method for the treatment or prevention of cerebral amyloid angiopathy which method comprises administering to a patient in need thereof a therapeutically effective amount of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof.

In a fourth aspect of the invention, there is provided a method for the treatment or prevention of cerebral amyloid angiopathy which method comprises administering to a patient a pharmaceutical composition comprising a therapeutically effective amount of the compound N-(6-((3R,6R)-5-amino-3,6-dimethyl-6-(trifluoromethyl)-3,6-dihydro-2H-

1,4-oxazin-3-yl)-5-fluoropyridin-2-yl)-3-chloro-5-(trifluoromethyl)picolinamide, or a pharmaceutically acceptable salt thereof.

In a fifth aspect of the invention, there is provided the use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the treatment or prevention of cerebral amyloid angiopathy.

In a sixth aspect of the invention, there is provided the use of a pharmaceutical composition comprising the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the treatment or prevention of cerebral amyloid angiopathy.

In a seventh aspect of the invention, there is provided the use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the manufacture of a medicament for the treatment or prevention of cerebral amyloid angiopathy.

DESCRIPTION OF THE INVENTION

List of Figures

FIG. 1: Effect of acute administration of Compound 1 on forebrain Aβ40 levels in APOE4-TR male and female mice FIG. 2: Effect of acute administration of Compound 1 on CSF Aβ40 levels in APOE4-TR male and female mice FIG. 3: Effect of acute administration of Compound 1 on CSF Aβ42 levels in APOE4-TR male and female mice FIG. 4: Compound 1 acute exposure in APOE4-TR male and female mice FIG. 5: Brain PK/PD relationship (individual data)

FIG. 6: Brain PK/PD relationship (Mean±SD)

FIG. 7: Effect of Compound 1 on CSF Aβ40 levels after two-week exposure in multiple ascending oral dose study in human subjects FIG. 8: Effect of Compound 1 on CSF Aβ40 levels in human subjects—% change from baseline at 3 months FIG. 9: Effect of Compound 1 on Aβ40 in Triton TX-100 extracted aged APP23 brains FIG. 10: Effect of Compound 1 on Aβ42 in Triton TX-100 extracted aged APP23 brains FIG. 11: Effect of Compound 1 on sAPPα in Triton TX-100 extracted aged APP23 brains FIG. 12: Effect of Compound 1 on sAPPβ (Swe) in Triton TX-100 extracted aged APP23 brains FIG. 13: Effect of Compound 1 treatment on Aβ40 in the cerebrospinal fluid of aged APP23 mice FIG. 14: Effect of Compound 1 on formic acid soluble Aβ40 in aged APP23 mice FIG. 15: Effect of Compound 1 on formic acid soluble Aβ42 in aged APP23 mice FIG. 16: Effect of Compound 1 on formic acid soluble total Aβ (40+42) in aged APP23 mice FIG. 17: Effect of Compound 1 on formic acid soluble Aβ42/40 ratio in aged APP23 mice FIG. 18: Effect of Compound 1 on number of total CD31+ brain blood vessels in aged APP23 mice FIG. 19: Effect of Compound 1 on number of total small+medium and large CD31+ brain blood vessels in aged APP23 mice FIG. 20: Effect of Compound 1 on % of vessels with >10% Aβ coverage in aged APP23 mice FIG. 21: Effect of Compound 1 on % of small+medium and large vessels with >10% Aβ coverage in aged APP23 mice FIG. 22: Effect of Compound 1 on CAA frequency (of vessels with >10% Aβ coverage) in aged APP23 mice FIG. 23: Effect of Compound 1 on CAA frequency (of small+medium and large vessels (of vessels with >10% Aβ coverage) in aged APP23 mice FIG. 24: Effect of Compound 1 on total vessel-associated Aβ area in aged APP23 mice FIG. 25: Effect of Compound 1 on total vessel-associated Aβ area (for small+medium and large vessels) in aged APP23 mice FIG. 26: Body weights of Compound 1 and β1 antibody treated APP23 mice FIG. 27: Total lesion volume detected in APP23 mice by MRI FIG. 28: Total lesion volume in APP23 mice normalized to baseline FIG. 29: Lesion volume increase factor calculated relative to baseline FIG. 30: Design of a two part, open-label, two-period, fixed-sequence study in healthy subjects to evaluate the PK of Compound 1 when given alone and in combination with the strong CYP3A4 inhibitor itraconazole or the strong CYP3A4 inducer rifampicin Series A Embodiments of the First Aspect of the Invention Embodiment A1: The compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for use in the treatment or prevention of cerebral amyloid angiopathy.

Embodiment A2: The compound, or a pharmaceutically acceptable salt thereof, for the use according to Embodiment A1, wherein the compound is used for the treatment or prevention of cerebral amyloid angiopathy in a patient having Alzheimer's disease.

Embodiment A3: The compound, or a pharmaceutically acceptable salt thereof, for the use according to Embodiment A1 or A2, wherein the compound is used in the treatment or prevention of cerebral amyloid angiopathy in a patient carrying a genetic predisposition for the development of cerebral amyloid angiopathy.

Embodiment A4: The compound, or a pharmaceutically acceptable salt thereof, for the use according to Embodiment A3, wherein the genetic predisposition for the development of cerebral amyloid angiopathy is:
  i. Down's syndrome;
  ii. a mutation in the gene for amyloid precursor protein or presenilin-1; or
  iii. the presence of one or two copies of the ApoE4 allele.

Embodiment A5: The compound, or a pharmaceutically acceptable salt thereof, for the use according to Embodiment A4, wherein the patient carries one or two copies of the ApoE4 allele.

Embodiment A6: The compound, or a pharmaceutically acceptable salt thereof, for the use according to Embodiment A5, wherein the patient carries one copy of the ApoE4 allele.

Embodiment A7: The compound, or a pharmaceutically acceptable salt thereof, for the use according to Embodiment A5, wherein the patient carries two copies of the ApoE4 allele.

Embodiment A8: The compound, or a pharmaceutically acceptable salt thereof, for the use according to any one of Embodiments A1 to A7, wherein the patient is amyloid-positive.

Embodiment A9: The compound, or a pharmaceutically acceptable salt thereof, for the use according to Embodiment A8, wherein the amyloid-positivity is determined by PET or CSF measurement.

Embodiment A10: The compound, or a pharmaceutically acceptable salt thereof, for the use according to any one of Embodiments A1 to A9, wherein the patient is between 60 and 75 years of age.

Embodiment A11: The compound, or a pharmaceutically acceptable salt thereof, for the use according to any one of Embodiments A1 to A10, wherein the compound is used at a daily dose which results in at least a 70% lowering of Aβ 1-40 in CSF following two weeks of compound exposure.

Embodiment A12: The compound, or a pharmaceutically acceptable salt thereof, for the use according to any one of Embodiments A1 to A10, wherein the compound is used at a daily dose which results in at least a 50% lowering of Aβ 1-40 in CSF following two weeks of compound exposure.

Embodiment A13: The compound, or a pharmaceutically acceptable salt thereof, for the use according to any one of Embodiments A1 to A10, wherein the compound is used at a dose of between 10 and 30 mg per day.

Embodiment A14: The compound, or a pharmaceutically acceptable salt thereof, for the use according to any one of Embodiments A1 to A10, wherein the compound is used at a dose of between 30 and 50 mg per day.

Embodiment A15: The compound, or a pharmaceutically acceptable salt thereof, for the use according to any one of Embodiments A1 to A10, wherein the compound is used at a dose of 15 mg per day.

Embodiment A16: The compound, or a pharmaceutically acceptable salt thereof, for the use according to any one of Embodiments A1 to A10, wherein the compound is used at a dose of 50 mg per day.

Embodiment A17: The compound, or a pharmaceutically acceptable salt thereof, for the use according to any one of Embodiments A1 to A10, wherein the compound is used at a daily dose which results in a plasma steady state Cmax value of between 70 and 170 ng/ml.

Embodiment A18: The compound, or a pharmaceutically acceptable salt thereof, for the use according to any one of Embodiments A1 to A10, wherein the compound is used at a daily dose which results in a plasma steady state Cmax value of between 200 and 500 ng/ml.

Embodiment A19: The compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for use in the treatment or prevention of cerebral amyloid angiopathy in a patient having Alzheimer's disease.

Embodiment A20: The compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for use in the treatment or prevention of cerebral amyloid angiopathy in a patient carrying one or two copies of the ApoE4 allele.

Embodiment A21: The compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for use in the treatment or prevention of cerebral amyloid angiopathy in a patient having Alzheimer's disease and carrying one or two copies of the ApoE4 allele.

Embodiment A22: The compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for use in the treatment or prevention of cerebral amyloid angiopathy in a patient having Alzheimer's disease and carrying one or two copies of the ApoE4 allele, and wherein the compound is used at a dose of 15 or 50 mg per day.

Embodiment A23: The compound for the use according to any one of Embodiments A1 to A22, wherein the compound is in free form.

Embodiment A24: The compound for the use according to any one of Embodiments A1 to A23, wherein the patient is not simultaneously treated with an inhibitor or inducer of CYP3A4.

Embodiment A25: The compound for the use according to any one of Embodiments A1 to A23, wherein the patient is not simultaneously treated with a CYP3A4 inhibitor or inducer for a period longer than three months.

Embodiment A26: The compound for the use according to Embodiment A24 or A25, wherein the CYP3A4 inhibitor is a strong, moderate, or weak inhibitor of CYP3A4; and the CYP3A4 inducer is a strong, moderate, or weak inducer of CYP3A4.

Embodiment A27: The compound for the use according to Embodiment A26, wherein the CYP3A4 inhibitor is a strong inhibitor of CYP3A4; and the CYP3A4 inducer is a strong inducer of CYP3A4.

Embodiment A28: The compound for the use according to any one of Embodiments A1 to A27 wherein the cerebral amyloid angiopathy is CAA-Type 1.

Series B Embodiments of the Second Aspect of the Invention

Embodiment B1: A pharmaceutical composition comprising the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for use in the treatment or prevention of cerebral amyloid angiopathy.

Embodiment B2: The pharmaceutical composition for the use according to Embodiment B1, wherein the pharmaceutical composition is used for the treatment or prevention of cerebral amyloid angiopathy in a patient having Alzheimer's disease.

Embodiment B3: The pharmaceutical composition for the use according to Embodiment B1 or B2, wherein the pharmaceutical composition is used in the treatment or prevention of cerebral amyloid angiopathy in a patient carrying a genetic predisposition for the development of cerebral amyloid angiopathy.

Embodiment B4: The pharmaceutical composition for the use according to Embodiment B3, wherein the genetic predisposition for the development of cerebral amyloid angiopathy is:
  i. Down's syndrome;
  ii. a mutation in the gene for amyloid precursor protein or presenilin-1; or
  iii. the presence of one or two copies of the ApoE4 allele.

Embodiment B5: The pharmaceutical composition for the use according to Embodiment B4, wherein the patient carries one or two copies of the ApoE4 allele.

Embodiment B6: The pharmaceutical composition for the use according to Embodiment B5, wherein the patient carries one copy of the ApoE4 allele.

Embodiment B7: The pharmaceutical composition for the use according to Embodiment B5, wherein the patient carries two copies of the ApoE4 allele.

Embodiment B8: The pharmaceutical composition for the use according to any one of Embodiments B1 to B7, wherein the patient is amyloid-positive.

Embodiment B9: The pharmaceutical composition for the use according to Embodiment B8, wherein the amyloid-positivity is determined by PET or CSF measurement.

Embodiment B10: The pharmaceutical composition for the use according to any one of Embodiments B1 to B9, wherein the patient is between 60 and 75 years of age.

Embodiment B11: The pharmaceutical composition for the use according to any one of Embodiments B1 to B10, wherein the compound is used at a daily dose which results in at least a 70% lowering of Aβ 1-40 in CSF following two weeks of compound exposure.

Embodiment B12: The pharmaceutical composition for the use according to any one of Embodiments B1 to B10, wherein the compound is used at a daily dose which results in at least a 50% lowering of Aβ 1-40 in CSF following two weeks of compound exposure.

Embodiment B13: The pharmaceutical composition for the use according to any one of Embodiments B1 to B10, wherein the compound is used at a dose of between 10 and 30 mg per day.

Embodiment B14: The pharmaceutical composition for the use according to any one of Embodiments B1 to B10, wherein the compound is used at a dose of between 30 and 50 mg per day.

Embodiment B15: The pharmaceutical composition for the use according to any one of Embodiments B1 to B10, wherein the compound is used at a dose of 15 mg per day.

Embodiment B16: The pharmaceutical composition for the use according to any one of Embodiments B1 to B10, wherein the compound is used at a dose of 50 mg per day.

Embodiment B17: The pharmaceutical composition for the use according to any one of Embodiments B1 to B10, wherein the compound is used at a daily dose which results in a plasma steady state Cmax value of between 70 and 170 ng/ml.

Embodiment B18: The pharmaceutical composition for the use according to any one of Embodiments B1 to B10, wherein the compound is used at a daily dose which results in a plasma steady state Cmax value of between 200 and 500 ng/ml.

Embodiment B19: A pharmaceutical composition comprising the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl) picolinamide, or a pharmaceutically acceptable salt thereof, for use in the treatment or prevention of cerebral amyloid angiopathy in a patient having Alzheimer's disease.

Embodiment B20: A pharmaceutical composition comprising the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl) picolinamide, or a pharmaceutically acceptable salt thereof, for use in the treatment or prevention of cerebral amyloid angiopathy in a patient carrying one or two copies of the ApoE4 allele.

Embodiment B21: A pharmaceutical composition comprising the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl) picolinamide, or a pharmaceutically acceptable salt thereof, for use in the treatment or prevention of cerebral amyloid angiopathy in a patient having Alzheimer's disease and carrying one or two copies of the ApoE4 allele.

Embodiment B22: A pharmaceutical composition comprising the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl) picolinamide, or a pharmaceutically acceptable salt thereof, for use in the treatment or prevention of cerebral amyloid angiopathy in a patient having Alzheimer's disease and carrying one or two copies of the ApoE4 allele, and wherein the compound is used at a dose of 15 or 50 mg per day.

Embodiment B23: The pharmaceutical composition for the use according to any one of Embodiments B1 to B22, wherein the compound is in free form.

Embodiment B24: The pharmaceutical composition for the use according to any one of Embodiments B1 to B23, wherein the patient is not simultaneously treated with an inhibitor or inducer of CYP3A4.

Embodiment B25: The pharmaceutical composition for the use according to any one of Embodiments B1 to B23, wherein the patient is not simultaneously treated with a CYP3A4 inhibitor or inducer for a period longer than three months.

Embodiment B26: The pharmaceutical composition for the use according to Embodiment B24 or B25, wherein the CYP3A4 inhibitor is a strong, moderate, or weak inhibitor of CYP3A4; and the CYP3A4 inducer is a strong, moderate, or weak inducer of CYP3A4.

Embodiment B27: The pharmaceutical composition for the use according to Embodiment B26, wherein the CYP3A4 inhibitor is a strong inhibitor of CYP3A4; and the CYP3A4 inducer is a strong inducer of CYP3A4.

Embodiment B28: The pharmaceutical composition for the use according to any one of Embodiments B1 to B27 wherein the cerebral amyloid angiopathy is CAA-Type 1.

Series C Embodiments of the Third Aspect of the Invention

Embodiment C1: A method for the treatment or prevention of cerebral amyloid angiopathy which method comprises administering to a patient in need thereof a therapeutically effective amount of the compound N-(6-((3R,6R)-5-amino-3,6-dimethyl-6-(trifluoromethyl)-3,6-dihydro-2H-1, 4-oxazin-3-yl)-5-fluoropyridin-2-yl)-3-chloro-5-(trifluoromethyl)picolinamide, or a pharmaceutically acceptable salt thereof.

Embodiment C2: The method according to Embodiment C1, wherein the patient has Alzheimer's disease.

Embodiment C3: The method according to Embodiment C1 or C2, wherein the patient carries a genetic predisposition for the development of cerebral amyloid angiopathy.

Embodiment C4: The method according to Embodiment C3, wherein the genetic predisposition for the development of cerebral amyloid angiopathy is:
  i. Down's syndrome;
  ii. a mutation in the gene for amyloid precursor protein or presenilin-1; or
  iii. the presence of one or two copies of the ApoE4 allele.

Embodiment C5: The method according to Embodiment C4, wherein the patient carries one or two copies of the ApoE4 allele.

Embodiment C6: The method according to Embodiment C5, wherein the patient carries one copy of the ApoE4 allele.

Embodiment C7: The method according to Embodiment C5, wherein the patient carries two copies of the ApoE4 allele.

Embodiment C8: The method according to any one of Embodiments C1 to C7, wherein the patient is amyloid-positive.

Embodiment C9: The method according to Embodiment C8, wherein the amyloid-positivity is determined by PET or CSF measurement.

Embodiment C10: The method according to any one of Embodiments C1 to C9, wherein the patient is over 60, 61, 62, 63, 64, 65, 66, 67, 68, 69, 70, 71, 72, 73, 74 or 75 years of age.

Embodiment C11: The method according to any one of Embodiments C1 to C10, wherein the patient is between 60 and 75 years of age.

Embodiment C12: The method according to any one of Embodiments C1 to C11, wherein administering the compound results in at least 10, 20, 30, 40, 50, 60, 70 or 80% lowering of Aβ 1-40 in CSF, blood, or plasma, following 2, 13, 26, 52, 78, 104, 130, 156, 182, 208, 234, 260, 286, 312, 338, 332, 390, or 416 weeks of compound exposure.

Embodiment C13: The method according to any one of Embodiments C1 to C11, wherein administering the compound results in at least a 70% lowering of Aβ 1-40 in CSF, blood, or plasma, following 2, 13, 26, 52, 78, 104, 130, 156, 182, 208, 234, 260, 286, 312, 338, 332, 390, or 416 weeks of compound exposure.

Embodiment C14: The method according to any one of Embodiments C1 to C11, wherein administering the compound results in at least a 50% lowering of Aβ 1-40 in CSF, blood, or plasma, following 2, 13, 26, 52, 78, 104, 130, 156, 182, 208, 234, 260, 286, 312, 338, 332, 390, or 416 weeks of compound exposure.

Embodiment C15: The method according to any one of Embodiments C1 to C11, wherein administering the compound results in a lowering of Aβ 1-40 in CSF, blood or plasma, in the range of 10, 20, 30, 40, 50, 60, 70 or 80% to 99, 97, 95, 93, 90, 87, 85, 80, 75, 70, 65, 60, 55, or 50%, following 2, 13, 26, 52, 78, 104, 130, 156, 182, 208, 234, 260, 286, 312, 338, 332, 390, or 416 weeks of compound exposure.

Embodiment C16: The method according to any one of Embodiments C1 to C11, wherein administering the compound results in a lowering of Aβ 1-40 in CSF, blood or plasma, in the range of 40 to 70%, 45 to 65%, or 50 to 60%, or of at least 50% in at least 80, 85, 90, 93, 95, 97, or 99% of the patients or in 80, 85, or 90 to 99, 97, 95, or 93% of the patients.

Embodiment C17: The method according to any one of Embodiments C1 to C11, wherein the compound is used at a daily dose which results in a lowering of Aβ 1-40 in CSF, blood or plasma, in the range of 65 to 95%, 75 to 90%, or 80 to 90%, or of at least 80% in at least 80, 85, 90, 93, 95, 97, or 99% of the patients or in 80, 85, or 90 to 99, 97, 95, or 93% of the patients.

Embodiment C18: The method according to any one of Embodiments C1 to C11, wherein the therapeutically effective amount of the compound is a dose of between 5 and 10; 10 and 15; 15 and 20; 20 and 25; 25 and 30; 30 and 35; 35 and 40; 45 and 50; 50 and 55 mg; 55 and 60 mg; 60 and 100 mg; 100 and 200; 200 and 300 mg; 15 and 85 mg; 50 and 85 mg; 15 and 300 mg; or 50 and 300 mg per day.

Embodiment C19: The method according to any one of Embodiments C1 to C11, wherein the therapeutically effective amount of the compound is a dose of between 10 and 30 mg per day.

Embodiment C20: The method according to any one of Embodiments C1 to C11, wherein the therapeutically effective amount of the compound is a dose of between 30 and 50 mg per day.

Embodiment C21: The method according to any one of Embodiments C1 to C11, wherein the therapeutically effective amount of the compound is a dose of 15 mg per day.

Embodiment C22: The method according to any one of Embodiments C1 to C11, wherein the therapeutically effective amount of the compound is a dose of 50 mg per day.

Embodiment C23: The method according to any one of Embodiments C1 to C11, wherein the therapeutically effective amount of the compound is a dose which results in a plasma steady state Cmax value of between 0 and 50; 50 and 100; 100 and 150; 150 and 200; 200 and 250; 250 and 300; 300 and 350; 350 and 400; 400 and 450; 450 and 500; 500 and 550; 550 and 600; 600 and 650; or 650 and 700 ng/ml.

Embodiment C24: The method according to any one of according to any one of Embodiments C1 to C11, wherein the therapeutically effective amount of the compound is a dose which results in a plasma steady state Cmax value of between 70 and 170 ng/ml.

Embodiment C25: The method according to any one of according to any one of Embodiments C1 to C11, wherein the therapeutically effective amount of the compound is a dose which results in a plasma steady state Cmax value of between 200 and 500 ng/ml.

Embodiment C26: A method for the treatment or prevention of cerebral amyloid angiopathy which method comprises administering to a patient a therapeutically effective amount of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, wherein the patient has Alzheimer's disease.

Embodiment C27: A method for the treatment or prevention of cerebral amyloid angiopathy which method comprises administering to a patient a therapeutically effective amount of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, wherein the patient carries one or two copies of the ApoE4 allele.

Embodiment C28: A method for the treatment or prevention of cerebral amyloid angiopathy which method comprises administering to a patient a therapeutically effective amount of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, wherein the patient has Alzheimer's disease and carries one or two copies of the ApoE4 allele.

Embodiment C29: A method for the treatment or prevention of cerebral amyloid angiopathy which method comprises administering to a patient a therapeutically effective amount of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, wherein the patient has Alzheimer's disease and carries one or two copies of the ApoE4 allele, and wherein the therapeutically effective amount of the compound is a dose of 15 or 50 mg per day.

Embodiment C30: The method according to any one of Embodiments C1 to C29, wherein the compound is in free form.

Embodiment C31: The method according to any one of Embodiments C1 to C30 wherein Compound 1 is comprised within a pharmaceutical composition.

Embodiment C32: The method according to any one of Embodiments C1 to C31, wherein the patient is not simultaneously treated with an inhibitor or inducer of CYP3A4.

Embodiment C33: The method according to any one of Embodiments C1 to C31, wherein the patient is not simultaneously treated with a CYP3A4 inhibitor or inducer for a period longer than three months.

Embodiment C34: The method according to Embodiment C32 or C33, wherein the CYP3A4 inhibitor is a strong, moderate, or weak inhibitor of CYP3A4; and the CYP3A4 inducer is a strong, moderate, or weak inducer of CYP3A4.

Embodiment C35: The method according to Embodiment C34, wherein the CYP3A4 inhibitor is a strong inhibitor of CYP3A4; and the CYP3A4 inducer is a strong inducer of CYP3A4.

Embodiment C36: The method according to any one of Embodiments C1 to C35 wherein the cerebral amyloid angiopathy is CAA-Type 1.

Series D Embodiments of the Fifth Aspect of the Invention

Embodiment D1: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the treatment or prevention of cerebral amyloid angiopathy.

Embodiment D2: The use according to Embodiment D1, wherein the compound is used in the treatment or prevention of cerebral amyloid angiopathy in a patient having Alzheimer's disease.

Embodiment D3: The use according to Embodiment D1 or D2, wherein the compound is used in the treatment or prevention of cerebral amyloid angiopathy in a patient carrying a genetic predisposition for the development of cerebral amyloid angiopathy.

Embodiment D4: The use according to Embodiment D3, wherein the genetic predisposition for the development of cerebral amyloid angiopathy is:
  i. Down's syndrome;
  ii. a mutation in the gene for amyloid precursor protein or presenilin-1; or
  iii. the presence of one or two copies of the ApoE4 allele.

Embodiment D5: The use according to Embodiment D4, wherein the patient carries one or two copies of the ApoE4 allele.

Embodiment D6: The use according to Embodiment D5, wherein the patient carries one copy of the ApoE4 allele.

Embodiment D7: The use according to Embodiment D5, wherein the patient carries two copies of the ApoE4 allele.

Embodiment D8: The use according to any one of Embodiments D1 to D7, wherein the patient is amyloid-positive.

Embodiment D9: The use according to Embodiment D8, wherein the amyloid-positivity is determined by PET or CSF measurement.

Embodiment D10: The use according to any one of Embodiments D1 to D9, wherein the patient is between 60 and 75 years of age.

Embodiment D11: The use according to any one of Embodiments D1 to D10, wherein the compound is used at a daily dose which results in at least a 70% lowering of Aβ 1-40 in CSF following two weeks of compound exposure.

Embodiment D12: The use according to any one of Embodiments D1 to D10, wherein the compound is used at a daily dose which results in at least a 50% lowering of Aβ 1-40 in CSF following two weeks of compound exposure.

Embodiment D13: The use according to any one of Embodiments D1 to D10, wherein the compound is used at a dose of between 10 and 30 mg per day.

Embodiment D14: The use according to any one of Embodiments D1 to D10, wherein the compound is used at a dose of between 30 and 50 mg per day.

Embodiment D15: The use according to any one of Embodiments D1 to D10, wherein the compound is used at a dose of 15 mg per day.

Embodiment D16: The use according to any one of Embodiments D1 to D10, wherein the compound is used at a dose of 50 mg per day.

Embodiment D17: The use according to any one of Embodiments D1 to D10, wherein the compound is used at a daily dose which results in a plasma steady state Cmax value of between 70 and 170 ng/ml.

Embodiment D18: The use according to any one of Embodiments D1 to D10, wherein the compound is used at a daily dose which results in a plasma steady state Cmax value of between 200 and 500 ng/ml.

Embodiment D19: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the treatment or prevention of cerebral amyloid angiopathy in a patient having Alzheimer's disease.

Embodiment D20: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the treatment or prevention of cerebral amyloid angiopathy in a patient carrying one or two copies of the ApoE4 allele.

Embodiment D21: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the treatment or prevention of cerebral amyloid angiopathy in a patient having Alzheimer's disease and carrying one or two copies of the ApoE4 allele.

Embodiment D22: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the treatment or prevention of cerebral amyloid angiopathy in a patient having Alzheimer's disease and carrying one or two copies of the ApoE4 allele, and wherein the compound is used at a dose of 15 or 50 mg per day.

Embodiment D23: The use according to any one of Embodiments D1 to D22, wherein the compound is in free form.

Embodiment D24: The use according to any one of Embodiments D1 to D23, wherein the compound is comprised within a pharmaceutical composition.

Embodiment D25: The use according to any one of Embodiments D1 to D24, wherein the patient is not simultaneously treated with an inhibitor or inducer of CYP3A4.

Embodiment D26: The use according to any one of Embodiments D1 to D24, wherein the patient is not simultaneously treated with a CYP3A4 inhibitor or inducer for a period longer than three months.

Embodiment D27: The use according to Embodiment D25 or D26, wherein the CYP3A4 inhibitor is a strong, moderate, or weak inhibitor of CYP3A4; and the CYP3A4 inducer is a strong, moderate, or weak inducer of CYP3A4.

Embodiment D28: The use according to Embodiment D27, wherein the CYP3A4 inhibitor is a strong inhibitor of CYP3A4; and the CYP3A4 inducer is a strong inducer of CYP3A4.

Embodiment D29: The use according to any one of Embodiments D1 to D28 wherein the cerebral amyloid angiopathy is CAA-Type 1.

Series E Embodiments of the Seventh Aspect of the Invention

Embodiment E1: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the manufacture of a medicament for the treatment or prevention of cerebral amyloid angiopathy.

Embodiment E2: The use according to Embodiment E1, wherein the compound is used in the treatment or prevention of cerebral amyloid angiopathy in a patient having Alzheimer's disease.

Embodiment E3: The use according to Embodiment E1 or E2, wherein the compound is used in the treatment or prevention of cerebral amyloid angiopathy in a patient carrying a genetic predisposition for the development of cerebral amyloid angiopathy.

Embodiment E4

The use according to Embodiment E3, wherein the genetic predisposition for the development of cerebral amyloid angiopathy is:
  i. Down's syndrome;
  ii. a mutation in the gene for amyloid precursor protein or presenilin-1; or
  iii. the presence of one or two copies of the ApoE4 allele.

Embodiment E5: The use according to Embodiment E4, wherein patient carries one or two copies of the ApoE4 allele.

Embodiment E6: The use according to Embodiment E5, wherein the patient carries one copy of the ApoE4 allele.

Embodiment E7: The use according to Embodiment E5, wherein the patient carries two copies of the ApoE4 allele.

Embodiment E8: The use according to any one of Embodiments E1 to E7, wherein the patient is amyloid-positive.

Embodiment E9: The use according to Embodiment E8, wherein the amyloid-positivity is determined by PET or CSF measurement.

Embodiment E10: The use according to any one of Embodiments E1 to E9, wherein the patient is between 60 and 75 years of age.

Embodiment E11: The use according to any one of Embodiments E1 to E10, wherein the compound is used at a daily dose which results in at least a 70% lowering of Aβ 1-40 in CSF following two weeks of compound exposure.

Embodiment E12: The use according to any one of Embodiments E1 to E10, wherein the compound is used at a daily dose which results in at least a 50% lowering of Aβ 1-40 in CSF following two weeks of compound exposure.

Embodiment E13: The use according to any one of Embodiments E1 to E10, wherein the compound is used at a dose of between 10 and 30 mg per day.

Embodiment E14: The use according to any one of Embodiments E1 to E10, wherein the compound is used at a dose of between 30 and 50 mg per day.

Embodiment E15: The use according to any one of Embodiments E1 to E10, wherein the compound is used at a dose of 15 mg per day.

Embodiment E16: The use according to any one of Embodiments E1 to E10, wherein the compound is used at a dose of 50 mg per day.

Embodiment E17: The use according to any one of Embodiments E1 to E10, wherein the compound is used at a daily dose which results in a plasma steady state Cmax value of between 70 and 170 ng/ml.

Embodiment E18: The use according to any one of Embodiments E1 to E10, wherein the compound is used at a daily dose which results in a plasma steady state Cmax value of between 200 and 500 ng/ml.

Embodiment E19: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the manufacture of a medicament for the treatment or prevention of cerebral amyloid angiopathy in a patient having Alzheimer's disease.

Embodiment E20: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the manufacture of a medicament for the treatment or prevention of cerebral amyloid angiopathy in a patient carrying one or two copies of the ApoE4 allele.

Embodiment E21: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the manufacture of a medicament for the treatment or prevention of cerebral amyloid angiopathy in a patient having Alzheimer's disease and carrying one or two copies of the ApoE4 allele.

Embodiment E22: Use of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide, or a pharmaceutically acceptable salt thereof, for the manufacture of a medicament for the treatment or prevention of cerebral amyloid angiopathy in a patient having Alzheimer's disease and carrying one or two copies of the ApoE4 allele, and wherein the compound is used at a dose of 15 or 50 mg per day.

Embodiment E23: The use according to any one of Embodiments E1 to E22, wherein the compound is in free form.

Embodiment E24: The use according to any one of Embodiments E1 to E23, wherein the medicament is a pharmaceutical composition.

Embodiment E25: The use according to any one of Embodiments E1 to E24, wherein the patient is not simultaneously treated with an inhibitor or inducer of CYP3A4.

Embodiment E26: The use according to any one of Embodiments E1 to E24, wherein the patient is not simultaneously treated with a CYP3A4 inhibitor or inducer for a period longer than three months.

Embodiment E27: The use according to Embodiment E25 or E26, wherein the CYP3A4 inhibitor is a strong, moderate, or weak inhibitor of CYP3A4; and the CYP3A4 inducer is a strong, moderate, or weak inducer of CYP3A4.

Embodiment E28: The use according to Embodiment E27, wherein the CYP3A4 inhibitor is a strong inhibitor of CYP3A4; and the CYP3A4 inducer is a strong inducer of CYP3A4.

Embodiment E29: The use according to any one of Embodiments E1 to E28 wherein the cerebral amyloid angiopathy is CAA-Type 1.

Definitions

As used herein, the term "Compound 1" or "Cmpd 1" refers to N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethyl)picolinamide and having the following structural formula:

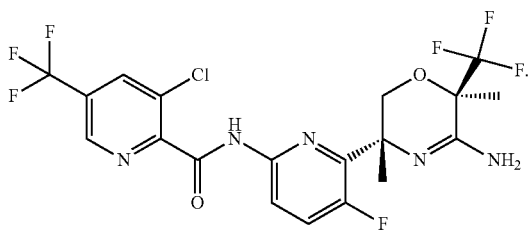 [SMILES: C[C@@]1(c2nc(NC(=O)c3ncc(C(F)(F)F)cc3Cl)ccc2F)CO[C@@](C)(C(F)(F)F)C(N)=N1]

In Example 1, using an alternative chemical naming format, "Compound 1" is also referred to as 3-chloro-5-trifluoromethyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide.

The terms "Compound 1", "Cmpd 1" and its corresponding full chemical name are used interchangeably throughout the description of the invention. It is intended that the term refers to the compound in either free form or pharmaceutically acceptable salt form, unless the context clearly indicates that only one form of the compound is intended. Compound 1 is described in WO 2012/095469 A1, Example 34. WO 2012/095469 A1 is incorporated herewith by reference in its entirety, in particular the disclosure related to the synthesis of Example 34.

As used herein, the term "Cerebral Amyloid Angiopathy" or "CAA" refers to a disease characterised by the accumulation of β-amyloid (Aβ) proteins in the walls of cortical and leptomeningeal blood vessels. CAA is a common cause of vessel wall breakdown and vascular dysfunction in older adults, making it a major contributor to fatal or disabling intracerebral hemorrhages (ICH) as well as ischemic injury and dementia (Gurol M E et al., 2016). As used herein, the term "Cerebral Amyloid Angiopathy" or "CAA" encompasses both CAA-Type 1 and CAA-Type 2 unless the context makes clear that only CAA-Type 1 or CAA-Type 2 is intended.

As used herein, the term "CAA-Type 1" refers to capillary CAA (capCAA) characterised by Aβ protein depositions in the walls of cortical capillaries (Thal et al., 2002).

As used herein, the term "CAA-Type 2" refers to CAA characterised by Aβ protein depositions in the walls of leptomeningeal and cortical vessels, with the exception of cortical capillaries (Thal et al., 2002).

As used herein, the term "treatment of CAA" refers to the administration of Compound 1 to a patient in order to slow or arrest the development of CAA or at least one of the clinical symptoms of CAA, for example ICH, ischemic injury, or dementia. The development of CAA may be assessed by measuring the accumulation of Aβ in the walls of cortical (for example occipital cortex) and leptomeningeal blood vessels using a Positron Emission Tomography (PET) tracer, for example $^{18}$F-florbetapir (Gurol M E et al., 2016). Alternatively, the development of CAA may be assessed by monitoring cerebral microbleeds (CMB) as a haemorrhagic marker of CAA (Greenberg S M et al., 2014). Suitable techniques for the monitoring of CMB include, for example, magnetic resonance imaging (MRI) susceptibility-weighted imaging (SWI) and MRI T2*-weighted gradient-recalled echo imaging (GRE), and are described in Cheng A L et al., 2013. In addition, white matter hyperintensities (WMH) occur at much greater volume in patients diagnosed with CAA than in healthy aged individuals or in patients suffering from AD or mild cognitive impairment (MCI) (Greenberg S M et al., 2014). Therefore, CAA development may be monitored by the measurement of WMH volume using MRI (Chen Y W et al., 2006). It is expected that the "treatment of CAA" will have the resultant benefit of reducing the likelihood of a cerebral ischemic event in the patient undergoing treatment for CAA. Therefore, in one embodiment of the invention, the term "treatment of CAA" is equivalent to the term "treatment of intracerebral haemorrhage". In another embodiment of the invention, the term "treatment of CAA" is equivalent to the term "treatment of CAA and/or intracerebral haemorrhage". In a further embodiment of the invention, the term "treatment of CAA" is equivalent to the term "treatment of CAA and intracerebral haemorrhage associated therewith".

As used herein, the term "prevention of CAA" refers to the prophylactic treatment of CAA; delaying the onset or progression of CAA; or delaying the onset or progression of at least one of the clinical symptoms of CAA. For example, the onset or progression of CAA is delayed for at least 0.5, 1, 2, 3, 4, 5, 6, 7, 8, 9, or 10 years. In one embodiment of the invention, the term "prevention of CAA" is equivalent to the term "prevention of intracerebral haemorrhage". In another embodiment of the invention, the term "prevention of CAA" is equivalent to the term "prevention of CAA and/or intracerebral haemorrhage". In a further embodiment of the invention, the term "prevention of CAA" is equivalent to the term "prevention of CAA and intracerebral haemorrhage associated therewith".

As used herein, the term "a genetic predisposition for the development of CAA" includes, but is not limited to situations where the genetic predisposition is due to: Down's syndrome; a mutation in the gene for amyloid precursor protein or presenilin-1; or the presence of one or two copies of the ApoE4 allele.

As used herein, the term "Alzheimer's disease" or "AD" encompasses both preclinical and clinical Alzheimer's disease unless the context makes clear that either only preclinical Alzheimer's disease or only clinical Alzheimer's disease is intended.

As used herein, the term "clinical Alzheimer's disease" or "clinical AD" encompasses both Mild Cognitive Impairment (MCI) due to AD and dementia due to AD, unless the context makes clear that either only MCI due to AD or dementia due to AD is intended. The European Medicines Agency (EMA) in its 'Draft guidelines on the clinical investigation of medicines for the treatment of AD and other dementias' (EMA/Committee for Medicinal Products for Human Use (CHMP)/539931/2014) summarises the National Institute on Aging criteria for the diagnosis of MCI due to AD and AD dementia as set out below.

Diagnosis of MCI due to AD requires evidence of intra-individual decline, manifested by:
a) A change in cognition from previously attained levels, as noted by self- or informant report and/or the judgment of a clinician.
b) Impaired cognition in at least one domain (but not necessarily episodic memory) relative to age- and education-matched normative values; impairment in more than one cognitive domain is permissible.
c) Preserved independence in functional abilities, although the criteria also accept 'mild problems' in performing instrumental activities of daily living (IADL) even when this is only with assistance (i.e. rather than insisting on independence, the criteria allow for mild dependence due to functional loss).

d) No dementia, which nominally is a function of c (above).

e) A clinical presentation consistent with the phenotype of AD in the absence of other potentially dementing disorders. Increased diagnostic confidence may be suggested by
1) Optimal: A positive Aβ biomarker and a positive degeneration biomarker
2) Less optimal:
   i. A positive Aβ biomarker without a degeneration biomarker
   ii. A positive degeneration biomarker without testing for Aβ biomarkers Diagnosis of AD dementia requires:

a) The presence of dementia, as determined by intra-individual decline in cognition and function.

b) Insidious onset and progressive cognitive decline.

c) Impairment in two or more cognitive domains; although an amnestic presentation is most common, the criteria allow for diagnosis based on nonamnestic presentations (e.g. impairment in executive function and visuospatial abilities).

d) Absence of prominent features associated with other dementing disorders.

Increased diagnostic confidence may be suggested by the biomarker algorithm discussed in the MCI due to AD section above.

As used herein, the term "preclinical Alzheimer's disease" or "preclinical AD" refers to the presence of in vivo molecular biomarkers of AD in the absence of clinical symptoms. The National Institute on Aging and Alzheimer's Association provide a scheme, shown in Table 1 below, which sets out the different stages of preclinical AD (Sperling R A et al., 2011).

TABLE 1

Preclinical AD staging categories

| Stage | Description | Aβ (PET or CSF) | Markers of neuronal injury (tau, FDG, sMRI) | Evidence of subtle cognitive change |
|---|---|---|---|---|
| Stage 1 | Asymptomatic cerebral amyloidosis | Positive | Negative | Negative |
| Stage 2 | Asymptomatic amyloidosis + "downstream" neurodegeneration | Positive | Positive | Negative |
| Stage 3 | Amyloidosis + neuronal injury + subtle cognitive/behavioral decline | Positive | Positive | Positive | sMRI = structural magnetic resonance imaging

As used herein, the term "patient" refers to a human subject.

As used herein, the term "amyloid-positive" refers to a patient who has detectable levels of accumulated Aβ in the brain. In one embodiment, a patient is "amyloid-positive" if the patient has detectable levels of accumulated Aβ in the brain based on an assessment of Aβ in the CSF or amyloid PET imaging, or both.

As used herein, the term "amyloid-positivity determined by PET" refers to an increased level of amyloid PET tracer retention compared to background. The comparison may be made by way of a visual read and/or using a semi-quantitative measure of standardized uptake ratio (SUVR). Suitable PET tracers for the measurement of amyloid-positivity via a qualitative visual read include $^{18}$F-florbetapir (Palmqvist S et al., 2015), $^{18}$F-florbetaben (NeuraCeq) and $^{18}$F-flutemetamol (Vizamyl). An SUVR of 1.1 or higher on a brain $^{18}$F-florbetapir PET scan (260 MBq for each scan) may be used as a semi-quantitative diagnostic threshold value indicative of amyloid-positivity (Schreiber S et al., 2015). An SUVR of 1.2 or 1.3 could also be used as a threshold value.

As used herein, the term "amyloid-positivity determined by CSF measurement" refers to a reduced CSF Aβ 1-42 value compared to that observed in a healthy control group. For example, amyloid-positivity may be determined by an Aβ 1-42 value of 192 ng/L or less in CSF (Mattsson N et al., 2015). However, the CSF Aβ 1-42 cut-off value used to determine amyloid-positivity will vary depending on the particular technique used (Forlenza O V et al., 2015). Amyloid positivity may also be determined by an Aβ 1-42/Aβ 1-40 ratio of less than 0.09 in CSF (Janelidze S et al., 2016). In one embodiment, the Aβ 1-42/Aβ 1-40 or Aβ42/Aβ40 ratio is less than 0.20, 0.15, 0.10, 0.09, 0.08, 0.07, 0.06 or 0.05 or between 0.20 and 0.01, 0.15 and 0.01, 0.10 and 0.01, or 0.05 and 0.01. Aβ 1-40 and Aβ 1-42 values may be measured using standard immunoassay techniques, for example using a monoclonal single antibody sandwich enzyme-linked immunosorbent (ELISA) assay on the Luminex platform (Herskovitz A Z et al., 2013) or the Meso Scale Discovery (MSD) 96-well MULTI-ARRAY human/rodent (6E10) Aβ40 and 42 sandwich immunoassays (Meso Scale Discovery, Rockville, Md., USA).

As used herein, the term "CYP3A4" refers to Cytochrome P450 3A4. CYP3A4 is an enzyme which plays a major role in the metabolism of a large variety of drugs (Luo G et al., 2004).

As used herein, the term "inducer of CYP3A4" refers to a drug which causes CYP3A4 activity levels to increase. Examples of CYP3A4 inducers include, but are not limited to, carbamazepine, phenytoin, rifampicin, and St John's wort. Techniques suitable for the measurement of CYP3A4 activity are well known (see, for example, Sevrioukova I F, Poulos T L, 2015). "Strong", "moderate", and "weak" inducers of CYP3A4 are drugs that decrease the plasma area under the curve (AUC) of Compound 1 (calculated as the area under the curve from 0 to infinity (AUCinf)) by ≥80%, ≥50% to <80%, and ≥20% to <50%, respectively. In one embodiment, the "inducer of CYP3A4" is a "strong inducer of CYP3A4." Examples of strong inducers of CYP3A include, but are not limited to, carbamazepine, enzalutamide, mitotane, phenytoin, rifampin (also known as rifampicin), and St. John's wort. Examples of moderate inducers of CYP3A include, but are not limited to, bosentan, efavirenz, etravirine, and modafinil. Examples of weak inducers of CYP3A include, but are not limited to, armodafinil and rufinamide. See http://www.fda.gov/Drugs/DevelopmentApprovalProcess/DevelopmentResources/DrugInteractionsLabeling/ucm093664.htm#table3-3 (last visited Oct. 11, 2016).

As used herein, the term "inhibitor of CYP3A4" refers to a drug which causes CYP3A4 activity levels to decrease. Techniques suitable for the measurement of CYP3A4 activity are well known (see, for example, Sevrioukova I F, Poulos T L, 2015). Examples of CYP3A4 inhibitors include, but are not limited to, clarithromycin, grapefruit juice, and itraconazole. "Strong", "moderate", and "weak" inhibitors of CYP3A4 are drugs that increase the plasma AUC of Compound 1 (calculated as the area under the curve from 0 to infinity (AUCinf)) ≥5-fold, ≥2 to <5-fold, and ≥1.25 to <2-fold, respectively. In one embodiment the "inhibitor of CYP3A4" is a "strong inhibitor of CYP3A4." Examples of strong inhibitors of CYP3A include, but are not limited to, boceprevir, cobicistat, conivaptan, danoprevir and ritonavir, elvitegravir and ritonavir, grapefruit juice, indinavir and ritonavir, itraconazole, ketoconazole, lopinavir and ritonavir, paritaprevir and ritonavir and (ombitasvir and/or dasabuvir), posaconazole, ritonavir, saquinavir and ritonavir, telaprevir, tipranavir and ritonavir, troleandomycin, voriconazole, clarithromycin, diltiazem, idelalisib, nefazodone, and nelfinavir. Examples of moderate inhibitors of CYP3A include, but are not limited to, aprepitant, cimetidine, ciprofloxacin, clotrimazole, crizotinib, cyclosporine, dronedarone, erythromycin, fluconazole, fluvoxamine, imatinib, tofisopam, and verapamil. Examples of weak inhibitors of CYP3A include, but are not limited to, chlorzoxazone, cilostazol, fosaprepitant, istradefylline, ivacaftor, lomitapide, ranitidine, ranolazine, tacrolimus, and ticagrelor. See http://www.fda.gov/Drugs/DevelopmentApprovalProcess/DevelopmentResources/DrugInteractionsLabeling/ucm093664.htm#table3-2 (last visited Oct. 11, 2016).

As used herein, term "simultaneously treated with an inhibitor or inducer of CYP3A4" refers to a situation where a patient is subjected to a therapeutic regimen with an inhibitor or inducer of CYP3A4 while also subjected to a therapeutic regimen with Compound 1. In one embodiment, the patient is not simultaneously treated with an inhibitor or inducer of CYP3A4 and Compound 1 for longer than 1, 2, 3, 4, 5, 6, 7, 8, 9, 10, 11, 12, 13, 14, 15 or 16 weeks. In another embodiment, the patient is not simultaneously treated with an inhibitor or inducer of CYP3A4 and Compound 1 for longer than 1, 2, 3, 4, 5, 7, 10, or 12 months. In a certain embodiment, the patient is not simultaneously treated with an inhibitor or inducer of CYP3A4 and Compound 1 for longer than 3 months.

As used herein, the term "pharmaceutically acceptable salt" refers to salts that retain the biological effectiveness of the compound of this invention and which typically are not biologically or otherwise undesirable (Pharmaceutical Salts: Properties, Selection, and Use, $2^{nd}$ Revised Edition (2011) P. Heinrich Stahl, Camille G. Wermuth).

As used herein, a "pharmaceutical composition" comprises the compound of this invention, or a pharmaceutically acceptable salt thereof, and at least one pharmaceutically acceptable carrier, in a solid form (typically a gelatin capsule) suitable for oral administration. A list of pharmaceutically acceptable carriers can be found in Remington's Pharmaceutical Sciences. An example of a pharmaceutical composition suitable for use in the treatment or prevention of CAA, and its method of preparation, is provided herein in Example 10.

The term "a therapeutically effective amount" of a compound of the present invention refers to an amount of the compound of the present invention that will elicit inhibition of BACE-1 in a patient as evidenced by a reduction in CSF or plasma Aβ 1-40 levels relative to an initial baseline value.

For clarification, whenever a range is provided herein, said range is meant to include the endpoints. For example, a dose range between 30 and 50 mg per day comprises also doses of 30 and 50 mg per day.

| List of abbreviations | |
|---|---|
| Abbreviation | Description |
| ACN | acetonitrile |
| APP | amyloid precursor protein |
| Aβ | beta-amyloid peptide |
| aq. | aqueous |
| AUC | area under the curve, used to describe compound exposure |
| AUEC | area under the effect curve, used to describe effect over time |
| Aβ40 | beta-amyloid peptide 40 |
| BACE-1 | beta site APP cleaving enzyme-1 |
| BACE-2 | beta site APP cleaving enzyme-2 |
| BACE | beta site APP cleaving enzyme |
| $Boc_2O$ | di-tert-butyl dicarbonate |
| C | concentration |
| CB | clinical biochemistry |
| Cb | cerebellum sample |
| CI | confidence interval |
| conc. | concentrated |
| Cpd | compound |
| CPP | Chemical and Pharmaceutical Profiling (department) |
| CSF | Cerebrospinal fluid |
| CVP | cava vena puncture blood sample |
| d | day |
| DCM | dichloromethane |
| DDI | drug-drug interaction |
| DEA | diethylamine |
| DMF | N,N-dimethylformamide |
| DMSO | dimethylsulfoxide |
| EDC | 1-(3-dimethylaminopropyl)-3-ethylcarbodiimide hydrochloride |
| EDTA | ethylenediamine tetraethyl acetate |
| ESI | electrospray ionisation |
| EtOAc | ethyl acetate |
| FA | formic acid |
| Fbr | forebrain sample |
| g | gram/gravitational acceleration |
| h, hr | hour |
| HOAt | 1-hydroxy-7-azabenzotriazole |
| HPLC, LC | high-performance liquid chromatography, liquid chromatography |
| $IC_{50}$ | Inhibitory concentration 50 |
| kg | kilogram |
| LLOQ | lower limit of quantification |
| LSmeans | least squares means |
| MeOH | methanol |
| min | minute(s) |
| ml | milliliter |
| µl | microliter |
| µM | micromolar |
| µmol | micromoles |
| MC | methylcellulose |
| min | minute |
| MS | mass spectrometry |
| MSD | MesoScale Discovery (Supplier of immunoassay kits) |
| NaCl | sodium chloride |
| nM | nanomolar |
| nmol | nanomoles |
| NMR | nuclear magnetic resonance spectrometry |
| ns | not significant |
| PD | pharmacodynamic |
| PET | positron emission tomography |
| pg | picogram |
| PK | pharmacokinetic |
| pmol | picomoles |
| p.o. | per os |
| PVDF | polyvinylidene difluoride |

-continued

List of abbreviations

| Abbreviation | Description |
|---|---|
| q.d. or QD | quaque die |
| q.s. | quam satis |
| Rel. | relative |
| Rf | retention factor |
| rpm | revolutions per minute |
| Rt | retention time (min) |
| RT, rt | room temperature |
| SEM | standard error of the mean |
| SD | standard deviation or single dose |
| Stats | statistics |
| Swe | Swedish, indicating the presence of the "Swedish" double mutation in APP |
| $t_{1/2}$ | half-life |
| TBME | tert-butyl-methyl-ether |
| THF | tetrahydrofuran |
| tiss | tissue |
| TLC | thin layer chromatography |
| Tris | tris-hydroxymethyl(aminomethane) buffer substance |
| TBS | tris-buffered saline |
| TX-100 | triton-X-100 (detergent, CAS No. 9002-93-1) |
| UPLC | ultra performance liquid chromatography |
| vs | versus |
| wt | wild type |

EXAMPLES

The following Examples illustrate how Compound 1 may be prepared (Example 1) and formulated (Example 10); show the PK/PD effects of Compound 1 in an APOE4 transgenic mouse model (Example 2); show the PD effects of Compound 1 in a First in Human clinical study (Example 3); demonstrate the safety and tolerability of Compound 1 in a 3-month clinical study (Example 4); show the effect of ApoE4 genotype on Compound 1 PD response in the 3-month clinical study (Example 5); demonstrate the therapeutic effectiveness of Compound 1 in reducing CAA in the APP23 AD mouse model (Example 6); demonstrate the apparent therapeutic effectiveness of Compound 1 in reducing brain microhaemorrhage in aged APP23 mice (Example 7); show how the AUC of Compound 1 is affected when given in combination with a strong inhibitor or inducer of CYP3A4 (Example 8); and illustrate how a Compound 1 efficacy study for the treatment of CAA and the intracerebral haemorrhage associated therewith could be performed in ApoE4 homozygote at-risk patients (Example 9).

Example 1

Preparation of Compound 1

The preparation of Compound 1 is described in WO 2012/095469 A1 (Example 34). Compound 1 may also be prepared as described below.

NMR Methodology

Proton spectra are recorded on a Bruker 400 MHz ultra-shield spectrometer unless otherwise noted. Chemical shifts are reported in ppm relative to methanol (δ 3.31), dimethyl sulfoxide (δ 2.50), or chloroform (δ 7.29). A small amount of the dry sample (2-5 mg) is dissolved in an appropriate deuterated solvent (0.7 mL). The shimming is automated and the spectra obtained in accordance with procedures well known to the person of ordinary skill in the art.

General Chromatography Information

HPLC Method H1 ($Rt_{H1}$):
HPLC-column dimensions: 3.0×30 mm
HPLC-column type: Zorbax SB-C18, 1.8 µm
HPLC-eluent: A) water+0.05 Vol.-% TFA; B) ACN+0.05 Vol.-% TFA
HPLC-gradient: 30-100% B in 3.25 min, flow=0.7 ml/min LCMS Method H2 ($Rt_{H2}$):
HPLC-column dimensions: 3.0×30 mm
HPLC-column type: Zorbax SB-C18, 1.8 µm
HPLC-eluent: A) water+0.05 Vol.-% TFA, B) ACN+0.05 Vol.-% TFA
HPLC-gradient: 10-100% B in 3.25 min, flow=0.7 ml/min UPLCMS Method H3 ($Rt_{H3}$):
HPLC-column dimensions: 2.1×50 mm
HPLC-column type: Acquity UPLC HSS T3, 1.8 µm
HPLC-eluent: A) water+0.05 Vol.-% formic acid+3.75 mM ammonium acetate B) ACN+0.04 Vol.-% formic acid
HPLC-gradient: 2-98% B in 1.4 min, 98% B 0.75 min, flow=1.2 ml/min
HPLC-column temperature: 50° C.

LCMS Method H4 ($Rt_{H4}$):
HPLC-column dimensions: 3.0×30 mm
HPLC-column type: Zorbax SB-C18, 1.8 µm
HPLC-eluent: A) water+0.05 Vol.-% TFA; B) ACN+0.05 Vol.-% TFA
HPLC-gradient: 70-100% B in 3.25 min, flow=0.7 ml/min LCMS Method H5 ($Rt_{H5}$):
HPLC-column dimensions: 3.0×30 mm
HPLC-column type: Zorbax SB-C18, 1.8 µm
HPLC-eluent: A) water+0.05 Vol.-% TFA; B) ACN+0.05 Vol.-% TFA
HPLC-gradient: 80-100% B in 3.25 min, flow=0.7 ml/min LCMS Method H6 ($Rt_{H6}$):
HPLC-column dimensions: 3.0×30 mm
HPLC-column type: Zorbax SB-C18, 1.8 µm
HPLC-eluent: A) water+0.05 Vol.-% TFA; B) ACN+0.05 Vol.-% TFA
HPLC-gradient: 40-100% B in 3.25 min, flow=0.7 ml/min a) 2-Bromo-5-fluoro-4-triethylsilanyl-pyridine A solution of diisopropylamine (25.3 g, 250 mmol) in 370 ml THF was cooled with a dry-ice acetone bath at −75° C. BuLi (100 ml, 250 mmol, 2.5 M in hexanes) was added dropwise while maintaining the temperature below −50° C. After the temperature of the mixture had reached −75° C. again, a solution of 2-bromo-5-fluoropyridine (36.7 g, 208 mmol) in 45 ml THF was added dropwise. The mixture was stirred for 1 h at −75° C. Triethylchlorosilane (39.2 g, 260 mmol) was added quickly. The temperature stayed below −50° C. The cooling bath was removed and the reaction mixture was allowed to warm to −15° C., poured onto aq. NH$_4$Cl (10%). TBME was added and the layers were separated. The organic layer was washed with brine, dried with MgSO$_4$.H$_2$O, filtered and evaporated to give a brown liquid which was distilled at 0.5 mm Hg to yield the title compound as a slightly yellow liquid (b.p. 105-111° C.). HPLC: $Rt_{H4}$=2.284 min; ESIMS: 290, 292 [(M+H)$^+$, 1Br];
$^1$H-NMR (400 MHz, CDCl$_3$): 8.14 (s, 1H), 7.40 (d, 1H), 1.00-0.82 (m, 15H).

b) 1-(6-Bromo-3-fluoro-4-triethylsilanyl-pyridin-2-yl)-ethanone

A solution of diisopropylamine (25.4 g, 250 mmol) in 500 ml THF was cooled to −75° C. BuLi (100 ml, 250 mmol, 2.5 M in hexanes) was added dropwise while maintaining the temperature below −50° C. After the reaction temperature had reached −75° C. again, a solution of 2-bromo-5-fluoro-4-triethylsilanyl-pyridine (56.04 g, 193 mmol) in 60 ml THF was added dropwise. The mixture was stirred in a dry ice bath for 70 minutes. N,N-dimethylacetamide (21.87 g, 250 mmol) was added quickly, the reaction temperature rose to −57° C. The reaction mixture was stirred in a dry ice bath for 15 min and then allowed to warm to −40° C. It was poured on a mixture of 2M aq. HCl (250 ml, 500 mmol), 250 ml water and 100 ml brine. The mixture was extracted with TBME, washed with brine, dried over $MgSO_4.H_2O$, filtered and evaporated to give a yellow oil which was purified on a silica gel column by eluting with hexane/0-5% TBME to yield 58.5 g of the title compound as a yellow liquid. TLC (Hex/TBME 99/1): $R_f$=0.25; HPLC: $Rt_{H4}$=1.921 min; ESIMS: 332, 334 [(M+H)$^+$, 1Br]; $^1$H-NMR (400 MHz, $CDCl_3$): 7.57 (d, 1H), 2.68 (s, 3H), 1.00-0.84 (m, 15H).

c) (S)-2-(6-Bromo-3-fluoro-4-triethylsilanyl-pyridin-2-yl)-2-trimethylsilanyloxy-propionitrile At first, the catalyst solution was prepared by dissolving water (54 mg, 3.00 mmol) in 100 ml dry DCM (≤0.001% water). This wet DCM (44 ml, 1.32 mmol water content) was added to a well stirred solution of titanium(IV) butoxide (500 mg, 1.47 mmol) in 20 ml dry DCM. The resulting clear solution was refluxed for 1 h. This solution was then cooled to rt and 2,4-di-tert-butyl-6-{[(E)-(S)-1-hydroxymethyl-2-methyl-propylimino]-methyl}-phenol [CAS 155052-31-6] (469 mg, 1.47 mmol) was added. The resulting yellow solution was stirred at rt for 1 h. This catalyst solution (0.023 M, 46.6 ml, 1.07 mmol) was added to a solution of 1-(6-bromo-3-fluoro-4-triethylsilanyl-pyridin-2-yl)-ethanone (35.53 g, 107 mmol) and trimethylsilyl cyanide (12.73 g, 128 mmol) in 223 ml dry DCM. The mixture was stirred for 2 days and evaporated to give 47 g of the crude title compound as an orange oil. HPLC: $Rt_{H5}$=2.773 min; ESIMS: 431, 433 [(M+H)$^+$, 1Br]; $^1$H-NMR (400 MHz, $CDCl_3$): 7.46 (d, 1H), 2.04 (s, 3H), 1.00 (t, 9H), 1.03-0.87 (m, 15H), 0.20 (s, 9H).

d) (R)-1-Amino-2-(6-bromo-3-fluoro-4-triethylsilanyl-pyridin-2-yl)-propan-2-ol hydrochloride Borane dimethyl sulfide complex (16.55 g, 218 mmol) was added to a solution of crude (S)-2-(6-bromo-3-fluoro-4-triethylsilanyl-pyridin-2-yl)-2-trimethylsilanyloxy-propionitrile (47 g, 109 mmol) in 470 ml THF. The mixture was refluxed for 2 h. The heating bath was removed and the reaction mixture was quenched by careful and dropwise addition of MeOH. After the evolution of gas had ceased, aq. 6M HCl (23.6 ml, 142 mmol) was added slowly. The resulting solution was evaporated and the residue was dissolved in MeOH and evaporated (twice) to yield 44.5 g of a yellow foam, pure enough for further reactions. HPLC: $Rt_{H1}$=2.617 min; ESIMS: 363, 365 [(M+H)$^+$, 1Br]; $^1$H-NMR (400 MHz, $CDCl_3$): 7.93 (s, br, 3H), 7.53 (d, 1H), 6.11 (s, br, 1H), 3.36-3.27 (m, 1H), 3.18-3.09 (m, 1H), 1.53 (s, 3H), 0.99-0.81 (m, 15H).

e) (R)—N-(2-(6-bromo-3-fluoro-4-(triethylsilyl)pyridin-2-yl)-2-hydroxypropyl)-4-nitrobenzenesulfonamide To a solution of crude (R)-1-amino-2-(6-bromo-3-fluoro-4-triethylsilanyl-pyridin-2-yl)-propan-2-ol hydrochloride (43.5 g, 109 mmol) in 335 ml THF was added a solution of $NaHCO_3$ (21.02 g, 250 mmol) in 500 ml water. The mixture was cooled to 0-5° C. and a solution of 4-nitrobenzenesulfonyl chloride (26.5 g, 120 mmol) in 100 ml THF was added in a dropwise. The resulting emulsion was stirred overnight while allowing the temperature to reach rt. The mixture was extracted with TBME. The organic layer was dried with $MgSO_4.H_2O$, filtered and evaporated to give an orange resin which was purified on a silica gel column by eluting with Hexanes/10-20% EtOAc to yield 37.56 g of the title compound as a yellow resin. TLC (Hex/EtOAc 3/1): $R_f$=0.34; HPLC: $Rt_{H4}$=1.678 min; ESIMS: 548, 550 [(M+H)$^+$, 1Br]; $^1$H-NMR (400 MHz, DMSO-$d_6$): 8.40 (d, 2H), 8.06 (t, 1H), 7.97 (d, 2H), 7.45 (d, 1H), 5.42 (s, 1H), 3.23 (d, 2H), 1.44 (s, 3H) 0.97-0.81 (m, 15H); Chiral HPLC (Chiralpak AD-H 1213, UV 210 nm): 90% ee.

f) 6-Bromo-3-fluoro-2-[(S)-2-methyl-1-(4-nitro-benzenesulfonyl)-aziridin-2-yl]-4-triethylsilanyl-pyridine A solution of triphenylphosphine (21.55 g, 82 mmol) and (R)—N-(2-(6-bromo-3-fluoro-4-(triethylsilyl)pyridin-2-yl)-2-hydroxypropyl)-4-nitrobenzenesulfonamide (37.56 g, 69 mmol) in 510 ml THF was cooled to 4° C. A solution of diethyl azodicarboxylate in toluene (40% by weight, 38.8 g, 89 mmol) was added in a dropwise while maintaining the temperature below 10° C. The cooling bath was removed and the reaction mixture was stirred at rt for 1 h. The reaction mixture was diluted with approx. 1000 ml toluene and THF was removed by evaporation at the rotavap. The resulting toluene solution of crude product was pre-purified on a silca gel column by eluting with hexanes/5-17% EtOAc. Purest fractions were combined, evaporated and crystallized from TBME/hexane to yield 29.2 g of the title compound as white crystals. HPLC: $Rt_{H4}$=2.546 min; ESIMS: 530, 532 [(M+H)$^+$, 1Br]; $^1$H-NMR (400 MHz, $CDCl_3$): 8.40 (d, 2H), 8.19 (d, 2H), 7.39 (d, 1H), 3.14 (s, 1H), 3.02 (s, 1H), 2.01 (s, 3H) 1.03-0.83 (m, 15H); α[D] −35.7° (c=0.97, DCM).

g) 6-Bromo-3-fluoro-2-[(S)-2-methyl-1-(4-nitro-benzenesulfonyl)-aziridin-2-yl]-pyridine Potassium fluoride (1.1 g, 18.85 mmol) was added to a solution of 6-bromo-3-fluoro-2-[(S)-2-methyl-1-(4-nitrobenzenesulfonyl)-aziridin-2-yl]-4-triethylsilanyl-pyridine (5 g, 9.43 mmol) and AcOH (1.13 g, 9.43 mmol) in 25 ml THF. DMF (35 ml) was added and the suspension was stirred for 1 h at rt. The reaction mixture was poured onto a mixture of sat. aq. $NaHCO_3$ and TBME. The layers were separated and washed with brine and TBME. The combined organic layers were dried over $MgSO_4.H_2O$, filtered and evaporated to give a yellow oil which was crystallized from TBME/hexane to yield 3.45 g of the title compound as white crystals. HPLC: $Rt_{H6}$=2.612 min; ESIMS: 416, 418 [(M+H)$^+$, 1Br]; $^1$H-NMR (400 MHz, $CDCl_3$): 8.41 (d, 2H), 8.19 (d, 2H), 7.48 (dd, 1H), 7.35 (t, 1H), 3.14 (s, 1H), 3.03 (s, 1H), 2.04 (s, 3H); α[D] −35.7° (c=0.89, DCM).

h) (R)-2-[(R)-2-(6-Bromo-3-fluoro-pyridin-2-yl)-2-(4-nitrobenzenesulfonylamino)-propoxy]-3,3,3-trifluoro-2-methyl-propionic acid ethyl ester A solution of (R)-3,3,3-trifluoro-2-hydroxy-2-methyl-propionic acid ethyl ester (11.93 g, 64.1 mmol) in DMF (158 ml) was evacuated/flushed with nitrogen twice. A solution of KOtBu (6.21 g, 55.5 mmol) in DMF (17 ml) was added dropwise while maintaining a reaction temperature of ca 25° C. using cooling with a water bath. After 15 min solid 6-bromo-3-fluoro-2-[(S)-2-methyl-1-(4-nitro-benzenesulfonyl)-aziridin-2-yl]-pyridine (17.78 g, 42.7 mmol) was added and stirring was continued for 3 h. The reaction mixture was poured onto a mixture of 1M HCl (56 ml), brine and TBME. The layers were separated, washed with brine and TBME. The combined organic layers were dried over $MgSO_4.H_2O$, filtered and evaporated. The crude reaction product was purified via chromatography on silica gel (hexanes/25-33% TBME) to yield 16.93 g of the title compound as a yellow resin that was contaminated with an isomeric side-product (ratio 70:30 by $^1$H-NMR).

HPLC: $Rt_{H6}$=2.380 min; ESIMS: 602, 604 [(M+H)$^+$, 1Br]; $^1$H-NMR (400 MHz, $CDCl_3$): 8.32 (d, 2H), 8.07 (d, 2H), 7.46-7.41 (m, 1H), 7.30-7.23 (m, 1H), 6.92 (s, 1H), 3.39-4.30 (m, 2H), 3.95 (d, 1H), 3.84 (d, 1H), 1.68 (s, 3H), 1.56 (s, 3H), 1.40-1.34 (m, 3H)+ isomeric side-product.

i) (R)-2-[(R)-2-(6-Bromo-3-fluoro-pyridin-2-yl)-2-(4-nitro-benzenesulfonylamino)-propoxy]-3,3,3-trifluoro-2-methyl-propionamide A solution of (R)-2-[(R)-2-(6-bromo-3-fluoro-pyridin-2-yl)-2-(4-nitro-benzenesulfonylamino)-propoxy]-3,3,3-trifluoro-2-methyl-propionic acid ethyl ester (16.93 g, 28.1 mmol) in a NH$_3$/MeOH (7M, 482 ml) was stirred at 50° C. in a sealed vessel for 26 h. The reaction mixture was evaporated and the residue was crystallized from DCM to yield 9.11 g of the title compound as colorless crystals.

HPLC: Rt$_{H6}$=2.422 min; ESIMS: 573, 575 [(M+H)$^+$, 1Br]; $^1$H-NMR (400 MHz, CDCl$_3$): 8.33 (d, 2H), 8.06 (d, 2H), 7.42 (dd, 1H), 7.30-7.26 (m, 1H), 7.17 (s, br, 1H), 6.41 (s, 1H), 5.57 (s, br, 1H), 4.15 (m, 2H), 1.68 (s, 3H), 1.65 (s, 3H).

j) N—[(R)-1-(6-Bromo-3-fluoro-pyridin-2-yl)-2-((R)-1-cyano-2,2,2-trifluoro-1-methyl-ethoxy)-1-methyl-ethyl]-4-nitro-benzenesulfonamide A suspension of (R)-2-[(R)-2-(6-bromo-3-fluoro-pyridin-2-yl)-2-(4-nitro-benzenesulfonylamino)-propoxy]-3,3,3-trifluoro-2-methyl-propionamide (8.43 g, 14.70 mmol) and triethylamine (5.12 ml, 36.8 mmol) in 85 ml DCM was cooled to 0-5° C. Trifluoroacetic anhydride (2.49 ml, 17.64 mmol) was added dropwise over 30 min. Additional triethylamine (1.54 ml, 11.07 mmol) and trifluoroacetic anhydride (0.75 ml, 5.29 mmol) were added to complete the reaction. The reaction mixture was quenched by addition of 14 ml aqueous ammonia (25%) and 14 ml water. The emulsion was stirred for 15 min, more water and DCM were added and the layers were separated. The organic layer was dried with MgSO$_4$ H$_2$O, filtered and evaporated. Purification by column chromatography on a silica gel (hexanes/10-25% EtOAc) gave 8.09 g of the title compound as a yellow resin.

HPLC: Rt$_{H6}$=3.120 min; ESIMS: 555, 557 [(M+H)$^+$, 1Br]; $^1$H-NMR (400 MHz, CDCl$_3$): 8.35 (d, 2H), 8.11 (d, 2H), 7.50 (dd, 1H), 7.32 (dd, 1H), 6.78 (s, 1H), 4.39 (d 1H), 4.22 (d, 1H), 1.68 (s, 6H).

k) (2R,5R)-5-(6-Bromo-3-fluoro-pyridin-2-yl)-2,5-dimethyl-2-trifluoromethyl-5,6-dihydro-2H-[1,4]oxazin-3-ylamine A solution of N—[(R)-1-(6-bromo-3-fluoro-pyridin-2-yl)-2-((R)-1-cyano-2,2,2-trifluoro-1-methyl-ethoxy)-1-methyl-ethyl]-4-nitro-benzenesulfonamide (9.18 g, 16.53 mmol) and N-acetylcysteine (5.40 g, 33.10 mmol) in 92 ml ethanol was evacuated and flushed with nitrogen. K$_2$CO$_3$ (4.57 g, 33.1 mmol) was added and the mixture was stirred at 80° C. for 3 days. The reaction mixture was concentrated in vacuo to about ¼ of the original volume and partitioned between water and TBME. The organic layer was washed with 10% aq. K$_2$CO$_3$ solution, dried over Na$_2$SO$_4$, filtered and evaporated to give a yellow oil. Column chromatography on silica (hexanes/14-50% (EtOAc:MeOH 95:5)) gave 4.55 g of the title compound as an off-white solid.

HPLC: Rt$_{H2}$=2.741 min; ESIMS: 370, 372 [(M+H)$^+$, 1Br]; $^1$H-NMR (400 MHz, DMSO-d$_6$): 7.71 7.62 (m, 2H), 5.97 (s, br, 2H), 4.02 (d 1H), 3.70 (d, 1H), 1.51 (s, 3H), 1.47 (s, 3H).

l) (2R,5R)-5-(6-Amino-3-fluoro-pyridin-2-yl)-2,5-dimethyl-2-trifluoromethyl-5,6-dihydro-2H-[1,4]oxazin-3-ylamine A glass/stainless steel autoclave was purged with nitrogen, Cu$_2$O (0.464 g, 3.24 mmol), ammonia (101 ml, 25%, aq., 648 mmol, 30 equivalents) and (2R,5R)-5-(6-Bromo-3-fluoro-pyridin-2-yl)-2,5-dimethyl-2-trifluoromethyl-5,6-dihydro-2H-[1,4]oxazin-3-ylamine (8 g, 21.6 mmol) in ethylene glycol (130 ml) was added. The autoclave was closed and the suspension heated up to 60° C. and the solution was stirred for about 48 hours (max. pressure 0.7 bar, inside temperature 59-60° C.). The reaction mixture was diluted with ethyl acetate and water. The organic phase was washed with water and 4 times with 12% aq. ammonia and finally with brine, dried over sodium sulfate, filtered and evaporated. The crude product (7 g, containing some ethylen glycol, quantitative yield) was used in the next step without further purification.

HPLC: Rt$_{H3}$=0.60 min; ESIMS: 307 [(M+H)$^+$].

m) [(2R,5R)-5-(6-Amino-3-fluoro-pyridin-2-yl)-2,5-dimethyl-2-trifluoromethyl-5,6-dihydro-2H-[1,4]oxazin-3-yl]-carbamic acid tert-butyl ester A solution of (2R,5R)-5-(6-amino-3-fluoro-pyridin-2-yl)-2,5-dimethyl-2-trifluoromethyl-5,6-dihydro-2H-[1,4]oxazin-3-yl amine (6.62 g, 21.6 mmol), Boc$_2$O (4.72 g, 21.6 mmol) and Hünig's base (5.66 ml, 32.4 mmol) in dichloromethane (185 ml) was stirred at rt for 18 hours. The reaction mixture was washed with sat. aq. NaHCO$_3$ and brine. The aqueous layers were back extracted with dichloromethane and the combined organic layers were dried over sodium sulfate, filtered and evaporated to give a light green solid (14 g). The crude product was chromatographed over silicagel (cyclohexane:ethyl acetate 95:5 to 60:40) to afford 7.68 g of the title compound.

TLC (cyclohexane:ethyl acetate 3:1): R$_f$=0.21; HPLC: Rt$_{H3}$=1.14 min; ESIMS: 408 [(M+H)$^+$]; $^1$H-NMR (400 MHz, CDCl3): 11.47 (br. s, 1H), 7.23 (dd, J=10.42, 8.78 Hz, 1H), 6.45 (dd, J=8.78, 2.64 Hz, 1H), 4.50 (br. s, 2H), 4.32 (d, J=2.38 Hz, 1H), 4.10 (d, J=11.80 Hz, 1H), 1.69 (s, 3H, CH3), 1.65 (s, 3H, CH3), 1.55 (s, 9H).

n) ((2R,5R)-5-{6-[(3-Chloro-5-trifluoromethyl-pyridine-2-carbonyl)-amino]-3-fluoro-pyridin-2-yl}-2,5-dimethyl-2-trifluoromethyl-5,6-dihydro-2H-[1,4]oxazin-3-yl)-carbamic acid tert-butyl ester A mixture of [(2R,5R)-5-(6-amino-3-fluoro-pyridin-2-yl)-2,5-dimethyl-2-trifluoromethyl-5,6-dihydro-2H-[1,4] oxazin-3-yl]-carbamic acid tert-butyl ester (3.3 g, 8.12 mmol), 3-chloro-5-trifluoromethylpicolinic acid (2.2 g, 9.74 mmol), HOAt (1.99 g, 14.62 mmol) and EDC hydrochloride (2.33 g, 12.18 mmol) was stirred in DMF (81 ml) at rt for 48 hours. The reaction mixture was diluted with ethyl acetate and washed with water and brine, dried over sodium sulfate, filtered and evaporated. The crude product (12 g) was chromatographed over silicagel (cyclohexane to cyclohexane:ethyl acetate 1:1) to yield 5.2 g of the title compound.

TLC (silica, cyclohexane:ethyl acetate 3:1): R$_f$=0.47; HPLC: Rt$_{H3}$=1.40 min; ESIMS: 615, 616 [(M+H)$^+$, 1Cl]; $^1$H-NMR (400 MHz, CDCl3): 11.68 (s, 1H), 10.41 (s, 1H), 8.81 (dd, J=1.82, 0.69 Hz, 1 H), 8.45 (dd, J=8.91, 3.14 Hz, 1 H), 8.19 (dd, J=1.88, 0.63 Hz, 1 H), 7.59 (dd, J=9.79, 9.16 Hz, 1 H), 4.38 (d, J=2.13 Hz, 1 H), 4.18 (d, J=11.80 Hz, 1 H), 1.75 (s, 3H), 1.62 (s, 3H), 1.60 (s, 9H).

o) 3-Chloro-5-trifluoromethyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide A mixture of ((2R,5R)-5-{6-[3-chloro-5-trifluoromethyl-pyridine-2-carbonyl)-amino]-3-fluoro-pyridin-2-yl}-2,5-dimethyl-2-trifluoromethyl-5,6-dihydro-2H-[1,4]oxazin-3-yl)-carbamic acid tert-butyl ester (4.99 g, 8.13 mmol) and TFA (6.26 ml, 81 mmol) in dichloromethane (81 ml) was stirred at rt for 18 hours. The solvent was evaporated and the residue diluted with a suitable organic solvent, such as ethyl acetate and aq. ammonia. Ice was added and the organic phase was washed with water and brine, dried over sodium sulfate, filtered and evaporated to yield 3.78 g of the title compound.

HPLC: $Rt_{H3}$=0.87 min; ESIMS: 514, 516 [(M+H)$^+$, 1Cl]; $^1$H-NMR (400 MHz, DMSO-d$_6$): δ 11.11 (s, 1H), 9.06 (s, 1H), 8.69 (s, 1H), 8.13 (dd, J=8.8, 2.6 Hz, 1H), 7.80-7.68 (m, 1H), 5.88 (br. s, 2H), 4.12 (d, J=11.5 Hz, 1H), 3.72 (d, J=11.4 Hz, 1H), 1.51 (5, 3H), 1.49 (s, 3H).

Example 2

Acute PK/PD Dose-response Study of Compound 1 in APOE4-TR Mice

To investigate the effects of Compound 1 on APP metabolism in the human APOE4 context, PK/PD studies in transgenic mice carrying the human APOE4 allele were performed (mouse Apoe gene was replaced by human APOE4; APOE4-TR; (Knouff C et al., 1999)).

In this study, male and female APOE4-TR animals at the age of 3-5 months were treated acutely with Compound 1 at different doses (3, 10, 30 u mol/kg) and sacrificed at 4 h and 24 after treatment.

Animals

Male and female transgenic homozygous APOE4-TR (B6. 129P2-Apoe$^{tm3(APOE*4)Mae}$ N8, Taconic, Model 001549, 3-5 months old, n=48) were obtained from Taconic.

Dose Selection

Compound 1 was administered at 3, 10 and 30 μmol/kg.

Compound Form, Formulation and Dosing

Compound 1 was formulated as a suspension. Vehicle or compound was given by oral administration in a volume of 10 ml/kg once. Vehicle: 0.1% Tween80 in 0.5% Methylcellulose in water.

TABLE 2

Treatment Groups

| Treatment | Dose at 0 h | Day 1 | |
|---|---|---|---|
| | | n = +4 h | +24 h |
| A | Compound 1: 3 μmol/kg | 12 Sacrifice (n = 3 ♀ n = 3 ♂) | Sacrifice (n = 3 ♀ n = 3 ♂) |
| B | Compound 1: 10 μmol/kg | 12 Sacrifice (n = 3 ♀ n = 3 ♂) | Sacrifice (n = 3 ♀ n = 3 ♂) |
| C | Compound 1: 30 μmol/kg | 12 Sacrifice (n = 3 ♀ n = 3 ♂) | Sacrifice (n = 3 ♀ n = 3 ♂) |
| V | Vehicle (0.1% Tween 80, 0.5% MC) | 12 Sacrifice (n = 3 ♀ n = 3 ♂) | Sacrifice (n = 3 ♀ n = 3 ♂) |

Body Weight

Body weight was taken once before dosing.

Ex Vivo Samples and Sample Harvest Methodology

Blood samples were used to analyze whole blood compound levels and were obtained from trunk blood at the day of necropsy into EDTA Eppendorf tubes (Milian S A, CatNoTOM-14, Fisher Scientific, Wohlen, Switzerland), or into serum tubes (CB300Z, Sarstedt, Nümbrecht, Germany).

Plasma for amyloid-β (Aβ) analysis was collected by centrifugation of EDTA blood (8000 rpm/6800×g, 15 min, 4° C.) and collected into protein Lo-Bind Eppendorf tubes (003 0108.116, Eppendorf, Hamburg, Germany).

All blood/plasma/serum samples were frozen on dry ice and stored at −80° C. until analysis.

Brain was removed immediately after decapitation, rinsed with saline and sectioned sagitally down the midline. The left cerebellum was used to analyze compound level and was placed into a glass tube (Chromacol, 125×5-SV T051, Welwyn Garden City, United Kingdom), weighed and frozen in dry-ice, the left half of the forebrain (without olfactory bulb) was used for Aβ analysis, and was frozen on a metal plate on dry ice and placed into protein Lo-bind tube (003 0108.116, Eppendorf, Hamburg, Germany). The right brain was fixed in 4% paraformaldehyde, washed in PBS and then embedded in paraffin for possible future histological analyses.

Tails were collected at the end of the study and stored at −20° C.

TABLE 3

Analysis of compound levels

| | |
|---|---|
| Analytical method | HPLC/MS/MS |
| Brain homogenization method | Brain samples were mixed with 2 volumes of methanol/water (2/8 v/v) and homogenized using the Precellys ® device. |
| Sample preparation method | 30 μL of blood or brain homogenate were spiked with a generic internal standard (labetalol) and subsequently mixed with 200 μL acetonitrile (protein precipitation). A 1 μL aliquot of the supernatant was injected into the LC/MS/MS system for analysis. |
| MS | AB Sciex Triple Quad 5500 (AB Sciex, Brugg AG, Switzerland); Turbo Ion Electrospray Ionisation in positive ion mode. |
| MS/MS methods | 1. [Compound 1]: 508.2 Da [M + H]$^+$ → 139.1; 180.1; 375.1 Da/CE 85; 83; 43 eV 2. [Labetalol]: (Internal Standard) 329.0 [M + H]$^+$ → 294.0 and 311.2 Da/CE 26 and 19 eV |
| HPLC | Waters Acquity UPBINARY (Waters/Dättwil AG, Switzerland) |
| HPLC columns | Synergi Kinetex C18, 50*2.1 mm, 2.6 μm (Phenomenex, Torrance, CA, U.S.A.) |
| Buffer A // Buffer C | A: H$_2$O + 0.1% formic acid // B: methanol/acetonitrile (1/1) + 0.1% formic acid |
| Gradients | Pump 1: 0.0' 98% A, 2% B // 2.5' 10% A, 90% B // 2.6' 1% A, 99% B // 3' 98% A, 2% B // 4' 98% A, 2% B. Flow 0.0'-2.5' = 400 μl/min // 2.6'-4.0' = 500 μl/min |
| LLOQ | Compound 1: 0.4 ng/mL |
| Dynamic range: | 0.4 to 12500 ng/mL (Compound 1) |
| Calibration standards | Bias within the range −0.3 to −2.4% at the LLOQ and −12.3 to 14.4% at the other concentration levels |
| Quality Control | Bias within the range of −4.3 to 14.4% of all blood quality control samples. Bias within the range of 16.8 to 31.8% of all brain quality control samples: One brain QC was out of ±30% |
| Acceptance criteria in each run | Calibration standards: Bias within the range ±30% at the LLOQ and at ±20% at the other concentration levels. At least ¾ of the individual back-calculated values with at least one value at both extremes of the standard curve fulfilling the acceptance criteria. Quality Control samples: Bias within the range ±30% for at least ⅔ of the individual values. At least one value at each QC level fulfilling the acceptance criteria. |

Analysis of Aβ40 in Mouse Brain and Aβ40 and Abeta 42 in CSF

Brain Homogenization

Frozen mouse forebrains were weighed and homogenized in 9 volumes (w/v) of ice-cold TBS-Complete (20 mM Tris-HCl pH 7.4, 137 mM NaCl, 1× Complete [Protease Inhibitor Cocktail Tablets: 1 836 145, Roche Diagnostics GmbH, Penzberg, Germany]) by sonication (90% duty cycle, output control 5, 40-55 pulses, [Sonifier 450, Branson]). After homogenization several 50 μl aliquots were prepared for analysis and were stored at −80° C.

Preparation of Synthetic Abeta1-40 Solutions as Standards

Human Aβ peptide (1-40) trifluoroacetate salt (H 1194.1000, Bachem, Bubendorf, Switzerland) was used as calibration curve for Aβ1-40. It was solubilized in water-free DMSO (41647, Fluka) at a concentration of 1 mg/ml for approximately 30 min at room temperature (RT) and then visually checked for complete solubilization.

20×5 µl aliquots and 100 µl aliquots of the remaining solution were prepared in LoBind tubes (0030 108.094, Eppendorf, Hamburg, Germany), overlaid with nitrogen gas in order to protect the Aβ peptide from oxidation and stored at −80° C. For the calibration curves a 5 µl aliquot was used just once and then discarded.

Determination of Aβ40 in Mouse Brain

Endogenous Aβ40 in mice was determined with the Meso Scale Discovery (MSD) 96-well MULTI-ARRAY human/rodent (4G8) Aβ40 Ultrasensitive Assay (#K110FTE-3, Meso Scale Discovery, Gaithersburg, USA). The assay was performed according to the manufacturer's instructions except for the calibration curve and the sample preparations. TritonX-100 (TX-100) soluble Aβ40 was extracted from forebrain with 1% TX-100 using a 50 µl aliquot of each 1:10 forebrain homogenate, mixed with 50 µl 2% TX-100 in TBS complete (20 mM Tris-HCl pH 7.4, 137 mM NaCl, 1× Complete [Protease Inhibitor Cocktail Tablets: 1 836 145, Roche Diagnostics GmbH, Penzberg Germany]) to reach a final concentration of 1% TX-100 and a 1:20 forebrain dilution. The samples were incubated for 15 min on ice and vortexed every 5 min. The samples were ultra-centrifuged (100000×g, 4° C., 15 min) and 50 µl of the clear supernatants were transferred to fresh tubes. For the Aβ40 assay the supernatants were further diluted 1:5 in 3% Blocker A solution (from kit) to a final forebrain dilution of 1:100 and applied to the plate.

The calibration curve was prepared in a corresponding dilution of 1% Blocker A solution spiked with synthetic Aβ1-40 peptide (1.56-100 pg/ml) except for non-transgenic mouse brain samples: In this case, the calibration curve was prepared in a correspondingly diluted APP knockout mouse forebrain spiked with synthetic Aβ1-40 peptide (1.56-100 pg/ml). For all samples and standards 25 µl were applied per well. For each determination duplicate wells were done. The mean values from the duplicate wells were used for calculations. Since MSD did not provide quantification software, the relative units for samples and standards were imported into SOFTmax PRO 4.0 for calculation of standard curves and quantification of samples.

Results

APOE4-TR mice (mouse Apoe gene was replaced by human APOE4) were acutely treated with three different doses (3, 10 and 30 µmol/kg) of the BACE inhibitor Compound 1. Animals were sacrificed 4 h and 24 h after last the last dose and forebrains were separated. Concentrations of Aβ1-40 and Aβ1-42 for the various groups are summarized in FIGS. 1, 2 and 3; and Tablets 5, 6 and 7. The percent of reduction versus the vehicle treated group was calculated. All treatments resulted in a significant and dose-dependent Aβ40 reduction at 4 h and 24 h after the last dose, the effect ranged from 43-77% at 4 h and 20-66% at 24 h. For the two lower dose groups (3 and 10 µmol/kg) the Aβ40 lowering effect was significantly reduced at 4 h and 24, but substantially approximated baseline levels 24 h after the last dose. The high dose of Compound 1 (30 µmol/kg) showed an almost flat profile with 77-66% Aβ40 reduction over the whole 24 h time course.

TABLE 4

Effect of Compound 1 treatment on Aβ40 levels in APOE4-TR mouse brain (n = 6 (n = 3 males, n = 3 females))

| Dose | Dosing Regime | Time | Average Aβ40 brain (pmol/g) ± SD | % reduction vs vehicle | Significance vs vehicle | Mini AUEC (%) |
|---|---|---|---|---|---|---|
| Vehicle | Acute | 4/24 | 0.200 ± 0.034 | n.a. | n.a. | n.a. |
| 3 µmol/kg | Acute | 4 | 0.114 ± 0.024 | 43 | p < 0.0001 | 32 |
| 3 µmol/kg | Acute | 24 | 0.160 ± 0.033 | 20 | p < 0.05 | |
| 10 µmol/kg | Acute | 4 | 0.074 ± 0.014 | 63 | p < 0.0001 | 47 |
| 10 µmol/kg | Acute | 24 | 0.139 ± 0.041 | 31 | p < 0.001 | |
| 30 µmol/kg | Acute | 4 | 0.046 ± 0.006 | 77 | p < 0.0001 | 72 |
| 30 µmol/kg | Acute | 24 | 0.068 ± 0.021 | 66 | p < 0.0001 | | n.a.: not applicable,
vehicle: all vehicles combined

TABLE 5

Effect of Compound 1 treatment on Aβ40 levels in APOE4-TR mouse CSF (n = 6 (n = 3 males, n = 3 females))

| Dose | Dosing Regime | Time | Average Aβ40 CSF (pmol/ml) ± SD | % reduction vs vehicle | Significance vs vehicle | Mini AUEC (%) |
|---|---|---|---|---|---|---|
| Vehicle | Acute | 4/24 | 0.1826 ± 0.0956 | n.a. | n.a. | n.a. |
| 3 µmol/kg | Acute | 4 | 0.1308 ± 0.06381 | 28 | ns | 26 |
| 3 µmol/kg | Acute | 24 | 0.1402 ± 0.07911 | 23 | ns | |
| 10 µmol/kg | Acute | 4 | 0.07527 ± 0.03356 | 59 | p < 0.05 | 37 |
| 10 µmol/kg | Acute | 24 | 0.1565 ± 0.08348 | 14 | ns | |
| 30 µmol/kg | Acute | 4 | 0.02533 ± 0.01093 | 86 | p < 0.001 | 77 |
| 30 µmol/kg | Acute | 24 | 0.06083 ± 0.03445 | 67 | p < 0.01 | | n.a.: not applicable,
vehicle: all vehicles combined,
ns: not significant

TABLE 6

Effect of Compound 1 treatment on Abeta 42 levels in APOE4-TR mouse CSF (n = 6 (n = 3 males, n = 3 females))

| Dose | Dosing Regime | Time | Average Aβ42 CSF (pmol/ml) ± SD | % reduction vs vehicle | Significance vs vehicle | Mini AUEC (%) |
|---|---|---|---|---|---|---|
| Vehicle | Acute | 4/24 | 0.1174 ± 0.05610 | n.a. | n.a. | n.a. |
| 3 μmol/kg | Acute | 4 | 0.0524 ± 0.02173 | 55 | ns | 38 |
| 3 μmol/kg | Acute | 24 | 0.09317 ± 0.05304 | 21 | ns | |
| 10 μmol/kg | Acute | 4 | 0.02318 ± 0.00446 | 80 | $p < 0.01$ | 50 |
| 10 μmol/kg | Acute | 24 | 0.09438 ± 0.09019 | 20 | ns | |
| 30 μmol/kg | Acute | 4 | 0.0080 ± 0.00395 | 93 | $p < 0.001$ | 81 |
| 30 μmol/kg | Acute | 24 | 0.03717 ± 0.02438 | 68 | $p < 0.05$ | | n.a.: not applicable,
vehicle: all vehicles combined,
ns: not significant

PK data are shown in FIG. 4 and Table 7 at 4 h and 24 h for acute dosing in blood and brain. Exposure of Compound 1 over 24 h, expressed as $AUC_{0-24\ h}$ in blood and brain is summarized in Table 8. Compound 1 exposure in blood and brain was dose proportional and displayed the expected minor decline in compound level after 24 h, which again, was dose proportional. The compound exposure in brain was much higher than in blood. The brain blood ratio was similar for 3, 10 and 30 μmol/kg dose groups with 5, 3 and 4 at 4 h and 9, 4, and 3 at 24 h, respectively. The exposure ratio at 4 h/24 h was calculated which allows the comparison of the decline of compound exposure at the different doses (Table 7). Compound 1 had a moderate 2-5 fold exposure reduction, without big differences between the different doses and between blood and brain.

TABLE 7

Compound 1 levels in blood and brain of APOE4-TR mice (n = 6 (n = 3 males, n = 3 females)

| Treatment | Dosing | Time | Mean Blood (pmol/ml) ± SD | Exposure ratios 4 h/24 h (Blood) | Mean Brain (pmol/g) ± SD | Exposure ratios 4 h/24 h (Brain) |
|---|---|---|---|---|---|---|
| 3 μmol/kg | Acute | 4 | 105 ± 8 | 4.2 | 512 ± 216 | 2.4 |
| 3 μmol/kg | Acute | 24 | 25 ± 7 | | 210 ± 262 | |
| 10 μmol/kg | Acute | 4 | 317 ± 50 | 3.6 | 995 ± 151 | 3.1 |
| 10 μmol/kg | Acute | 24 | 88 ± 25 | | 324 ± 109 | |
| 30 μmol/kg | Acute | 4 | 985 ± 224 | 3.8 | 3409 ± 741 | 4.6 |
| 30 μmol/kg | Acute | 24 | 259 ± 68 | | 743 ± 267 | |

TABLE 8

Compound 1 $AUC_{0-24\ h}$ in blood and brain of APOE4-TR mice

| Treatment | Dosing | $AUC_{blood}$ (μM · h) | $AUC_{brain}$ (μmol/kg · h) |
|---|---|---|---|
| 3 μmol/kg | Acute | 1.56 | 8.67 |
| 10 μmol/kg | Acute | 4.86 | 15.83 |
| 30 μmol/kg | Acute | 14.92 | 49.82 |

AUC from 4 h and 24 h time points

The brain pharmacokinetic/pharmacodynamic relationship for the individual animals for all dose groups is shown in FIG. 5. There was a clear PK/PD relationship apparent for Compound 1; at low compound levels the Aβ reduction efficacy was minimal whereas at high compound levels a maximum efficacy effect was detected.

FIG. 6 displays the PK/PD relationship for the averaged values at the different doses. Again, the exposure dependent effect on Aβ reduction is apparent, with a clear minimal and maximal efficacy effect.

Conclusion

Studies presented in this experimental example demonstrate that Compound 1 is an orally-available, centrally active and potent inhibitor of BACE in vivo in APOE4-TR mice. APOE4-TR mice that express human APOE4 from the mouse endogenous Apoe locus were used to investigate PK/PD relationship of Compound 1. ApoE4 has been implicated to be a high risk factor for Alzheimer's disease and CAA.

The PK properties of Compound 1 in APOE4-TR mice did not differ to those observed in wildtype mice. A dose-dependent Compound 1 exposure in blood and brain, with much higher brain levels, was observed. Furthermore, the exposure decrease after 24 h was similar to that observed in wildtype mice. Compound 1 at 30 μmol/kg resulted in the maximal effect on Aβ reduction (>70%) in the brain of APOE4-TR, with similar extent lasting over 24 h for acute dosing. The PK/PD relationship was very comparable to wildtype mice and rats. There was a slightly lower maximal efficacy effect on Aβ reduction in the brain apparent in APOE4-TR mice at the highest dose (30 μmol/kg). This might be due to a lower clearance rate of amyloid-β observed in APOE-4 TR mice (Castellano J M et al., 2011).

Example 3

First-in-human Study

This study has been clinically completed and was a randomised, double-blind, placebo-controlled, single and multiple ascending oral dose study to primarily assess the safety and tolerability as well as the pharmacokinetics and pharmacodynamics of Compound 1 in healthy adult and elderly subjects. The purpose of this study was to determine the single and multiple maximum tolerated dose of Compound 1 and to assess the pharmacokinetic/pharmacodynamic (PK/PD) relationship using Aβ in CSF as primary PD biomarker.

In healthy elderly subjects ≥60 years of age, the highest tested doses of 750 mg single dose and 300 mg QD over two weeks were determined to be safe and tolerated. Pharmacodynamic assessments using Aβ concentrations in CSF as primary biomarker of drug action were also been applied in healthy elderly subjects. Dose-dependent lowering of Aβ40 concentrations was determined up to approximately 80% and 90% after single and multiple dosing, respectively (Tables 9 and 10, FIG. 7).

TABLE 9

Aβ40 in CSF - Summary of percent change from baseline across time

| Time (hours) | | Placebo | Single-dose | | | |
|---|---|---|---|---|---|---|
| | | | Cmpd 1 10 mg | Cmpd 1 90 mg | Cmpd 1 300 mg | Cmpd 1 750 mg |
| 12 h | N | 12 | 6 | 6 | 8 | 8 |
| | Mean (SD) | 1.6 (6.66) | −11.6 (8.31) | −14.2 (35.83) | −35.8 (16.40) | −36.2 (13.58) |
| | Median | 0.2 | −12.5 | −28.0 | −44.1 | −38.6 |
| | Min-Max | −7-16 | −21-1 | −36-58 | −54--13 | −53--10 |
| 24 h | N | 12 | 6 | 5 | 8 | 7 |
| | Mean (SD) | −2.2 (12.84) | −15.0 (10.21) | −44.8 (12.48) | −68.3 (10.65) | −67.4 (15.54) |
| | Median | −2.3 | −14.3 | −49.2 | −72.5 | −70.6 |
| | Min-Max | −22-22 | −31--4 | −55--25 | −79--52 | −82--36 |
| 34 h | N | 11 | 6 | 5 | 8 | 7 |
| | Mean (SD) | 5.1 (14.83) | −9.7 (14.72) | −50.0 (8.87) | −78.3 (4.75) | −79.1 (8.88) |
| | Median | 4.1 | −12.5 | −45.4 | −79.3 | −82.3 |
| | Min-Max | −22-29 | −25-10 | −60--41 | −84--69 | −87--60 |

TABLE 10

Aβ40 in CSF Summary of percent change from baseline on Day 15 (24 h post last dose)

| | Placebo | Multiple-dose | | | |
|---|---|---|---|---|---|
| | | Cmpd 1 10 mg | Cmpd 1 30 mg | Cmpd 1 90 mg | Cmpd 1 300 mg |
| N | 16 | 8 | 8 | 8 | 8 |
| Mean (SD) | −7.2 (6.04) | −60.1 (9.91) | −80.0 (3.89) | −88.2 (3.07) | −93.6 (0.61) |
| Median | −8.0 | −61.5 | −80.2 | −89.1 | −93.5 |
| Min; Max | −18; 2 | −77; −48 | −86; −76 | −92; −82 | −94; −93 |

Example 4

3-Month Dose-ranging Safety and Tolerability Study

Compound 1 was administered to healthy elderly subjects 60 years or over in a Phase I clinical dose-ranging safety and tolerability study. This study is listed in ClinicalTrials.gov under the NCT02576639 Identifier code.

This randomized, double-blind, placebo-controlled study had a parallel-group design and Compound 1 was administered as once-daily, oral doses to five treatment groups (Compound 1: 2 mg, 10 mg, 35 mg or 85 mg QD and placebo).

The primary purpose of this study was to expand on previous safety and tolerability data obtained over 2-week and 4-week duration in the first in human study and thereby allow initiation of future long-term efficacy trials in subjects at risk of AD and CAA. In addition, data relevant for Pharmacokinetic/Pharmacodynamic modeling was obtained in order to support dose selection decisions for future efficacy studies.

In this study, Compound 1 was found to be safe and tolerated at once-daily doses of 2, 10, 35 and 85 mg over three months. The pharmacodynamics effects of Compound 1 administration on CSF Aβ levels are shown in Table 11 and FIG. 8. The extent of Aβ lowering was stable over time with PD steady-state being reached after approximately 2-3 weeks.

TABLE 11

Aβ in CSF at month 3 - Analysis of percent change from baseline of Aβ38, Aβ40, and Aβ42

| Parameter | Treatment | N | LSmean (SE) | Difference (90% CI) Cmpd 1-Placebo | P-value |
|---|---|---|---|---|---|
| Aβ38 (pg/mL) | Placebo | 21 | −2.41 (1.430) | | |
| | Cmpd 1: 2 mg | 22 | −20.58 (1.397) | −18.17 (−21.49, −14.85) | <.001 |
| | Cmpd 1: 10 mg | 21 | −62.60 (1.430) | −60.18 (−63.54, −56.83) | <.001 |
| | Cmpd 1: 35 mg | 23 | −82.96 (1.366) | −80.55 (−83.83, −77.27) | <.001 |
| | Cmpd 1: 85 mg | 20 | −89.23 (1.470) | −86.81 (−90.22, −83.41) | <.001 |
| Aβ40 (pg/mL) | Placebo | 21 | −2.79 (1.389) | | |
| | Cmpd 1: 2 mg | 22 | −22.66 (1.355) | −19.87 (−23.09, −16.65) | <.001 |
| | Cmpd 1: 10 mg | 21 | −62.96 (1.388) | −60.18 (−63.43, −56.92) | <.001 |
| | Cmpd 1: 35 mg | 23 | −83.19 (1.325) | −80.41 (−83.59, −77.22) | <.001 |
| | Cmpd 1: 85 mg | 20 | −90.40 (1.429) | −87.62 (−90.93, −84.30) | <.001 |
| Aβ42 (pg/mL) | Placebo | 21 | −2.76 (1.310) | | |
| | Cmpd 1: 2 mg | 22 | −24.00 (1.277) | −21.24 (−24.28, −18.21) | <.001 |
| | Cmpd 1: 10 mg | 21 | −64.15 (1.308) | −61.39 (−64.47, −58.31) | <.001 |
| | Cmpd 1: 35 mg | 23 | −82.49 (1.250) | −79.73 (−82.73, −76.73) | <.001 |
| | Cmpd 1: 85 mg | 20 | −89.38 (1.348) | −86.62 (−89.76, −83.49) | <.001 |

Adjusted Lsmeans, difference in Lsmeans, 90% CI and P-value were obtained from an ANCOVA model with treatment as a fixed effect, and baseline AB level as covariat The pharmacokinetic parameters of Compound 1 following three months (91 days) daily dosing at 2, 10, 35 and 85 mg are shown in Table 12.

TABLE 12

Compound 1 pharmacokinetic parameters on Day 91

| | Cmax, ss (ng/mL) | | |
|---|---|---|---|
| | 10 mg qd. | 35 mg qd. | 85 mg qd. |
| Results Mean (CV %) | 80 (36) | 229 (33) | 602 (25) |

The Cmax,ss value represents the maximum plasma steady state concentration of Compound 1 following 91 days of once daily (qd) dosing at the specified dose. "CV %" represents the percentage coefficient of variation. Based on these results, a once daily dose of 15 mg of Compound 1 is expected to result in a plasma Cmax,ss value of between 70 and 170 ng/ml, and a once daily dose of 50 mg of Compound 1 is expected to result in a plasma Cmax,ss value of between 200 and 500 ng/ml.

Based on the data presented in Example 3 and 4, pharmacometric modelling predicts a daily dose of 50 mg to reach 80% CSF Aβ40 lowering and a dose of 15 mg to achieve 60% CSF Aβ40 lowering, in 90% of the subjects.

Example 5

Effect of ApoE4 Genotype on Response to Treatment with Compound 1

In the completed first-in-human and 3-month dose-ranging safety and tolerability clinical studies described in Examples 3 and 4, Aβ concentrations in CSF were obtained by means of lumbar punctures before the first dose (baseline) and respectively after 2 weeks and 3 months of multiple dosing. ApoE4 genotype also was obtained in the subjects who consented. The percent change from baseline in Aβ40 and Aβ42 concentrations was calculated in subjects who took the study treatment and had no major protocol deviation with potential impact on the evaluation of the pharmacodynamic effect. Tables 13 to 16 below provide summary statistics of the percent change from baseline by treatment group and ApoE genotype (E4 heterozygotes versus E4 non-carriers). Only one subject with CSF data was E4 homozygote (from the 3-month dose-ranging safety and tolerability study). This subject was treated with placebo and showed 11% decrease in both Aβ40 and Aβ42 concentrations and is not included in the tables below. The data shows that there is no difference in CSF Aβ40 and Aβ42 response to treatment with Compound 1 between ApoE4 carriers and non-carriers.

TABLE 13

Aβ40% change from baseline by ApoE genotype and Compound 1 treatment group at 3 months

| | | E4 heterozygotes | E4 non-carriers |
|---|---|---|---|
| Placebo | n | 9 | 8 |
| | Mean (SD) | −3 (7) | −2 (5) |
| | Median | −2 | −1 |
| | Range | −19; 9 | −13; 5 |
| Compound 1: 2 mg | n | 10 | 12 |
| | Mean (SD) | −21 (11) | −24 (9) |
| | Median | −18 | −22 |
| | Range | −46; −3 | −41; −10 |
| Compound 1: 10 mg | n | 3 | 15 |
| | Mean (SD) | −67 (7) | −64 (6) |
| | Median | −64 | −65 |
| | Range | −75; −61 | −73; −54 |
| Compound 1: 35 mg | n | 8 | 12 |
| | Mean (SD) | −84 (3) | −82 (5) |
| | Median | −85 | −83 |
| | Range | −88; −79 | −91; −72 |
| Compound 1: 85 mg | n | 2 | 17 |
| | Mean (SD) | −91 (0) | −91 (2) |
| | Median | −91 | −90 |
| | Range | −91; −91 | −94; −87 |

TABLE 14

Aβ42% change from baseline by ApoE genotype and Compound 1 treatment group at 3 months

| | | E4 heterozygotes | E4 non-carriers |
|---|---|---|---|
| Placebo | n | 9 | 8 |
| | Mean (SD) | −2 (4) | −2 (7) |
| | Median | −0 | −1 |
| | Range | −10; 4 | −12; 8 |

TABLE 14-continued

Aβ42% change from baseline by ApoE genotype and Compound 1 treatment group at 3 months

|  |  | E4 heterozygotes | E4 non-carriers |
|---|---|---|---|
| Compound 1: 2 mg | n | 10 | 12 |
|  | Mean (SD) | −23 (9) | −24 (9) |
|  | Median | −23 | −21 |
|  | Range | −44; −8 | −42; −12 |
| Compound 1: 10 mg | n | 3 | 15 |
|  | Mean (SD) | −66 (7) | −65 (5) |
|  | Median | −63 | −66 |
|  | Range | −74; −62 | −75; −56 |
| Compound 1: 35 mg | n | 8 | 12 |
|  | Mean (SD) | −83 (5) | −81 (6) |
|  | Median | −85 | −83 |
|  | Range | −89; −72 | −88; −68 |
| Compound 1; 85 mg | n | 2 | 17 |
|  | Mean (SD) | −88 (2) | −90 (2) |
|  | Median | −88 | −90 |
|  | Range | −90; −87 | −92; −84 |

TABLE 15

Aβ40% change from baseline by ApoE genotype and Compound 1 treatment group at 2 weeks in first-in-human clinical study

|  |  | E4 heterozygotes | E4 non-carriers |
|---|---|---|---|
| Placebo | n | 5 | 9 |
|  | Mean (SD) | −12 (3) | −6 (6) |
|  | Median | −11 | −4 |
|  | Range | −18; −9 | −17; 2 |
| Compound 1: 10 mg | n | 3 | 4 |
|  | Mean (SD) | −56 (10) | −59 (7) |
|  | Median | −53 | −61 |
|  | Range | −67; −49 | −64; −48 |
| Compound 1: 30 mg | n | 0 | 7 |
|  | Mean (SD) |  | −80 (4) |
|  | Median |  | −81 |
|  | Range |  | −86; −76 |
| Compound 1: 90 mg | n | 2 | 5 |
|  | Mean (SD) | −90 (2) | −89 (2) |
|  | Median | −90 | −90 |
|  | Range | −92; −89 | −91; −86 |
| Compound 1: 300 mg | n | 1 | 6 |
|  | Mean (SD) | −93 | −94 (1) |
|  | Median | −93 | −94 |
|  | Range | −93; −93 | −94; −93 |

TABLE 16

Aβ42% change from baseline by ApoE genotype and Compound 1 treatment group at 2 weeks in first-in-human clinical study

|  |  | E4 heterozygotes | E4 non-carriers |
|---|---|---|---|
| Placebo | n | 5 | 9 |
|  | Mean (SD) | −12 (4) | −4 (10) |
|  | Median | −9 | −4 |
|  | Range | −17; −8 | −18; 17 |
| Compound 1: 10 mg | n | 3 | 4 |
|  | Mean (SD) | −59 (11) | −58 (11) |
|  | Median | −64 | −59 |
|  | Range | −67; −47 | −70; −46 |
| Compound 1: 30 mg | n | 0 | 7 |
|  | Mean (SD) |  | −80 (6) |
|  | Median |  | −82 |
|  | Range |  | −86; −72 |
| Compound 1: 90 mg | n | 2 | 5 |
|  | Mean (SD) | −87 (2) | −86 (5) |
|  | Median | −87 | −87 |
|  | Range | −89; −86 | −90; −78 |

TABLE 16-continued

Aβ42% change from baseline by ApoE genotype and Compound 1 treatment group at 2 weeks in first-in-human clinical study

|  |  | E4 heterozygotes | E4 non-carriers |
|---|---|---|---|
| Compound 1: 300 mg | n | 1 | 6 |
|  | Mean (SD) | −89 | −92 (1) |
|  | Median | −89 | −91 |
|  | Range | −89; −89 | −93; −90 |

Example 6

Chronic Therapeutic Treatment of Plaque-bearing Male APP23 Mice with the BACE Inhibitor Compound 1 and Assessment of CAA Summary Compound 1 was chronically administered to APP23 transgenic mice at plaque bearing age (12 months) for 6 months, at two doses. Compared with a group that received vehicle only, the administration of Compound 1 at 0.03 g/kg food resulted in a slight, and the administration of 0.3 g/kg food resulted in a strong reduction of amyloid-β 40 and 42 compared to the vehicle group. The amount of Aβ in the mice brains was similar to the mice at baseline (12 months of age). Soluble Aβ in plasma and CSF were only significantly reduced in the high dose group. Co-localization/proximity analysis of CD31 and amyloid-beta positive immunoreactivity showed that brain blood vessels with 25-50% and 50-75% Aβ coverage were reduced by the high dose of Compound 1.

Methods

Animals and Dose Selection

Male transgenic, heterozygous APP23 (B6,D2-Tg (Thy1App)23Sdz (Sturchler-Pierrat C et al., 1997), 12-14 months old, n=64) were treated with 0.3 g/kg or at 0.03 g/kg Compound 1 in food pellets.

TABLE 17

| Treatment Groups | | |
|---|---|---|
| Group | Treatment | n = |
| A | Compound 1: 0.03 g/kg of food | 18 |
| B | Compound 1: 0.3 g/kg of food | 18 |
| C | Vehicle/Control | 18 |
| D | Baseline | 10 |

3 treatment groups, n = 18 mice per treatment group; 1 baseline group, n = 10

Ex Vivo Samples and Sample Harvest Methodology

Blood samples were used to analyze whole blood compound levels and were obtained from trunk blood at the day of necropsy into EDTA Eppendorf tubes (Milian S A, CatNoTOM-14, Fisher Scientific, Wohlen, Switzerland), or into serum tubes (CB300Z, Sarstedt, Nümbrecht, Germany).

Plasma for amyloid-β (Aβ) analysis was collected by centrifugation of EDTA blood (8000 rpm/6800×g, 15 min, 4° C.) and collected into protein Lo-Bind Eppendorf tubes (003 0108.116, Eppendorf, Hamburg, Germany).

All blood/plasma/serum samples were frozen on dry ice and stored at −80° C. until analysis.

Brain was removed immediately after decapitation, rinsed with saline and sectioned sagitally down the midline. The left half of the brain was used to analyze compound level and was placed into a glass tube (Chromacol, 125×5-SV T051, Welwyn Garden City, United Kingdom), weighed and frozen in dry-ice, the left half of the forebrain (without olfactory bulb) was used for Aβ analysis, and was frozen on a metal plate on dry ice and placed into protein Lo-bind tube (003 0108.116, Eppendorf, Hamburg, Germany).

Tails were collected at the end of the study and stored at −20° C.

Analysis of Compound Levels

Compound 1 levels in biological samples were quantified in blood and brain by liquid chromatography/tandem mass spectrometry (HPLC/MS/MS). Brain samples were mixed with 2 volumes of $KH_2PO_4$ buffer and homogenized using the Covaris® device. Either 30 μL of blood or brain homogenate were spiked with a structurally related internal standard and subsequently mixed with an at least 6-fold excess volume acetonitrile for protein precipitation. The supernatant was injected directly into the LC/MS/MS system for analysis.

TABLE 18

Instrumental conditions for blood and brain samples

| | |
|---|---|
| Analytical method | HPLC/MS/MS |
| MS | Sciex QTrap 5500; Heated Electrospray Ionisation in positive ion mode. |
| MS/MS methods | 514.0 Da [M + H]$^+$ 140.1/180.1 Da/CE 53/85 eV |
| HPLC | Flux Rheos Allegro (Thermo Scientific/Reinach BL, Switzerland) |
| HPLC columns | Phenomenex Kinetix C8 50*2.1 mm, 2.6 uM (Phenomenex, Torrance, CA, U.S.A.) |
| Buffer A // Buffer C | A: $H_2O$ + 0.1% formic acid // C: acetonitrile + 0.1% formic acid |
| Gradients | Pump 1: 0.0' 98% A, 2% C // 0.3' 70% A, 30% C // 7.5' 40% A, 60% C // 9.5' 1% A, 99% C // 10.25' 1% A, 99% C // 10.3' 99% A, 1% C // 12.3' 99% A, 1% C. Flow 300-350 μl/min |
| Acceptance criteria in each run | Calibration standards: Bias within the range ±20% at the LLOQ and at ±15% at the other concentration levels. At least ¾ of the individual back-calculated values with at least one value at both extremes of the standard curve fulfilling the acceptance criteria. Quality Control samples: Bias within the range ±30% for at least ⅔ of the individual values. At least one value at each QC level fulfilling the acceptance criteria. Dynamic range: 0.4 to 12500 ng/mL |

Analysis of Aβ40 and Aβ42 in Mouse Tissue
Brain Homogenization

Frozen mouse forebrains were weighed and homogenized in 9 volumes (w/v) of ice-cold TBS-Complete (20 mM Tris-HCl pH 7.4, 137 mM NaCl, 1× Complete [Protease Inhibitor Cocktail Tablets: 1 836 145, Roche Diagnostics GmbH, Penzberg, Germany]) by sonication (90% duty cycle, output control 5, 40-55 pulses, [Sonifier 450, Branson]). After homogenization several 50 μl aliquots were prepared for analysis and were stored at −80° C.

Preparation of Synthetic Abeta Solutions as Standards

Human Aβ peptide (1-40) trifluoroacetate salt (H 1194.1000, Bachem, Bubendorf, Switzerland) was used as calibration curve for Aβ1-40. It was solubilized in water-free DMSO (41647, Fluka) at a concentration of 1 mg/ml for approximately 30 min at room temperature (RT) and then visually checked for complete solubilization.

20×5 μl aliquots and 100 μl aliquots of the remaining solution were prepared in LoBind tubes (0030 108.094, Eppendorf, Hamburg, Germany), overlaid with nitrogen gas in order to protect the Aβ peptide from oxidation and stored at −80° C. For the calibration curves a 5 μl aliquot was used just once and then discarded.

Determination of Triton X-100 Soluble Abeta in APP23 Mouse Brain

Human Aβ40 and 42 in mice was determined with the Meso Scale Discovery (MSD) 96-well MULTI-ARRAY human/rodent (6E10) Aβ40/42 Assay (Meso Scale Discovery, Rockville, Md., USA) as described in [RD-2010-00284]. The assay was done according to the manufacturer's instructions except for the calibration curve and the sample preparations. TritonX-100 (TX-100) soluble Aβ40 and 42 was extracted from forebrain with 1% TX-100 using a 50 μl aliquot of each 1:10 forebrain homogenate, mixed with 50 μl 2% TX-100 in TBS complete (20 mM Tris-HCl pH 7.4, 137 mM NaCl, 1× Complete [Protease Inhibitor Cocktail Tablets: 1 836 145, Roche Diagnostics GmbH, Penzberg Germany]) to reach a final concentration of 1% TX-100 and a 1:20 forebrain dilution. The samples were incubated for 15 min on ice and vortexed every 5 min. The samples were ultra-centrifuged (100000×g, 4° C., 15 min) and 50 μl of the clear supernatants were transferred to fresh tubes. The supernatants were further diluted 1:5 in 3% Blocker A solution (from kit) to a final forebrain dilution of 1:100 and applied to the plate.

The calibration curve was prepared in a corresponding dilution of 1% Blocker A solution spiked with synthetic Aβ1-40 peptide (1.56-100 pg/ml) except for non-transgenic mouse brain samples: In this case, the calibration curve was prepared in a correspondingly diluted APP knockout mouse forebrain spiked with synthetic Aβ1-40 peptide (1.56-100 pg/ml). For all samples and standards 25 μl were applied per well. For each determination duplicate wells were done. The mean values from the duplicate wells were used for calculations. The relative units for samples and standards were imported into SOFTmax PRO 4.0 for calculation of standard curves and quantification of samples.

Determination of Formic Acid Soluble Abeta in APP23 Mouse Brain

Fifty microliter of forebrain homogenate was mixed with 116.6 μl 100% formic acid, resulting in a final formic acid concentration of 70%. Samples were stored on ice and vortexed every 5 minutes. For neutralization, 50 μl of the mixture were pipetted into a new tube, and 950 μl of 1 M Tris base, containing 1× Complete Protease inhibitor, was added. Tubes were stored at room temperature overnight and then centrifuged for 15 minutes at 14000 rpm in an Eppendorf Microzentrifuge at 4° C. From the top layer, 100 μl are removed and mixed with 100 μl of 3% Blocker A solution (part of the MesoScale assay kit). This sample was either directly applied to the assay plate (dilution 1:1332) or further diluted in 1% Blocker A solution.

Analysis of Aβ40 in Mouse CSF

Mouse CSF samples (3 μl) was diluted with 57 μL 1% Blocker A (MSD) and 25 μl were applied to the assay plate.

Analysis of Aβ40 in Mouse Plasma

Plasma samples (30 μl) were mixed with 30 μl of 3% Blocker A (MSD) and 25 μl were applied to the assay plate.

Analysis of Amyloid-beta Plaques and Vascular Endothelial Cells using Double Fluorescence Immunohistochemistry Amyloid plaques were stained using a rabbit anti-Aβ primary antibody (NT12) which recognizes the C-terminal part of the amyloid peptide (the antibody was raised as described in Schrader-Fischer G and Paganetti P A, 1996, and Schrader-Fischer G et al., 1997). The vascular endothelial cells were detected using a rat anti-CD31 antibody (reference DIA310) from Dianova GmbH (Hamburg, Germany). All stainings were performed using the fully automated instrument Ventana Discovery® Ultra (Roche Diagnostics Schweiz AG, Rotkreuz, Switzerland). All chemicals were provided by Roche Diagnostic.

All study animals were used and brain tissue sections of 3 micrometers were freshly cut and collected on Super-Frost+ slides. The tissues sections were de-paraffinized and rehydrated under solvent-free conditions (EZprep solution) followed by antigen retrieval (demasking) performed by heat retrieval cycles for 32 min in a EDTA based buffer (CC1 solution). Subsequently, slides were blocked for 4 min using the DISCOVERY Inhibitor (reference 07017944001 (Roche)). The primary antibody diluted at 1/10'000 in antibody diluent was manually added on tissue sections and incubated for 1 h at room temperature. A short post-fixation (glutaraldehyde at 0.05%) was performed before applying the multimer UltraMap-anti Rabbit HRP ready to use antibody (reference 05269717001) for 16 min.

Detection was performed using the DISCOVERY FITC® following the manufacturer's recommendations. Slides were then heat denaturated at 92° C. for 20 min before a manual application of the second primary antibody (rat anti-CD31 diluted at 1/1'000 in antibody diluent) and incubated for 1 h. Multimer UltraMap-anti-Rat HRP antibody (reference 05891884001) was used for 20 min to detect CD31 in combination with the DISCOVERY Rhodamine kit (reference 07259883001).

The slides were washed and mounted using Prolong® Gold antifade reagent (reference P36931, ThermoFisher, Switzerland) and further scanned with the Hamamatsu slide scanner instrument (NanoZoomer 2.0 HT, scanning software NDP-Scan Vers. 2.5, Hamamatsu Photonics France, Swiss Office, Solothurn, Switzerland) at the 40× objective. The scanning settings were as follows: the exposure time with the DAPI filter was set at 28.5 ms as well as for the FITC filter and TRITC filter (detection of Rhodamine).

Image Analysis

For the quantitative plaque and vessel-associated amyloid-beta evaluation based on image analysis, a proprietary image analysis platform (ASTORIA, Automated Stored Image Analysis) was developed based on MS Visual Studio 2010 and many functions from Matrox MIL V9 libraries (Matrox Inc, Quebec, Canada).

For the beta-amyloid plaque and vessel analysis, the following sequence of steps was performed:
Slides were scanned with Hamamatsu Nanozoomer at 40× magnification. For each fluorescence labelling (DAPI, FITC and TRITC), a separate image was created
Manually outline ROIs (regions of interest) for defining cortex in brain sections for Aβ plaque assessment on the green FITC channel image, then use the resulting outline also for the other two channel images (copy resulting xml files)
Run the in-house developed ImageScope (V12.1.0.5029, Aperio Inc., USA) plug-in for creation and export of *.tif image tiles (at 10× magnification) for each of the 3 fluorescence channels Image Batch Processing:
Obtain the combined true colour image (DAPI, FITC, TRITC) for each section through accessing each individual fluorescence channel image
Segmentation of valid sample (within outlined ROI) from black unstained background
Apply adaptive thresholding technique for segmentation of objects in green channel image (FITC-labeled Aβ plaques)

Specific for CD31
Segmentation of TRITC-labeled objects in red channel (specific for CD31 staining indicating blood vessels) through morphological tophat transformation (set at 10, 15 and 20) and thresholding, followed by size filtering (set at 15, 30, 50 and 200)—the combination of tophat 10 and size 15 was used for detailed analysis in this report
Generation of a ring around segmented vessels through dilations and subtraction of initial objects, to characterize valid range for Aβ assessment (adjacent to vessels), so-called "influence zone"
Classification of vessels according to ratio of NT12 positivity within previously determined influence zone CD31+NT12
Distribution of vessels (CD31 positive) into 3 size classes (small: <70 pixels, medium: 70 . . . 500 pixels, large: >500 pixels), and—for each vessel in each size class—classification into one of 5 classes of NT12 positivity
0% (no Aβ at vessel)
1 . . . 10% vessel-associated Aβ
11 . . . 25% vessel-associated Aβ
26 . . . 50% vessel-associated Aβ
51 . . . 75% vessel-associated Aβ
76 . . . 100% vessel-associated Aβ
Additional computation of
total NT12 signal within ROI
total CD31 signal within ROI
ratio of vessel-associated Aβ area, i.e. NT12 signal within total "influence zone" area as described above Results

TABLE 19

Compound 1 levels in brain and blood

| Dose (food pellet) | Time (after study start) | Tissue/ Fluid | Mean Amount (nM) ± SD |
|---|---|---|---|
| 0.03 g/kg | 2 months | Blood | 134 ± 49 |
| 0.3 g/kg | 2 months | Blood | 1802 ± 306 |
| 0.03 g/kg | 4 months | Blood | 406 ± 76 |
| 0.3 g/kg | 4 months | Blood | 2597 ± 346 |
| 0.03 g/kg | 6 months | Blood | 207 ± 28 |
| 0.3 g/kg | 6 months | Blood | 1861 ± 151 |
| 0.03 g/kg | 6 months | Brain | 556 ± 92 |
| 0.3 g/kg | 6 months | Brain | 6152 ± 1212 |

Blood concentrations of Compound 1 were determined after 2 and 4 months of dosing, and at the end of the study at 6 months. As shown in Table 19, there was constant exposure over the course of the study with acceptable variation between animals, 18% (8-36%) on average. Average Compound 1 blood concentration was 0.25±0.13 µM (mean±SD) for the 0.03 g/kg food dosing group, and 2.10±0.47 µM for the 0.3 g/kg dosing group, in good agreement with the 10-fold difference in compound dose. The exposure observed in this study roughly corresponded to a 5 and a 45 mg/kg daily oral dose of Compound 1. The brain/blood ratio, determined at the end of the experiment, was 2.7 for the 0.03 g/kg group, and 3.3 for the 0.3 g/kg group.

Biochemical Determination of APP Metabolites: Triton TX-100-soluble APP Metabolites from Mouse Brain Brain homogenates were extracted with 1% Triton X-100 in buffer and the resulting supernatant was considered to represent soluble forms of APP metabolites. In addition to Aβ40 and 42, we determined the N-terminal APP fragments sAPPα (direct cleavage product of α-secretase) and sAPPβ (Swe) (direct product of BACE1 cleavage). As shown in Table 24, soluble Aβ40 and 42 moderately (less than 2-fold) increase over the course of the study in the non-treated groups. Since no change in the APP expression and Aβ generation is known to happen during this age, it is assumed that the increased values in the vehicle group (18-20 mo old) arise from "leakage" out of the Aβ deposits (which increase several fold, see below). Also the values for the soluble APP metabolites sAPPα and β did not change significantly in the non-treated groups.

Mice treated with Compound 1 at the low dose (0.03 g Compound 1/kg food) showed a weak, not significant reduction of soluble Aβ40 and 42 and a moderate increase in sAPPα (Tables 20 and 21, FIGS. 9-11). Soluble APP (Swe) was significantly reduced by 29% (Tables 20 and 21, FIG. 12). Mice treated with the 0.3 g/kg dose of Compound 1 showed significant reduction of both Aβ and of sAPPβ (Swe), as well as a 3-fold increase in sAPPα (Tables 20 and 21, FIGS. 9-12).

Taken together, Compound 1 treatment resulted in a dose-dependent reduction of all soluble BACE1 cleavage products and in a dose dependent increase in sAPPα.

TABLE 20

Mouse brain Aβ40 and 42 levels following treatment with Compound 1

| Treatment group (n) | Aβ40 (ng/g tiss.) Mean ± SEM | Aβ42 (ng/g tiss.) Mean ± SEM | sAPPα (μg/g tiss.) Mean ± SEM | sAPPβ (Swe) (μg/g tiss.) Mean ± SEM |
|---|---|---|---|---|
| Baseline (10) | 152.3 ± 4.6 | 46.4 ± 1.3 | 207 ± 28 | 96.8 ± 7.9 |
| 0.03 g/kg food (16) | 190.2 ± 18.6 | 106.3 ± 10.0 | 435 ± 40 | 78.5 ± 4.0 |
| 0.3 g/kg food (13) | 120.8 ± 18.9 | 30.3 ± 4.2 | 1147 ± 36 | 24.6 ± 0.96 |
| Vehicle (18) | 213.8 ± 17.3 | 133.0 ± 17.7 | 302 ± 30 | 110.5 ± 6.4 |

TABLE 21

Comparison of changes between groups (Dunnett's multiple comparison test)

| Groups compared | Aβ40 | Aβ42 | sAPPα | sAPPβ (Swedish) |
|---|---|---|---|---|
| 0.03 g/kg vs vehicle | −4.6% not significant | −20.1% not significant | +44% not significant | −29.0% $p < 0.0001$ |
| 0.3 g/kg vs vehicle | −43.7% $p = 0.001$ | −77.3% $p < 0.0001$ | +279.8% $p < 0.0001$ | −77.7% $p < 0.0001$ |
| Vehicle vs baseline | +141% not significant | +186% $p < 0.0001$ | +31.4% not significant | +12.4% not significant |

APP Metabolites in CSF

CSF was collected from all mice at necropsy. Samples from the baseline group were stored for approximately 6 months, and analyzed together with the rest of the samples at the end of the study. Data in Table 22 and FIG. 13 show that CSF Aβ are highest in the baseline group (APP23 mice at 12 months of age), but drop in the vehicle group (APP23 mice at 18 months of age). Compared to this vehicle group, CSF Aβ40 is non-significantly reduced in the 0.03 g/kg food Compound 1 treatment group, and significantly in the 0.3 g/kg food Compound 1 treatment group. The reason for the high baseline values is currently not known. It is hypothesized that this is an effect of long term storage, when dissociation of oligomeric forms of Aβ may lead to higher monomeric concentrations. CSF Aβ, more than Triton TX-100 solubilized Aβ from brain extracts, represents the steady-state concentration of soluble amyloid-β that directly responds to changes in Aβ generation. The small and non-significant treatment effects at the low Compound 1 dose (−4.6 to −20%), as well as the pronounced and significant effect at the high Compound 1 doses (−43.7 to −77%), are very comparable between the soluble Aβ species isolated from the brain tissue and Aβ40 in CSF.

TABLE 22

Summary of results for CSF Aβ40

| Treatment group (n) | Aβ40 (ng/ml) Mean ± SEM | Change vs vehicle | significance |
|---|---|---|---|
| Baseline (10) | 48.8 ± 3.15 | +42.7% | $p < 0.0001$ |
| 0.03 g/kg food (16) | 31.2 ± 2.11 | −8.6% | not significant |
| 0.3 g/kg food (12) | 15.6 ± 1.8 | −54.3% | $p < 0.0001$ |
| Vehicle (18) | 34.2 ± 1.16 | n.a. | n.a. |

Formic Acid Soluble Amyloid-beta Peptides in Forebrain

Treatment effects of Compound 1 on deposited forms of amyloid-β in the APP23 mouse brains were investigated after extraction of insoluble Aβ species with formic acid. As shown in Tables 23 and 24 and FIGS. 14 to 17, a massive increase of deposited Aβ was observed in the vehicle group, compared to baseline. Amyloid-β42 increased more than Aβ40 (Aβ42/40 ratio increased by 55% in the vehicle group), in agreement with its higher aggregation propensity. Aβ40 and Aβ42 showed a reduction after treatment with the low dose of Compound 1 of around 17%, compared to vehicles, but it did not reach statistical significance. The Aβ42/40 ratio of the extracted material did not change. Strong and highly significant (around 80% vs vehicle) reduction of deposited Aβ40 and 42 was observed in the high Compound 1 treatment group, and the Aβ42/40 ratio returned to baseline value of 0.07. In summary, the treatment with the high dose of Compound 1 almost completely blocked the increase of amyloid β in APP23 mice.

TABLE 23

Formic acid soluble amyloid-beta peptides in mouse forebrain

| Treatment group (n) | Aβ40 (μg/g) Mean ± SEM | Aβ42 (μg/g) Mean ± SEM | Total Aβ Mean ± SEM | Ratio 42/40 Mean ± SEM |
|---|---|---|---|---|
| Baseline (10) | 22.7 ± 3.3 | 1.45 ± 0.2 | 24.2 ± 2.4 | 0.068 ± 0.0097 |
| 0.03 g/kg food (16) | 170.9 ± 14.8 | 18.6 ± 1.9 | 189.5 ± 15.5 | 0.103 ± 0.0198 |
| 0.3 g/kg food (12) | 43.7 ± 5.0 | 3.1 ± 0.5 | 46.8 ± 5.4 | 0.068 ± 0.0155 |
| Vehicle (18) | 208.7 ± 17.6 | 22.2 ± 2.0 | 231.0 ± 19.5 | 0.106 ± 0.0136 |

TABLE 24

Group comparison and statistics (Dunnett's multiple comparison test)

| Groups compared | Aβ40 | Aβ42 | Total Aβ | Aβ42/40 ratio |
|---|---|---|---|---|
| 0.03 g/kg vs vehicle | −18.1% not significant | −16.3% not significant | −17.9% not significant | −2.5% not significant |

TABLE 24-continued

Group comparison and statistics (Dunnett's multiple comparison test)

| Groups compared | Aβ40 | Aβ42 | Total Aβ | Aβ42/40 ratio |
|---|---|---|---|---|
| 0.3 g/kg vs vehicle | −79.2% p < 0.0001 | −86.2% p < 0.0001 | −79.8% p < 0.0001 | −36.5% p < 0.0001 |
| Vehicle vs baseline | +820% p < 0.0001 | +1348% p < 0.0001 | +854% p < 0.0001 | +55% p < 0.0001 |

Effects on CAA

Aged APP23 animals display a robust extent of CAA, which was assessed by co-localization/proximity analysis of CD31 and amyloid-beta (NT12) positive immunoreactivity in co-immunofluorescence. CD31, also known as platelet endothelial cell adhesion molecule-1 (PECAM-1) is a type I integral membrane glycoprotein that is expressed at high levels on early and mature endothelial cells, platelets, and most leukocyte subpopulations. CD31 immunoreactivity is often used as a marker to visualize the endothelial cells of the brain blood vessels. For quantitative image analysis CD31 positive structures of the cortex were detected, influence zones around these structures were defined and Aβ within these influence zones were quantified. The total number of CD31+ vessels (normalized to total sample area) and the % of CD31+ vessels with different Aβ coverage were assessed (Table 25). The Aβ coverage of CD31+ vessels was separated into different categories: 0%, 1-10%, 10-25%, 25-50%, 50-75% and >75% Aβ coverage (Table 25). Additionally, all CD31+ vessels with >10% Aβ coverage were summed up (Table 25), as this would ensure to eliminate potential unspecific Aβ signals. The CAA frequency was calculated (CD31+ vessels with >10% Aβ coverage normalized to total sample area) (Table 31) as described by Winkler D T et al., 2001, with the difference that computer-assisted quantitative image analysis was used to assess CD31+ vessels affected by A. Finally, the total vessel-associated Aβ area was analyzed and normalized to the total CD31+ area (Table 31).

In APP23 mice, the percentage of Aβ affected vessels (>10% Aβ coverage) increased approximately 2-fold with mouse age and this increase was reduced by the high dose of Compound 1 treatment (Table 28, FIG. 20). The low dose of Compound 1 treatment did not reduce the percentage of Aβ affected vessels (vessels with >10% Aβ coverage). Mostly vessels with 25-50% and 50-75% Aβ coverage were reduced by the high dose Compound 1 treatment than vessels with other percentage of Aβ coverage (Table 28). Importantly, the number of total CD31+ vessels was similar in all treatment groups (Table 25, FIG. 18). Interestingly, only the low dose of Compound 1 significantly reduced the number of vessels with no Aβ coverage and concurrently increased the number of vessels with a low Aβ coverage (<10% Aβ coverage), while no age-dependent difference and no treatment effect of the high Compound 1 dose was apparent on these parameters (Table 28).

In addition, the CAA frequency increased with mouse age approximately 2-fold and this increase was reduced by the high dose of Compound 1 treatment (Table 34, FIG. 22). Again, there was no significant treatment effect for the low dose of Compound 1. The analysis of the total vessel-associated Aβ area normalized to total CD31+ area revealed a small treatment effect relative to vehicle at the high dose of Compound 1, although this effect was not statistically significant, while the age-dependent increase of this parameter was slightly significant (Table 34, FIG. 24).

To distinguish between CAA-type 1 and CAA-type 2 the vessel sizes and their respective Aβ coverage were determined (small+medium and large) (Table 26, Table 27) in a manner similar to that described above. Aged APP23 animals display a robust extent of CAA in small, medium and large vessels, which represent presumably capillaries, cortical arteries and leptomeningeal vessels, respectively. In APP23 mice, the percentage of Aβ affecting small+medium-sized vessels (>10% Aβ coverage) increased approximately 2-fold with mouse age and this increase was reduced by the high dose of Compound 1 treatment (Tables 26 and 29, FIG. 21). The low dose of Compound 1 treatment did not reduce the percentage of Aβ affected small+medium-sized vessels (vessels with >10% Aβ coverage). Mostly small+medium-sized vessels with 10-25%, 25-50% and 50-75% Aβ coverage were reduced by the high dose Compound 1 treatment, rather than vessels with other percentage of Aβ coverage (Table 29). Importantly, the number of total CD31+ small+medium-sized vessels was similar in all treatment groups (Table 26, FIG. 19). There was no treatment effect with the high and low dose of Compound 1 in large vessels observed, despite there was an age-dependent increase in these parameters (Tables 27 and 30, FIG. 21). Again, the number of total CD31+ large-sized vessels was similar in all treatment groups (Table 27, FIG. 19)

In addition, the CAA frequency of small+medium-sized vessels increased with mouse age approximately 2-fold and this increase was reduced by the high dose of Compound 1 treatment (Table 32, Table 35, FIG. 23). Again, there was no significant treatment effect for the low dose of Compound 1. The analysis of the total vessel-associated Aβ area normalized to total CD31+ small+medium-sized vessel area revealed a significant treatment effect relative to vehicle at the high dose of Compound 1 (Table 32, Table 35, FIG. 25). There was no treatment effect on CAA frequency in large vessels with the high and low dose of Compound 1 observed (Table 33, Table 36, FIG. 25).

The weak and sometimes not significant effects at the low dose of Compound 1 are not surprising, since high doses of BACE inhibitors are needed to achieve significant BACE-1 inhibition in mouse models carrying the "Swedish" mutation compared to wtAPP transgenic mice.

TABLE 25

Effect of Compound 1 treatment on CAA, amyloid-beta in CD31-positive vessels, normalized to total sample area or to total number of CD31+ vessels (values are mean and SEM)

| Treatment group (n) | Total number CD31+ vessels (normalized to total sample area, *10$^5$) | % of vessels with | | | | | | |
|---|---|---|---|---|---|---|---|---|
| | | 0% Aβ | 1-10% Aβ | 10-25% Aβ | 25-50% Aβ | 50-75% Aβ | >75% Aβ | >10% Aβ |
| Baseline (10) | 6.57 ± 0.36 | 77.4 ± 2.54 | 15 ± 2.3 | 2.56 ± 0.28 | 2.38 ± 0.3 | 1.41 ± 0.24 | 1.18 ± 0.24 | 7.53 ± 0.91 |
| 0.03 g/kg food (16) | 6.52 ± 0.4 | 60.3 ± 3.49 | 23.2 ± 2.6 | 5.65 ± 0.8 | 4.06 ± 0.44 | 3.13 ± 0.35 | 3.7 ± 0.55 | 16.5 ± 0.76 |
| 0.3 g/kg food (13) | 6.46 ± 0.37 | 79.2 ± 1.63 | 11 ± 1.1 | 2.87 ± 0.21 | 2.65 ± 0.25 | 2.12 ± 0.24 | 2.19 ± 0.36 | 9.82 ± 0.85 |
| Vehicle (18) | 6.53 ± 0.39 | 72.5 ± 1.25 | 12.7 ± 0.92 | 4.23 ± 0.26 | 4.12 ± 0.25 | 3.14 ± 0.24 | 3.3 ± 0.29 | 14.8 ± 0.76 |

TABLE 26

Effect of Compound 1 treatment on CAA, amyloid-beta in small + medium CD31-positive vessels, normalized to total or small + medium CD31+ vessel numbers (values are mean and SEM)

| Treatment group (n) | Number of small + medium CD31+ vessels (normalized to total CD31 positive small + medium vessel numbers in %) | % of small + medium vessels with | | | | | | |
|---|---|---|---|---|---|---|---|---|
| | | 0% Aβ | 1-10% Aβ | 10-25% Aβ | 25-50% Aβ | 50-75% Aβ | >75% Aβ | >10% Aβ |
| Baseline (10) | 98.3 ± 0.17 | 78.6 ± 2.51 | 14.9 ± 2.29 | 2.37 ± 0.26 | 2.04 ± 0.26 | 1.07 ± 0.15 | 1.12 ± 0.22 | 6.59 ± 0.78 |
| 0.03 g/kg food (15) | 98.1 ± 0.17 | 63.7 ± 2.83 | 22.3 ± 2.65 | 4.86 ± 0.48 | 3.55 ± 0.35 | 2.5 ± 0.31 | 3.11 ± 0.44 | 14.0 ± 1.01 |
| 0.3 g/kg food (13) | 98.5 ± 0.12 | 80.2 ± 1.61 | 10.8 ± 1.12 | 2.75 ± 0.20 | 2.38 ± 0.25 | 1.73 ± 0.21 | 2.07 ± 0.33 | 8.95 ± 0.8 |
| Vehicle (18) | 98.5 ± 0.144 | 73.5 ± 1.23 | 12.7 ± 0.92 | 4.2 ± 0.26 | 3.89 ± 0.23 | 2.67 ± 0.19 | 3.12 ± 0.27 | 13.9 ± 0.69 |

One animal has been removed in the 0.03 g/kg treatment group due to technical reasons in the vessel size evaluation.

TABLE 27

Effect of Compound 1 treatment on CAA, amyloid-beta in large CD31-positive vessels, normalized to total or large CD31+ vessel numbers (values are mean and SEM)

| Treatment group (n) | Number of large CD31+ vessels (normalized to total CD31 positive vessel numbers in %) | % of large vessels with | | | | | | |
|---|---|---|---|---|---|---|---|---|
| | | 0% Aβ | 1-10% Aβ | 10-25% Aβ | 25-50% Aβ | 50-75% Aβ | >75% Aβ | >10% Aβ |
| Baseline (10) | 1.73 ± 0.17 | 15.5 ± 3.34 | 27 ± 4.16 | 14.2 ± 2.03 | 21.1 ± 1.95 | 17.8 ± 4.12 | 4.38 ± 1.5 | 57.5 ± 5.74 |
| 0.03 g/kg food (15) | 1.89 ± 0.17 | 9.14 ± 9.14 | 17.4 ± 1.63 | 11.2 ± 1.68 | 17.5 ± 2.63 | 27.7 ± 1.97 | 17.0 ± 2.92 | 73.5 ± 3.4 |
| 0.3 g/kg food (13) | 1.49 ± 0.12 | 10.3 ± 1.56 | 21.6 ± 2.31 | 9.48 ± 1.85 | 20.6 ± 3.66 | 28.8 ± 3.3 | 9.27 ± 2.77 | 68.1 ± 3.03 |
| Vehicle (18) | 1.52 ± 0.144 | 11.2 ± 1.69 | 14.6 ± 1.63 | 7.02 ± 1.33 | 19.3 ± 2.04 | 32.7 ± 2.79 | 15.2 ± 2.44 | 74.2 ± 2.47 |

One animal has been removed in the 0.03 g/kg treatment group due to technical reasons in the vessel size evaluation.

TABLE 28

Treatment effects and statistics for normalized amyloid-beta in CD31-positive vessels (Dunnett's multiple comparison test)

| | % of vessels with | | | | | | |
|---|---|---|---|---|---|---|---|
| Groups compared | 0% Aβ | 1-10% Aβ | 10-25% Aβ | 25-50% Aβ | 50-75% Aβ | >75% Aβ | >10% Aβ |
| 0.03 g/kg vs vehicle | −17% p < 0.001 | +82% p < 0.001 | +34% n.s. | −2% n.s. | 0% n.s. | +12% n.s. | +12% not significant |
| 0.3 g/kg vs vehicle | +9% n.s. | −13% n.s. | −32% n.s. | 36% p < 0.01 | −33% p < 0.05 | −34% n.s. | −34% p < 0.01 |
| Vehicle vs baseline | −6% n.s. | +18% n.s. | +65% n.s. | +73% p < 0.01 | +123% p < 0.001 | +179% p < 0.01 | +96% p < 0.001 | n.s.: not significant

TABLE 29

Treatment effects and statistics for normalized amyloid-beta in small + medium CD31-positive vessels (Dunnett's multiple comparison test)

| | % of small + medium vessels with | | | | | | |
|---|---|---|---|---|---|---|---|
| Groups compared | 0% Aβ | 1-10% Aβ | 10-25% Aβ | 25-50% Aβ | 50-75% Aβ | >75% Aβ | >10% Aβ |
| 0.03 g/kg vs vehicle | −13% p < 0.005 | +76% p < 0.001 | +16% n.s. | −9% n.s. | −6% n.s. | 0% n.s. | +1% n.s. |
| 0.3 g/kg vs vehicle | +9% n.s. | −15% n.s. | −35% p < 0.005 | −39% p < 0.001 | −35% p < 0.05 | −34% n.s. | −36% p < 0.001 |
| Vehicle vs baseline | −6% n.s. | +17% n.s. | +44% p < 0.005 | +91% p < 0.001 | +150% p < 0.001 | +179% p < 0.001 | +111% p < 0.001 | n.s.: not significant

TABLE 30

Treatment effects and statistics for normalized amyloid-beta in large CD31-positive vessels (Dunnett's multiple comparison test)

| | % of vessels with | | | | | | |
|---|---|---|---|---|---|---|---|
| Groups compared | 0% Aβ | 1-10% Aβ | 10-25% Aβ | 25-50% Aβ | 50-75% Aβ | >75% Aβ | >10% Aβ |
| 0.03 g/kg vs vehicle | −18% n.s. | +19% n.s. | +60% n.s. | −9% n.s. | −15% n.s. | +12% n.s. | −1% n.s. |
| 0.3 g/kg vs vehicle | −8% n.s. | +48% n.s. | +35% n.s. | +7% n.s. | −12% n.s. | −36% n.s. | −8% n.s. |
| Vehicle vs baseline | −28% n.s. | −46% p < 0.005 | −51% p < 0.05 | −9% n.s. | +84% p < 0.005 | +247% p < 0.05 | +29% p < 0.01 | n.s.: not significant

TABLE 31

Effect of Compound 1 treatment on CAA frequency and amyloid-beta in CD31-positive vessels, normalized to total sample area or total CD31+ area (values are mean and SEM)

| Treatment group (n) | Number vessels with >10% Aβ | CAA Frequency (number vessels with >10% Aβ normalized to sample area, *$10^7$) | Total vessel-associated NT12 area (normalized to total CD31+ area) |
|---|---|---|---|
| Baseline (10) | 147 ± 15.5 | 46 ± 4.8 | 0.36 ± 0.06 |
| 0.03 g/kg food (16) | 319 ± 22.2 | 94 ± 6.5 | 0.65 ± 0.07 |
| 0.3 g/kg food (13) | 217 ± 23.6 | 70 ± 7.6 | 0.47 ± 0.04 |
| Vehicle (18) | 354 ± 29.8 | 98 ± 8.3 | 0.57 ± 0.07 |

TABLE 32

Effect of Compound 1 treatment on CAA frequency and amyloid-beta in small + medium CD31-positive vessels, normalized to total sample area or total small + medium CD31 + vessel area (values are mean and SEM)

| Treatment group (n) | Number small + medium vessels with >10% Aβ | CAA Frequency (number small + medium vessels with >10% Aβ normalized to sample area, *$10^7$) | Total vessel-associated NT12 area (normalized to total small + medium CD31+ vessel area) |
|---|---|---|---|
| Baseline (10) | 127 ± 12.8 | 41 ± 4.2 | 0.125 ± 0.0195 |
| 0.03 g/kg food (15) | 288 ± 21.9 | 91 ± 5.9 | 0.286 ± 0.0313 |
| 0.3 g/kg food (13) | 195 ± 21.9 | 56 ± 6.1 | 0.194 ± 0.0201 |
| Vehicle (18) | 326 ± 26.5 | 89 ± 7.0 | 0.271 ± 0.0169 |

One animal has been removed in the 0.03 g/kg treatment group due to technical reasons in the vessel size evaluation.

TABLE 33

Effect of Compound 1 treatment on CAA frequency and amyloid-beta in large CD31-positive vessels, normalized to total sample area or total large CD31+ vessel area (values are mean and SEM)

| Treatment group (n) | Number vessels with >10% Aβ | CAA Frequency (number vessels with >10% Aβ normalized to sample area, *$10^7$) | Total vessel-associated NT12 area (normalized to total CD31+ area) |
|---|---|---|---|
| Baseline (10) | 21 ± 3.4 | 6.7 ± 1.1 | 0.63 ± 0.08 |
| 0.03 g/kg food (15) | 29 ± 3.0 | 9.3 ± 1.0 | 0.79 ± 0.05 |
| 0.3 g/kg food (13) | 22 ± 2.2 | 6.5 ± 0.6 | 0.77 ± 0.04 |
| Vehicle (18) | 28 ± 4.0 | 7.8 ± 1.2 | 0.78 ± 0.06 |

One animal has been removed in the 0.03 g/kg treatment group due to technical reasons in the vessel size evaluation.

TABLE 34

Treatment effects and statistics for CAA frequency and normalized amyloid-beta in CD31-positive vessels (Dunnett's multiple comparison test)

| Groups compared | Number vessels with >10% Aβ | CAA Frequency (number vessels with >10% Aβ normalized to sample area, *$10^7$) | Total vessel-associated NT12 area (normalized to total CD31+ area) |
|---|---|---|---|
| 0.03 g/kg vs vehicle | −10% n.s. | −4% n.s. | +14% n.s. |
| 0.3 g/kg vs vehicle | −39% $p < 0.001$ | −29% $p < 0.05$ | −19% n.s. |
| Vehicle vs baseline | +140% $p < 0.0001$ | +114% $p < 0.0001$ | +61% $p < 0.05$ | n.s.: not significant

TABLE 35

Treatment effects and statistics for CAA frequency and normalized amyloid-beta in small + medium CD31-positive vessels (Dunnett's multiple comparison test)

| Groups compared | Number vessels with >10% Aβ | CAA Frequency (number vessels with >10% Aβ normalized to sample area, *$10^7$) | Total small + medium vessel-associated NT12 area (normalized to total CD31+ small + medium vessel area) |
|---|---|---|---|
| 0.03 g/kg vs vehicle | −12% n.s. | +2% n.s. | +6% n.s. |
| 0.3 g/kg vs vehicle | −40% $p < 0.001$ | −37% $p < 0.005$ | −28% $p < 0.05$ |
| Vehicle vs baseline | +157% $p < 0.0001$ | +116% $p < 0.0001$ | +117% $p < 0.001$ | n.s.: not significant

TABLE 36

Treatment effects and statistics for CAA frequency and normalized amyloid-beta in large CD31-positive vessels (Dunnett's multiple comparison test)

| Groups compared | Number vessels with >10% Aβ | CAA Frequency (number vessels with >10% Aβ normalized to sample area, *$10^7$) | Total vessel-associated NT12 area (normalized to total CD31+ area) |
|---|---|---|---|
| 0.03 g/kg vs vehicle | +4% n.s. | +20% n.s. | −1% n.s. |
| 0.3 g/kg vs vehicle | −21% n.s. | −17% n.s. | −4% n.s. |
| Vehicle vs baseline | +36% n.s. | +17% n.s. | +26% n.s. | n.s.: not significant

Example 7

13-week Oral Safety Study in Plaque Bearing Transgenic APP23 Mice

Purpose of Study

The main purpose of the study was to evaluate microhaemorrhagic lesions (by MRI and brain histopathology) in aged APP23 mice after treatment with Compound 1 at an efficacious dose and to compare the extent of microhaemorrhage formation to a positive control (i.e. mice that were passively immunised with the β1 antibody (Paganetti P A et al., 1996)). A similar study is previously described in the literature, Beckmann N et al., 2016. The APP23 mouse strain was chosen because of the existence of microhaemorrhages in aged animals. Females were chosen because of having a much higher overall Aβ load, a higher Aβ40/Aβ42 ratio and thus more pronounced microhaemorrhages.

Materials and Methods

Test Articles:

Compound 1; oral administration form: 0.3 g/kg food in feed admixtures (pellets) ad libitum β1 antibody (4.12 mg/mL in citrate buffer 50 mM/140 nM NaCl; aggregation 0.24%)

β1 antibody dosage form: dilution of β1 antibody with 90 nM NaCl/50 nM Tris pH 7.1; Concentration: 1.236-fold dilution to a final concentration of 3.33 mg/mL β1 antibody administration: intraperitoneal, once weekly. Dosage volume: 0.15 mL/mouse (maximum 10 mL/kg)

Experimental Animals:

Animal species and strain: Mouse; transgenic APP23 (B6.D2-Tg(Thy1App)23/1Sdz)

Sex: Females (females have a much higher overall Aβ load, a higher Aβ40/Aβ42 ratio and thus more pronounced microhaemorrhages)

Number of study animals assigned to the dosing phase: APP23: 60 females

Age: Approximately 17-18 months (at start of dosing)

Body weight range: 26 to 36 g (at start of dosing)

Magnetic Resonance Imaging (MRI)

For MRI investigations, mice were anesthetized with 1.5% isoflurane (Abbott, Cham, Switzerland) in a mixture of oxygen/$N_2O$ (2:1) administered via a face mask and placed in a Plexiglas cradle. The body temperature of the mice was kept at 36.5±0.5° C. via integrated water hoses in the animal bed. No stereotactic holding was used. Respiration was monitored throughout the acquisitions. The duration of an imaging session was of about 15 minutes, including positioning of the mouse.

Measurements were carried out with a Biospec 70/30 spectrometer (Bruker Medical Systems, Ettlingen, Germany) operating at 7.0 T, equipped with an actively shielded gradient system. The operational software of the scanner was Paravision 5.1 (Bruker). Images were obtained using a three-dimensional (3D) T2*-weighted gradient-echo sequence with the following imaging parameters: repetition time 19.3 ms; echo time 10 ms; matrix 256×128×192; field-of-view 1.5×1.5×2.0 cm3, 2 averages. Total acquisition time for an image having a pixel size of 59×117×104 µm3 was of 11.86 min.

Acquisition and analysis of the MRI data were performed by a blinded investigator. Sites in the cortex and thalamus presenting signal attenuation with a minimum diameter of 70 µm (lesions) were analyzed throughout the whole brain. To ensure that the same site (lesion) was not counted multiple times, its presence was carefully controlled over several consecutive slices from the 3D data set. The total volume of the lesions was assessed using ImgTool, an IDL (Interactive Data Language Research Systems, Boulder, Colo., USA) based software. Images were first weakly lowpass filtered with a Gaussian profile filter and then transformed into a set of four grey level classes using adaptive Lloyd-Max histogram quantization. This method avoided operator bias due to arbitrary choice of threshold levels on each image. A detailed description of the software can be found in Babin A L et al., 2012, or in Egger C et al., 2013. For each slice of a 3D data set, the areas of the signal attenuation sites within an external border were determined by applying the image segmentation algorithm. This analysis has been repeated for every slice of the 3D data set. The total volume of lesions was then computed by multiplying the sum of lesion areas by the slice thickness (104 µm).

Sampling and Histological Processing of Tissues

Sections of brain were collected at necropsy from all scheduled animals. Cerebellum, last piece after level 7, was sampled for determination of brain concentrations of Compound 1 (for description of brain section levels see Bolon B et al., 2013). Rest of the brain was fixed in 10% neutral-buffered formalin.

Four brain sections were processed and stained with hematoxylin and eosin (H&E) and Perls' Prussian blue for hemosiderin deposits, levels 2, 3, 4, as described in Bolon B et al., 2013, and one additional slide at hypothalamus level (level 2').

Procedure for brain collection: Cerebellum was separated from cerebrum. Remaining cerebrum (from the anterior to level 5) was transferred into formalin for pathology.

Microscopic Examination

Brain sections stained with haematoxylin and eosin and with Perls' Prussian blue, were examined under a light microscope. The distribution, size and staining intensity of hemosiderin deposits in Perls' Prussian blue-stained sections were assessed based on the grading scheme in Table 37.

TABLE 37

Grading scale of hemosiderin deposition in the brain

| | Minimal (Grade 1) | Slight (Grade 2) | Moderate (Grade 3) |
|---|---|---|---|
| Evaluation criteria | Very small haemosiderin deposits associated with blood vessels and/or β-amyloid plaque | Small haemosiderin foci associated with blood vessels and/or β-amyloid plaques | Moderate sized haemosiderin foci associated with blood vessels and/or β-amyloid plaques |

The assessment of all other brain changes was made on the haematoxylin and eosin stained sections with haemorrhage, amyloid plaques and vascular inflammation graded as follows:—:

The distribution, size and staining intensity of haemorrhage in the brain was assessed using the same criteria as those used to grade haemosiderin.

The extent of amyloid plaques in controls was arbitrarily given the value of moderate (grade 3) and any brain with notably fewer plaques was graded as slight (grade 2).

The severity of vascular inflammation was graded either minimal (grade 1) where ≤5 affected vessels/brain were identified, or slight (grade 2) where ≥6 affected vessels/brain were identified.

Plasma and Brain Concentrations of Compound 1

Blood was obtained from all the animals at necropsy. Approximately 0.3 mL of whole blood was collected after euthanasia from the vena cava into tubes containing EDTA as anticoagulant. The tubes were placed in ice water during the sampling period. Plasma was separated thereafter by centrifugation (10 min, 1270 G, +4° C.) and transferred to one uniquely labelled clear tube (1.8 mL NUNC 2D coded tubes from Thermo) and frozen at −70° C. or below. Concentrations of Compound 1 in plasma were measured using an LC-MS/MS method.

Brain concentrations of Compound 1 were determined in brain samples (level 7) using an LC-MS/MS method. About 100 to 200 mg of brain tissue were collected, weighed into 1.8 mL NUNC 2D coded tubes from Thermo, and frozen at −70° C. or below.

Feed Pellet Concentration Determination of Compound 1

Each individual pellet was weighed in a 50 mL tube and broken into pieces. 2-3 mL of extraction solvent (ACN/water 8:2 (v/v)) was added and the resulting mixture was shaken for 5 h at 600 rpm. The mixture was then centrifuged at 2500 rpm for 10 min in centrifugal vial+filter (centrifugal filter with low binding durapore PVDF membrane 0.45 um) and analyzed by Ultra Performance Liquid Chromatography (UPLC) with 2 injections per vial (1-5 µL of injection).

Statistical Analyses

Means and standard deviations (SD), standard error of the mean (SEM) and coefficient of variation (CV) as indicated accordingly were calculated and an Analysis of Variance (ANOVA) performed. For the analysis of body weights a 2way ANOVA with Turkey's multiple comparison test was performed using GraphPad Prism 6. ANOVA with random effects statistical analyses were performed on MRI data using Systat Version 13 (Systat Software, Inc., San Jose, Calif., USA).

Results

Body Weight

All treatment groups displayed weight gain during the study and there was no indication for any weight loss related to the treatment (FIG. 26).

Magnetic Resonance Imaging

Total lesion volumes were measured at the start of the experiment (baseline) and at 1, 2 and 3 months of treatment (FIG. 27). The total lesion volume normalised to baseline (transformed to the natural logarithm) was also determined (FIG. 28), as was the lesion volume increase factor calculated relative to baseline measurements (FIG. 29). In the control group an increase in lesion volume due to aging was observed. The β1 antibody treatment group showed exacerbated lesion volume increase during the study as expected. Despite not reaching significance, there was a trend towards reduced normalised lesion volumes for mice treated with Compound 1 compared to control APP23 mice (FIGS. 28 and 29). An age-related lesion number increase was observed. Lesion numbers, however, were not different among the treatment groups (lesion numbers at month 3 (mean±SEM) for control: 11.2±1.5, Compound 1: 11.5±2.0, β1 antibody: 12.4±1.6).

Taken together, Compound 1 treatment did not exacerbate lesion volumes detected by MRI and a trend towards a reduction in normalised lesion volumes was observed.

Toxicokinetics

Compound 1 concentration was determined in mouse plasma and brain tissues at the end of the study in Group 2 animals. The mean Compound 1 concentration in plasma was 1210 ng/mL with a moderate inter-animal variability (coefficient of variation of 15.9%).

The mean Compound 1 concentration in brain tissue was 4034 ng/g with a moderate inter-animal variability (coefficient of variation of 29.4%). The average of the ratio brain over plasma was 3.3. Compound 1 concentrations found in brain ranged between 2.2 and 6.1 fold when compared to the plasma on day 96.

Post-mortem Investigations

Post-mortem analysis was performed at the end of the study following 3 months treatment with Compound 1 or β1 antibody.

Macroscopic Findings

There were no apparent treatment-related macroscopic observations at necropsy in any animal.

Microscopic Findings (Brain)

The microscopic observations in the brain are summarized in Table 38.

TABLE 38

Summary of brain microscopic observations

| Group number | 1 | 2 | 3 |
| --- | --- | --- | --- |
| Treatment | Untreated control | Compound 1 | β1 antibody |
| Number examined/group | 19* | 15 | 18 |
| Haemosiderin (Perls' staining) | | | |
| Grade 1 | 9 | 7 | 18 |
| Grade 2 | 1 | 0 | 0 |
| Grade 3 | 0 | 0 | 0 |
| % affected | 53 | 47 | 100 |
| Haemorrhage | | | |
| Grade 1 | 6 | 1 | 5 |
| Grade 2 | 0 | 0 | 1 |
| % affected | 32 | 7 | 33 |
| Inflammation, vessel | | | |
| Grade 1 | 7 | 4 | 9 |
| Grade 2 | 1 | 0 | 5 |
| % affected | 42 | 27 | 78 |
| Infarct | | | |
| Grade 1 | 0 | 0 | 1 |
| % affected | 0 | 0 | 6 |
| Thrombus | | | |
| Grade 1 | 2 | 0 | 0 |
| Grade 2 | 0 | 0 | 0 |
| % affected | 11 | 0 | 0 |
| Amyloid plaques | | | |
| Grade 2 | 0 | 4 | 0 |
| Grade 3 | 19 | 11 | 18 |
| % affected | 100 | 100 | 100 |

TABLE 38-continued

Summary of brain microscopic observations

| Group number | 1 | 2 | 3 |
|---|---|---|---|
| Mineralisation | | | |
| Grade 1 | 2 | 2 | 2 |
| Grade 2 | 0 | 0 | 0 |
| % affected | 11 | 13 | 11 |

*= Single animal discounted from evaluation as amyloid plaques were absent from brain.
Grade 1 = minimal, grade 2 = slight, grade 3 = moderate.

Haemosiderin deposits, identified by their blue staining reaction with Perls' Prussian blue, were identified in many animals in all groups. Usually these deposits were found near small blood vessels in the cerebral cortex of the brain. Less frequently, they were present near meningeal blood vessels or associated with amyloid plaques in the brain. In Compound 1-treated mice the incidence and severity were similar to untreated controls with only one or two foci being present in affected brains. In contrast, β1 antibody administration was associated with a 100% incidence.

Haemorrhage was identified in H&E stained sections less frequently than the presence of haemosiderin. In some instances, haemorrhage was present in the same foci as haemosiderin but in foci of recent haemorrhage, haemosiderin was absent. Haemorrhage was less common in Compound 1-treated mice compared to the untreated controls and the β1 antibody-treated group.

Inflammation of small blood vessels was most frequently observed in the meninges and only occasionally in the brain itself. Morphology varied from infiltration of mononuclear cells into the adventitia to more pronounced inflammation accompanying necrosis and hyalinisation of the blood vessel wall. Blood vessel inflammation was least marked in Compound 1-treated mice and most marked in the β1 antibody-treated group.

Very occasionally thrombus formation was seen in affected blood vessels or small areas of previous necrosis (infarct) of neighbouring brain tissue were present in untreated controls and β1 antibody-treated mice but not in the Compound 1-treated mice.

The extent of plaque formation appeared reduced in some Compound 1-treated mice compared to those in the other three groups.

Two animals in every group showed mineralisation of plaques in the thalamus, with no indication of an effect by Compound 1 or the β1 antibody on this change.

Conclusion

The purpose of this safety study in aged APP23 mice was to evaluate consequences of amyloid-β based therapies on microhaemorrhages in the brain. Compound 1 was used in feed dosing at a dose of 0.3 g/kg since a maximal pharmacodynamic effect on amyloid-β lowering in APP23 mice had been observed previously at this dose. Passive immunization with β1 antibody served as a positive control based on results of Pfeifer M et al., 2002, showing enhanced occurrences of microhaemorrhages.

Chronic treatment with Compound 1 as well as β1 antibody did not lead to any change in body weight. Feed pellet analysis revealed a 29% lower value of Compound 1 than the anticipated 0.3 g/kg probably due to the large-scale manufacturing process. Nevertheless, in toxicokinetic analysis at the end of the study Compound 1 was measurable in plasma following in-feed administration of Compound 1 in all treated animals with moderate inter-animal variability.

The Compound 1 levels in plasma were as expected and comparable to previous studies on a dose-normalized basis. At necropsy, Compound 1 was measurable in the brain following in-feed administration of Compound 1 with moderate inter-animal variation. Again, Compound 1 levels in brain were as expected and comparable to previous studies. The brain/plasma ratio was 3.3.

The microhaemorrhagic lesion volume in brain was measured by MRI at baseline and at 1, 2 and 3 months of treatment. During aging the lesion volume was increasing as observed in the control group. The β1 antibody treatment exacerbated the lesion volume increase during the course of the study as expected (Pfeifer M et al. 2002, Beckmann N et al. 2016). Compound 1 treatment, however, did not show any exacerbation of lesion volume detected by MRI. Moreover, despite not reaching significance, there was a trend towards reduced normalized lesion volumes for mice treated with Compound 1 compared to control APP23 mice.

At histopathological examination, Compound 1 administration appeared to reduce the incidence of recent microhaemorrhage and inflammation of small blood vessels in the brain but did not influence the extent of haemosiderin formation (indicative of historic microhaemorrhage) when compared to untreated controls. The positive control β1 antibody increased both microhaemorrhage and vascular inflammation. Although the study was not designed to quantify the extent of amyloid plaque formation, this appeared to be decreased in some Compound 1-treated mice.

Example 8

In Human Study of Pharmacokinetics of Compound 1 When 0/En Alone and in Combination with the Strong CYP3A4 Inhibitor Itraconazole or the Strong CYP3A4 Inducer Rifampicin In a drug-drug interaction (DDI) study in healthy volunteers, the effect of a strong CYP3A4 inhibitor (itraconazole) and a strong CYP3A4 inducer (rifampicin) on the PK of Compound 1 was evaluated. The DDI study design is outlined in FIG. 30. Itraconazole, at a dose of 200 mg q.d., increased mean AUC of Compound 1 2-3-fold and mean Cmax of Compound 1 by 25%, when given together with Compound 1 as compared to when Compound 1 was given alone (Table 39). Rifampicin, at a dose of 600 mg q.d., decreased mean AUC of Compound 1 5-6-fold and mean Cmax of Compound 1 2.5-fold, when given together with Compound 1 as compared to when Compound 1 was given alone (Table 40). In conclusion, the effect of a strong CYP3A4 inducer and a strong CYP3A4 inhibitor on Compound 1 exposure in a Phase 1 study has shown that CYP3A4 is of major importance for the elimination of Compound 1.

TABLE 39

Pharmacokinetic results - Statistical analysis of the effect of itraconazole on the plasma PK parameters of Compound 1: Compound 1 30 mg SD + itraconazole 200 mg QD vs Compound 1 30 mg SD

| Parameter [Unit] | Treatment | n* | Adjusted geometric mean | Geometric mean ratio (Test/Reference) | 90% CI for ratio |
|---|---|---|---|---|---|
| AUCinf (ng*hr/mL) | Cmpd 1 30 mg SD | 17 | 3560 | 3.05 | [2.91, 3.20] |
| | Cmpd 1 30 mg SD + Itraconazole 200 mg QD | 17 | 10900 | | |

TABLE 39-continued

Pharmacokinetic results - Statistical analysis of the effect of itraconazole on the plasma PK parameters of Compound 1: Compound 1 30 mg SD + itraconazole 200 mg QD vs Compound 1 30 mg SD

| Parameter [Unit] | Treatment | n* | Adjusted geometric mean | Geometric mean ratio (Test/Reference) | 90% CI for ratio |
|---|---|---|---|---|---|
| AUClast (ng*hr/mL) | Cmpd 1 30 mg SD | 17 | 3150 | 2.20 | [2.11, 2.30] |
| | Cmpd 1 30 mg SD + Itraconazole 200 mg QD | 17 | 6930 | | |
| Cmax (ng/mL) | Cmpd 1 30 mg SD | 17 | 74.1 | 1.23 | [1.18, 1.29] |
| | Cmpd 1 30 mg SD + Itraconazole 200 mg QD | 17 | 91.3 | | | n* = number of subjects with non-missing values.
An ANOVA model with fixed effects for treatment and subject was fitted to each log-transformed PK parameter. Results were back transformed to obtain 'Adjusted geo-mean', 'Geo-mean ratio' and '90% CI'.

TABLE 40

Pharmacokinetic results - statistical analysis of the effect of rifampicin on the plasma PK parameters of Compound 1: Compound 1 100 mg SD + rifampicin 600 mg QD vs Compound 1 100 mg SD

| Parameter [Unit] | Treatment | n* | Adjusted geometric mean | Geometric mean ratio (Test/Reference) | 90% CI for ratio |
|---|---|---|---|---|---|
| AUCinf (ng*hr/mL) | Cmpd 1 100 mg SD | 13 | 10200 | 0.172 | [0.152, 0.194] |
| | Cmpd 1 100 mg SD + Rifampicin 600 mg QD | 13 | 1750 | | |
| AUClast (ng*hr/mL) | Cmpd 1 100 mg SD | 13 | 8560 | 0.196 | [0.176, 0.219] |
| | Cmpd 1 100 mg SD + Rifampicin 600 mg QD | 13 | 1680 | | |
| Cmax (ng/mL) | Cmpd 1 100 mg SD | 13 | 222 | 0.414 | [0.365, 0.470] |
| | Cmpd 1 100 mg SD + Rifampicin 600 mg QD | 13 | 92.2 | | | n* = number of subjects with non-missing values.
An ANOVA model with fixed effects for treatment and subject was fitted to each log-transformed PK parameter. Results were back transformed to obtain 'Adjusted geo-mean', 'Geo-mean ratio' and '90% CI'.

Example 9

Summary of a Randomised, Double-blind, Placebo-controlled, Study to Evaluate the Efficacy of Compound 1 in Participants at Risk for the Onset of Clinical Symptoms of AD and CAA In the clinical trial described herein in Table 41, the identification of ApoE4 homozygotes is employed as a prognostic enrichment strategy to select individuals with a greater likelihood of having substantial worsening in cognition and/or development of CAA (and subsequent microbleeds or intracerebral haemorrhages), in a reasonable timeframe, that can be practically assessed within the setting of a clinical trial. This study is listed in ClinicalTrials.gov under the NCT02565511 Identifier code. In the alternative, this example may be conducted with cognitively unimpaired ApoE4 carriers (homozygotes; or heterozygotes with additional enrichment for brain amyloid ("amyloid-positivity") determined, for example, by PET or CSF measurement), aged 60 to 75 years, at a once daily oral dose of 15 or 50 mg Compound 1. This study is listed in ClinicalTrials.gov under the NCT03131453 Identifier code.

During the treatment duration of at least 5 years in the proposed clinical trial, it is expected that a significant proportion of the participants will be diagnosed with mild cognitive impairment (MCI), dementia due to AD, and/or develop CAA or a worsening of CAA.

TABLE 41

Summary of a randomised, double-blind, placebo-controlled, study to evaluate the efficacy of Compound 1 in participants at risk for the onset of clinical symptoms of AD and/or the development of CAA

| | |
|---|---|
| Title | A randomized, double-blind, placebo-controlled study to evaluate the efficacy of Compound 1 in participants at risk for the onset of clinical symptoms of Alzheimer's disease (AD). |
| Study type | Interventional. |
| Purpose and rationale | The purpose of this study is to determine the effects of the therapy on cognition, global clinical status, and underlying pathology in participants at risk for the onset of clinical symptoms of AD. Cognitively unimpaired individuals with APOE4 homozygote (HM) genotype and age 60 to 75 years, inclusive, are selected as they represent a population at particularly high risk of progression to Mild Cognitive impairment (MCI) due to AD and/or dementia due to AD. |
| Primary Objective(s) | To demonstrate the effects of Compound 1, vs. placebo on Time-to-event (TTE), with event defined as a diagnosis of MCI due to AD or dementia due to AD, whichever occurs first during the course of the study. To demonstrate the effects of Compound 1 vs. placebo on cognition as measured by the change from Baseline to Month 60 in the APCC (API Preclinical Composite Cognitive Battery) test score (Langbaum J B et al., 2014). |

TABLE 41-continued

Summary of a randomised, double-blind, placebo-controlled, study to
evaluate the efficacy of Compound 1 in participants at risk for the
onset of clinical symptoms of AD and/or the development of CAA

| | |
|---|---|
| Secondary Objectives | Key secondary objective<br>To demonstrate the effects of Compound 1, vs. placebo on global clinical status as measured by the change from Baseline to Month 60 in Clinical Dementia Rating Scale Sum of Boxes (CDR-SOB) score (Morris J C, 1993).<br>Secondary objectives<br>To demonstrate the safety and tolerability of Compound 1, vs. placebo as measured by adverse events (AEs), and changes in the brain structural MRI, laboratory tests, skin examinations, non-cognitive neurological and psychiatric findings including Columbia Suicide Severity Rating Scale (C-SSRS) (Posner K et al., 2011), vital signs and electrocardiogram (ECG).<br>To demonstrate the effects of Compound 1, vs. placebo on cognition as measured by changes from Baseline to Month 60 on the Total Scale score and individual neurocognitive domain index scores of the Repeatable Battery for the Assessment of Neuropsychological Status (RBANS) (Randolph C, 1998).<br>To demonstrate the effects of Compound 1, vs. placebo on function as measured by the change from Baseline to Month 60 in the Everyday Cognition scale (ECog) total scores reported by the participant and study partner, respectively (Farias S T et al., 2008).<br>To demonstrate the effects of Compound 1, vs. placebo on AD-related biomarkers (amyloid deposition and measures of neurodegeneration) as measured by change from Baseline to Months 24 and 60 on:<br>Binding of amyloid tracer $^{18}$F-florbetapir obtained using brain positron emission tomography (PET) imaging,<br>Volumetric MRI measurements, and<br>CSF $A\beta_{1-40}$, $A\beta_{1-42}$, total tau and phospho-tau$_{181}$ levels.<br>To assess the effects of Compound 1 vs. placebo on cerebral amyloid angiopathy (CAA) as measured by micro-hemorrhages and white matter hyper-intensities on MRI |
| Study design | The Treatment Epoch follows a randomized, double-blind, placebo-controlled, design in which participants receive the investigational treatment or its matching placebo for at least 60 months up to a maximum of 96 months and no longer than when the target number of events for the TTE endpoint has been observed and confirmed. |
| Population | The Treatment Epoch population will consist of male and female participants at risk for the onset of clinical symptoms of AD, based on their APOE4 HM genotype and age (60 to 75 years of age).<br>Randomization will be stratified by agegroup and region |
| Inclusion criteria | Male or female, age 60 to 75 years inclusive. Females must be considered post-menopausal and not of child bearing potential.<br>Mini-Mental State Examination (MMSE) (Folstein M F et al., 1975) total score ≥ 24 and cognitively unimpaired as evaluated by memory tests performed at screening and as defined by:<br>Homozygous APOE4 genotype,<br>Participant's willingness to have a study partner |
| Exclusion criteria | Current chronic treatment (>3 months) with strong CYP3A4 inducers or strong CYP3A4 inhibitors.<br>Any disability that may prevent the participants from completing all study requirements.<br>Current medical or neurological condition that might impact cognition or performance on cognitive assessments.<br>Advanced, severe progressive or unstable disease that may interfere with the safety, tolerability and study assessments, or put the participant at special risk.<br>History of malignancy of any organ system, treated or untreated, within the past 60 months.<br>Indication for, or current treatment with ChEls and/or another AD treatment (e.g. memantine).<br>Brain MRI results showing findings unrelated to AD that, in the opinion of the Investigator might be a leading cause to cognitive decline, might pose a risk to the participant, or might prevent a satisfactory MRI assessment for safety monitoring.<br>Suicidal Ideation in the past six months, or Suicidal Behavior in the past two years.<br>A positive drug screen at Screening, if, in the Investigator's opinion, this is due to drug abuse.<br>Significantly abnormal laboratory results at Screening, not as a result of a temporary condition.<br>Current clinically significant ECG findings. |
| Investigational and reference therapy | Compound 1 and placebo:<br>Arm #1: Compound 1, 50 mg capsule p.o. for once daily administration<br>Arm #2: Placebo to Compound 1 p.o. |

TABLE 41-continued

Summary of a randomised, double-blind, placebo-controlled, study to evaluate the efficacy of Compound 1 in participants at risk for the onset of clinical symptoms of AD and/or the development of CAA

|  |  |
|---|---|
|  | Participants will be dispensed medication supplies for 3-month treatment with Compound 1, 50 mg or placebo for once daily, oral intake for the duration of the Treatment Epoch. |
| Efficacy assessments | MCI due to AD or dementia due to AD (MCI/dementia) (diagnostic verification form) |
|  | API Preclinical Composite Cognitive (APCC) Battery |
|  | Repeatable Battery for the Assessment of Neuropsychological Status (RBANS) |
|  | Raven's Progressive Matrices (Raven J C et al., 1992; Raven J C, 2000) |
|  | Mini Mental State Examination (MMSE) |
|  | Clinical Dementia Rating Scale Sum of Boxes (CDR-SOB) |
|  | Everyday Cognition Scale (ECog) |
|  | Neuropsychiatric Inventory-Questionnaire (NPI-Q) (Kaufer D I et al., 2000) |
|  | Geriatric Depression Scale (GDS) (Sheikh J I, Yesavage J A, 1986) |
|  | Lifestyle questionnaire (Carlsson A C et al., 2013) |
|  | Quality of Life (QOL -AD) (Logsdon R G et al., 1999 and Thorgrimsen L et al., 2003) |
| Safety assessments | Physical and Neurological examination (including skin evaluation) |
|  | Vital signs |
|  | Weight |
|  | Laboratory evaluations |
|  | Electrocardiogram (ECG) |
|  | Safety brain MRI scans |
|  | Adverse events and serious adverse events |
|  | Columbia-Suicide Severity Rating Scale (C-SSRS) |
| Other assessments | Pharmacokinetics |
|  | Biomarkers |
|  | Imaging biomarkers |
|  | Volumetric MRI |
|  | Resting state functional MRI |
|  | Amyloid PET |
|  | FDG PET |
|  | Fluid biomarkers |
|  | CSF-based biomarkers |
|  | Blood-based biomarkers (serum, plasma, blood for pharmacogenomics (RNA) and pharmacogenetics (DNA)) |
| Data analysis | The primary analysis comprises statistical tests of hypotheses of both primary endpoints. The statistical tests will compare active investigational treatment versus matching placebo as control group. A pre-defined testing strategy will be used to adjust the type I error rate for testing more than one hypothesis. |
|  | Secondary endpoints (CDR-SOB, ECog, individual scales included in the APCC battery and RBANS, PET, Volumetric MRI, Total tau, phosphorylated tau in CSF) will all be analyzed using longitudinal models such as a generalized linear mixed model (GLMM) for the CDR-SOB and a mixed model repeat measure (MMRM) similar to the approach for the primary endpoint APCC with treatment as factor and adjusting for important covariates. For the secondary safety parameters (AEs, SAEs, laboratory results, vital signs, ECG, safety brain MRI scans) descriptive statistics will be provided. |

Example 10

Pharmaceutical Composition Comprising Compound 1

The pharmaceutical composition used in the clinical studies described in Examples 3 and 4 was formulated as a hard gelatin capsule (e.g. Capsugel, size 3) comprising the ingredients shown in Table 42 and prepared as described below.

TABLE 42

Manufacturing of 1 mg, 10 mg and 75 mg hard gelatin capsules of Compound 1

| Ingredient | Amount per batch (kg) | | |
| --- | --- | --- | --- |
| | 1 mg | 10 mg | 75 mg |
| Batch size | 7500 units | 16,000 units | 7,100 units |
| Capsule fill | | | |
| Compound 1[1] | 0.0075 | 0.1600 | 0.5325 |
| Mannitol | 0.8568 | 1.7238 | 0.4242 |
| Pregelatinised starch | 0.2775 | 0.5520 | 0.1243 |
| Low-substituted Hydroxypropyl cellulose | 0.0660 | 0.1408 | 0.0625 |
| Hydroxypropylcellulose | 0.0432 | 0.0922 | 0.0409 |
| Sodium stearyl fumarate | 0.0180 | 0.0384 | 0.0170 |
| Talc | 0.0060 | 0.0128 | 0.0057 |
| Purified water[2] | q.s. | q.s. | q.s. |
| Weight capsule fill mix | 1.2750 | 2.7200 | 1.2071 |
| Empty capsule shell | | | |
| Capsule shell (theoretical weight) | 0.3600 | 0.7680 | 0.3408 |
| Total batch weight | 1.6350 | 3.4880 | 1.5479 |

[1]Corresponding to a corrected drug substance content (=cc) of 100%. A compensation of drug substance is performed if the corrected drug substance content is ≤99.5%. The difference in weight is adjusted with Mannitol. The cc is calculated as given below:
100% − total related substances % − (residual solvents + water)%
[2]Removed during processing Other batch sizes or dosage strengths may be prepared depending on clinical requirements and/or available equipment. The weight of individual components for other batch sizes corresponds proportionally to the stated composition.

Description of Manufacturing Process of Compound 1: 1 mg and 10 mg Hard Gelatin Capsules 1. Blend Compound 1 drug substance and portion of mannitol.
2. Sieve the mixture of step 1.
3. Blend the mixture of step 2.
4. Sieve portion of mannitol and add to the mixture of step 3.
5. Blend the mixture of step 4.
6. Sieve remaining portion of mannitol, pre-gelatinised starch, low-substituted hydroxypropyl cellulose and hydroxypropyl cellulose. Add the sieved ingredients to the mixture of step 5.
7. Blend the mixture of step 6.
8. Sieve the blend of step 7.
9. Blend the mixture of step 8.
10. Dissolve hydroxypropyl cellulose in purified water under stirring to form binder solution. Add binder solution to the blend of step 9 and knead/granulate the mass.
11. Perform wet screening of mass from step 10 if necessary.
12. Dry the wet granules of step 11.
13. Screen the dried granules of step 12.
14. Sieve mannitol, low-substituted hydroxypropyl cellulose and talc and add to the sieved granules of step 13.
15. Blend the mixture of step 14.
16. Sieve sodium stearyl fumarate and add to mixture of step 15.
17. Blend the mixture of step 16 to get final blend.
18. Encapsulate the final blend from step 17.

Description of Manufacturing Process of Compound 1: 75 mg Hard Gelatin Capsules

1. Sieve Compound 1 drug substance, mannitol, pre-gelatinised starch, low substituted hydroxypropyl cellulose, hydroxypropyl cellulose.
2. Blend the sieved materials of step 1.
3. Sieve the mixture of step 2.
4. Blend the mixture of step 3.
5. Dissolve hydroxypropyl cellulose in purified water under stirring to form binder solution. Add binder solution to the blend of step 4 and granulate the mass.
6. Perform wet screening if necessary
7. Dry the wet granules of step 6.
8. Screen the dried granules of step 7.
9. Sieve mannitol, low-substituted hydroxypropyl cellulose and talc and add to sieved granules of step 8.
10. Blend the mixture of step 9.
11. Sieve sodium stearyl fumarate and add to step 10.
12. Blend the mixture of step 11 to get final blend.
13. Encapsulate the final blend of step 12.

The processes described above may be reasonably adjusted, while maintaining the same basic production steps, to compensate for different batch sizes, dosage strengths, and/or equipment characteristics. Granulation steps may be divided in sub-batches to utilise the qualified range of the equipment.

REFERENCES

Babin A L et al., (2012) Bleomycin-induced lung injury in mice investigated by MRI: model assessment for target analysis. Magn. Reson. Med.; 67(2):499-509.

Beckmann N et al., (2016) Longitudinal noninvasive magnetic resonance imaging of brain microhemorrhages in BACE inhibitor-treated APP transgenic mice. Neurobiology of Aging; 45:50-60.

Bolon B et al., (2013) STP Position Paper: Recommended Practices for Sampling and Processing the Nervous System (Brain, Spinal Cord, Nerve, and Eye) during Nonclinical General Toxicity Studies. Toxicologic Pathology; 41(7): 1028-1048.

Carlsson A C et al., (2013) Seven modifiable lifestyle factors predict reduced risk for ischemic cardiovascular disease and all-cause mortality regardless of body mass index: A cohort study. International Journal of Cardiology; 168:946-952.

Castellano J M et al., (2011) Human apoE Isoforms Differentially Regulate Brain Amyloid-b Peptide Clearance. Sci. Transl. Med.; 3(89):89ra57.

Charidimou A et al., (2011) Sporadic cerebral amyloid angiopathy revisited: recent insights into pathophysiology and clinical spectrum. J. Neurol. Neurosurg. Psychiatry; 83(2):124-137.

Chen Y W et al., (2006) Progression of white matter lesions and hemorrhages in cerebral amyloid angiopathy. Neurology; 67(1):83-87.

Cheng A L et al., (2013) Susceptibility-Weighted Imaging is More Reliable Than T2*-Weighted Gradient-Recalled Echo MRI for Detecting Microbleeds. Stroke; 44(10):2782-2786.

Dermaut B et al., (2001) Cerebral amyloid angiopathy is a pathogenic lesion in Alzheimer's disease due to a novel presenilin 1 mutation. Brain; 124:2383-2392.

Egger C et al., (2013) Administration of bleomycin via the oropharyngeal aspiration route leads to sustained lung fibrosis in mice and rats as quantified by UTE-MRI and histology. PLoS One; 8(5):e63432.

Farias S T et al., (2008) The measurement of everyday cognition (ECog): Scale development and psychometric properties. Neuropsychology; 22(4):531-544.

Folstein M F et al., (1975) A practical method for grading the cognitive state of patients for the clinician. J. Psychiat. Res.; 12:189-198.

Forlenza O V et al., (2015) Cerebrospinal fluid biomarkers in Alzheimer's disease: Diagnostic accuracy and prediction of dementia; Alzheimers Dement. (Amst); 1(4):455-463.

Greenberg S M et al., (2014) Outcome Markers for Clinical Trials in Cerebral Amyloid Angiopathy. Lancet Neurol.; 13(4):419-428.

Gurol M E et al., (2016) Florbetapir-PET to diagnose cerebral amyloid angiopathy: A prospective study. Neurology; 87(19):2043-2049.

Herskovitz A Z et al., (2013) A Luminex assay detects amyloid β oligomers in Alzheimer's disease cerebrospinal fluid. PLoS ONE; 8(7):e67898. doi:10.1371/journal.pone.0067898.

Janelidze S et al., (2016) Swedish BioFINDER study group, Hansson O.CSF Aβ42/Aβ40 and Aβ42/Aβ38 ratios: better diagnostic markers of Alzheimer disease. Ann Clin Transl Neurol. 3(3):154-65.

Kaufer D I et al., (2000) Validation of the NPI-Q, a brief clinical form of the Neuropsychiatric Inventory. J. Neuropsychiatry Clin. Neuroscience; 12(2):233-239.

Knouff C et al., (1999) Apo E structure determines VLDL clearance and atherosclerosis risk in mice. J. Clin. Invest.; 103 (11):1579-1586.

Kumar-Singh S, (2008) Cerebral amyloid angiopathy: pathogenetic mechanisms and link to dense amyloid plaques. Genes Brain Behav.; 7(Suppl. 1):67-82.

Langbaum J B et al., (2014) An empirically derived composite cognitive test score with improved power to track and evaluate treatments for preclinical Alzheimer's disease. Alzheimers Dement.; 10(6):666-674.

Logsdon R G et al., (1999) Quality of life in Alzheimer's disease: Patient and caregiver reports. Journal of Mental Health & Aging; 5(1):21-32.

Luo G et al., (2004) CYP3A4 Induction by Xenobiotics: Biochemistry, Experimental Methods and Impact on Drug Discovery and Development. Current Drug Metabolism; 5(6):483-505.

Mattsson N et al., (2015) Predicting Reduction of Cerebrospinal Fluid β-Amyloid 42 in Cognitively Healthy Controls. JAMA Neurology; 72(5):554-560.

Morris J C, (1993) The Clinical Dementia Rating (CDR): Current version and scoring rules. Neurology; 43(11):2412-2414.

Paganetti P A et al., (1996) Amyloid precursor protein truncated at any of the gamma-secretase sites is not cleaved to beta-amyloid. J. Neurosci. Res.; 46(3): 283-293.

Palmqvist S et al., (2016) Cerebrospinal fluid analysis detects cerebral amyloid-β accumulation earlier than positron emission tomography. Brain; 139:1226-1236.

Pfeifer M et al., (2002) Cerebral Hemorrhage After Passive Anti-Aβ Immunotherapy. Science; 298(5597):1379.

Posner K et al., (2011) The Columbia-Suicide Severity Rating Scale: Initial Validity and Internal Consistency Findings From Three Multisite Studies With Adolescents and Adults. Am. J. Psychiatry; 168(12):1266-1277.

Quintino-Santos S R et al., (2012) Homozygosity for the APOE E4 allele is solely associated with lower cognitive performance in Brazilian community dwelling older adults—The Bambui Study. Rev. Bras. Psiquiatr.; 34(4): 440-445.

Randolph C, (1998) The Repeatable Battery for the Assessment of Neuropsychological Status (RBANS). Pearson; San Antonio.

Raven J C et al., (1992) Standard progressive matrices-1992 edition; Raven manual: Section 3. Oxford Psychologists Press; Oxford.

Raven J C, (2000) Standard Progressive Matrices-1998 Edition, updated 2000. Manual for Standard Progressive Matrices (Section 3): NCS Person, Inc.; San Antonio.

Schrader-Fischer G, Paganetti P A, (1996) Effect of alkalizing agents on the processing of the β-amyloid precursor protein. Brain Research; 716(1-2):91-100.

Schrader-Fischer G et al., (1997) Insertion of Lysosomal Targeting Sequences to the Amyloid Precursor Protein Reduces Secretion of βA4. Journal of Neurochemistry 68(4):1571-1580.

Schreiber S et al. (2015) Comparison of Visual and Quantitative Florbetapir F 18 Positron Emission Tomography Analysis in Predicting Mild Cognitive Impairment Outcomes. JAMA Neurol.; 72(10):1183-1190.

Sevrioukova I F, Poulos T L, (2015) Current Approaches for Investigating and Predicting Cytochrome P450 3A4-Ligand Interactions. Adv. Exp. Med. Biol.; 851:83-105.

Sheikh J I, Yesavage J A, (1986) Geriatric Depression Scale (GDS). Recent evidence and development of a shorter version. In T. L. Brink (Ed.), Clinical Gerontology: A Guide to Assessment and Intervention (pp. 165-173). NY: The Haworth Press, Inc.

Shinohara M et al., (2016) Impact of sex and APOE4 on cerebral amyloid angiopathy in Alzheimer's disease. Acta Neuropathol.; 132(2):225-234.

Sperling R A et al., (2011) Toward defining the preclinical stages of Alzheimer's disease: Recommendations from the National Institute on Aging and the Alzheimer's Association workgroup. Alzheimers Dement.; 7(3):280-292.

Sturchler-Pierrat C et al., (1997) Two amyloid precursor protein transgenic mouse models with Alzheimer disease-like pathology. Proc. Natl. Acad. Sci. USA.; 94(24):13287-13292.

Thal D R et al., (2002) Two types of sporadic cerebral amyloid angiopathy. J. Neuropathol. Exp. Neurol.; 61: 282-293.

Thorgrimsen L et al., (2003) Whose Quality of Life Is It Anyway? The Validity and Reliability of the Quality of Life-Alzheimer's Disease (Qol-AD) Scale. Alzheimer Dis. Assoc. Disord.; 17(4):201-208.

Verghese P B et al., (2011) Roles of Apolipoprotein E in Alzheimer's disease and Other Neurological Disorders. Lancet Neurol.; 10(3): 241-252.

Winkler D T et al., (2001). Spontaneous hemorrhagic stroke in a mouse model of cerebral amyloid angiopathy. J. Neurosci.; 21(5):1619-1627.

All references, e.g., a scientific publication or patent application publication, cited herein are incorporated herein by reference in their entirety and for all purposes to the same extent as if each reference was specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for the treatment of cerebral amyloid angiopathy, wherein the method comprises administering to a patient in need thereof a therapeutically effective amount of the compound N-(6-((3R,6R)-5-amino-3,6-dimethyl-6-(trifluoromethyl)-3,6-dihydro-2H-1,4-oxazin-3-yl)-5-fluoropyridin-2-yl)-3-chloro-5-(trifluoromethy)picolinamide, or a pharmaceutically acceptable salt thereof, wherein the patient carries one or two copies of the ApoE4 allele.

2. The method according to claim 1, wherein the patient has Alzheimer's disease.

3. The method according to claim 1, wherein the patient carries one copy of the ApoE4 allele.

4. The method according to claim 1, wherein the patient carries two copies of the ApoE4 allele.

5. The method according to claim 3, wherein the patient is amyloid-positive.

6. The method according to claim 5, wherein the amyloid-positivity is determined by PET or CSF measurement.

7. The method according to claim 1, wherein the patient is between 60 and 75 years of age.

8. The method according to claim 1, wherein the compound is used at a daily dose which results in at least a 70% lowering of Aβ 1-40 in CSF measurement following two weeks of compound exposure.

9. The method according to claim 1, wherein the compound is used at a daily dose which results in at least a 50% lowering of Aβ 1-40 in CSF measurement following two weeks of compound exposure.

10. The method according to claim 1, wherein the compound is used at a dose of 15 mg per day.

11. The method according to claim 1, wherein the compound is used at a dose of 50 mg per day.

12. The method according to claim 1, wherein the compound is in free base form.

13. The method according to claim 1, wherein the compound is comprised within a pharmaceutical composition.

14. The method according to claim 1, wherein the patient is not simultaneously treated with an inhibitor or inducer of CYP3A4.

15. The method according to claim 14, wherein the patient is not simultaneously treated with a CYP3A4 inhibitor or inducer for a period longer than three months.

16. The method according to claim 14, wherein the CYP3A4 inhibitor is a strong inhibitor of CYP3A4; and the CYP3A4 inducer is a strong inducer of CYP3A4.

17. The method according to claim 1, wherein the cerebral amyloid angiopathy is CAA-Type 1.

* * * * *